US011498942B2

(12) United States Patent
Bannantine et al.

(10) Patent No.: US 11,498,942 B2
(45) Date of Patent: Nov. 15, 2022

(54) **ANTIGENIC TRIPEPTIDES DERIVED FROM *MYCOBACTERIUM AVIUM* SUBSP. *PARATUBERCULOSIS* S-TYPE STRAINS, DERIVATIVES AND USES THEREOF**

(71) Applicants: INSTITUT PASTEUR, Paris (FR); INSTITUT NATIONAL DE LA RECHERCHE AGRONOMIQUE (INRA), Paris (FR); THE UNITED STATES OF AMERICA, AS REPRESENTED BY THE SECRETARY OF AGRICULTURE, Washington, DC (US)

(72) Inventors: John P. Bannantine, Ames, IA (US); Gilles Etienne, Toulouse (FR); Sylvie Bay, Paris (FR); Franck Biet, Notre Dame d'Oe (FR)

(73) Assignees: INSTITUT PASTEUR, Paris (FR); INSTITUT NATIONAL DE LA RECHERCHE AGRONOMIQUE (INRA), Paris (FR); THE UNITED STATES OF AMERICA, AS REPRESENTED BY THE SECRETARY OF AGRICULTURE, Washington, DC (US)

( * ) Notice: Subject to any disclaimer, the term of this patent is extended or adjusted under 35 U.S.C. 154(b) by 146 days.

(21) Appl. No.: 16/470,962

(22) PCT Filed: Dec. 20, 2017

(86) PCT No.: PCT/EP2017/083924
§ 371 (c)(1),
(2) Date: Jun. 18, 2019

(87) PCT Pub. No.: WO2018/115183
PCT Pub. Date: Jun. 28, 2018

(65) Prior Publication Data
US 2020/0024307 A1    Jan. 23, 2020

(30) Foreign Application Priority Data

Dec. 20, 2016    (WO) ................. PCT/IB2016/002018

(51) Int. Cl.
| | |
|---|---|
| *C07K 5/087* | (2006.01) |
| *A61K 47/54* | (2017.01) |
| *A61K 47/60* | (2017.01) |
| *A61K 39/04* | (2006.01) |
| *C07K 7/06* | (2006.01) |
| *C12Q 1/689* | (2018.01) |
| *G01N 33/569* | (2006.01) |

(52) U.S. Cl.
CPC ............ *C07K 5/0812* (2013.01); *A61K 39/04* (2013.01); *A61K 47/542* (2017.08); *A61K 47/60* (2017.08); *C07K 7/06* (2013.01); *C12Q 1/689* (2013.01); *G01N 33/5695* (2013.01); *G01N 2333/5428* (2013.01); *G01N 2333/57* (2013.01); *G01N 2469/20* (2013.01); *G01N 2800/26* (2013.01)

(58) Field of Classification Search
CPC ......... A61K 39/00; A61K 39/02; A61K 39/04
USPC .................... 424/184.1, 185.1, 234.1, 248.1
See application file for complete search history.

(56) References Cited

U.S. PATENT DOCUMENTS

| | | | |
|---|---|---|---|
| 5,750,767 A | 5/1998 | Carpino et al. | |
| 8,883,173 B2 | 11/2014 | Reyrat et al. | |

FOREIGN PATENT DOCUMENTS

| | | |
|---|---|---|
| WO | 03/104493 A1 | 12/2003 |
| WO | 2009/053844 A1 | 4/2009 |

OTHER PUBLICATIONS

Wen-Ren Li et al, "An Expedient N-Terminal Attachment Methodology for the Solid Phase Peptide Synthesis" (2000) Synlett, No. 11, pp. 1608-1612.
Cunningham B R et al, "SAR for MHC Class II Binding Tetrapeptides: Correlation With Potential Binding Site", Bioorganic & Medicinal Chemistry Letters, Pergamon, Amsterdam, (1997) vol. 7, No. 1, pp. 19-24.
Balraju V et al, "Synthesis of cyclic peptides using a palladium-catalyzed enyne cycloisomerization", Tetrahedron Letters, Elsevier, Amsterdam, (2006), vol. 47, pp. 3569-3571.
Pawar Sachin A et al, "Linear and cyclic glycopeptide as HIV protease inhibitors", European Journal of Medicinal Chemistry, Editions Scientifique Elsevier, Paris, (2013), pp. 144-154.
Erapalapati V. et al, "Versatile Soluble Oligomeric Styrene Supports for Peptide Synthesis" (2006) Journal of Polymer Science, Part A : Polymer Chemistry, vol. 53, pp. 2501-2509.
Garner P et al., "S-(2-Pyrimidinyl)- and S-(2-( 4, 6-dimetbylpyrimidinyl) )-1,1,3,3-tetrametbylthiouronium hexafluoropbospha tes: novel reagents for in situ peptide coupling" (2006) Tetrahedron Letters, Elsevier, Amsterdam, vol. 43, pp. 483-486.

(Continued)

*Primary Examiner* — Brian Gangle
(74) *Attorney, Agent, or Firm* — Arrigo, Lee, Guttman & Mouta-Bellum LLP

(57) ABSTRACT

The present invention is directed to an isolated synthetic tripeptide of formula H-D-Phe-N-Methyl-L-Val-L-Ala-OMe (SEQ ID NO:1), or a derivative thereof, and to the corresponding lipotripeptides, which are specific to *Mycobacterium avium* subsp. *paratuberculosis* (Map) S-type strain, as well as derivatives and conjugates thereof. The invention also concerns the use of these antigens in different methods and tests for detecting Map infection, especially by detecting humoral response and cell mediated response of infected animals. The invention is also directed to a genetic signature of Map and a mass spectrometry and NMR spectroscopy signature of Map presence or infection.

Figure 1:
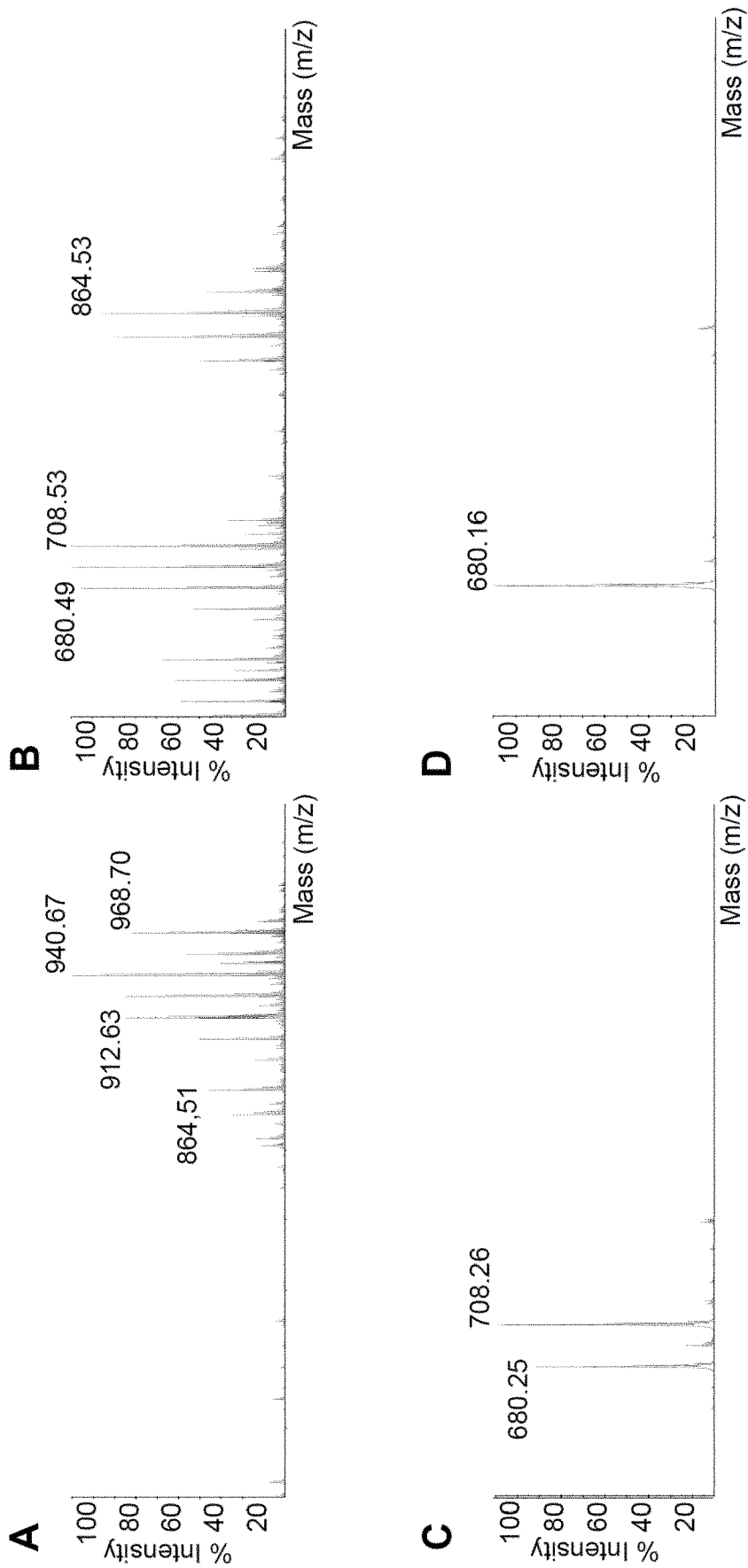

22 Claims, 16 Drawing Sheets
Specification includes a Sequence Listing.

(56) References Cited

OTHER PUBLICATIONS

Oka T et al, "Comparative Specificity of Microbial Acid Proteinases for Synthetic Peptides", (1973) Archives of Biochemistry and Biophysics, Academic Press, vol. 156, pp. 543-551.

Mullican M D et al, "The Synthesis and Evaluation of Peptidyl Aspartyl Aldehydes as Inhibitors of Ice." (1994), Bioorganic & Medicinal Chemistry Letters, Pergamon, Amsterdam, vol. 4, No. 19, pp. 2359-2364.

Sorg G et al, "Progress in the preparation of peptide aldehydes via polymer supported IBX oxidation and scavenging by threonyl resin+" (2005), Journal of Peptide Scie, John Wiley and Sons Ltd, vol. 11, pp. 142-152.

Gratias R et al, "First Step Toward the Quantitative Identification of Peptide 310-Helix Conformation with NMR Spectroscopy: NMR and X-ray Diffraction Structural Analysis of a Fully-Developed 310-Helical Peptide Standard", (1998), Journal of the American Chemical Society, vol. 120, pp. 4763-4770.

K. Dohmann et al, "Characterization of Genetic Differences between *Mycobacterium avium* subsp. *paratuberculosis* Type I and Type II Isolates", (2003), Journal of Clinical Microbiology, vol. 41, No. 11, pp. 5215-5223.

Thibault, V.C. et al, "Combined Multilocus Short-Sequence-Repeat and Mycobacterial Interspersed Repetitive Unit-Variable-Number Tandem-Repeat Typing of *Mycobacterium avium* subsp. *paratuberculosis* Isolates", (2008). J. Clin. Microbiol, vol. 46, No. 12, pp. 4091-4094.

Marsh, I.B., et al, "Genomic Comparison of *Mycobacterium avium* subsp. *paratuberculosis* Sheep and Cattle Strains by Microarray Hybridization", (2006). J. Bacteriol. vol. 188, No. 6, pp. 2290-2293.

Wang, H. et al, "Atlas of nonribosomal peptide and polyketide biosynthetic pathways reveals common occurrence of nonmodular enzymes", (2014). Proc. Natl. Acad. Sci. U. S. A. vol. 111, No. 25, pp. 9259-9264.

Biet, F. et al, "Lipopentapeptide induces a strong host humoral response and distinguishes *Mycobacterium avium* subsp. *paratuberculosis* from *M. avium* subsp. *avium*", (2008). Vaccine vol. 26: pp. 257-268.

Li, L., et al, "The complete genome sequence of *Mycobacterium avium* subspecies *paratuberculosis*" (2005). Proc. Natl. Acad. Sci. U. S. A. vol. 102, No. 35, pp. 12344-12349.

Eckstein, T.M., S. et al, "A Major Cell Wall Lipopeptide of *Mycobacterium avium* subspecies *paratuberculosis*", (2006). J. Biol. Chem. vol. 281, pp. 5209-5215.

Bannantine, J.P. et al, "Genome sequencing of ovine isolates of *Mycobacterium avium* subspecies *paratuberculosis* offers insights into host association", (2012). BMC Genomics, vol. 13, No. 89, pp. 1-7.

Semret, M. et al, "Differentiating Host-Associated Variants of *Mycobacterium avium* by PCR for Detection of Large Sequence Polymorphisms", (2006). J. Clin. Microbiol., vol. 44, No. 3, pp. 881-887.

Holbert, S., M. et al, "Interferon gamma response to *Mycobacteriumavium* subsp. *paratuberculosis* specific lipopentapeptide antigen L5P in cattle" (2015). Res. Vet. Sci. vol. 102: pp. 118-121.

Nahms, (2008) Johne's disease on U.S. dairies, 1991-2007. USDA-APHIS-VS-CEAH Fort Collins, Co. Center for Epidemiology and Animal Health: pp. 1-4.

Riviere, M. et al., "A unique phenylalanine-containing lipopeptide isolated from a rough-colony variant of *Mycobacterium avium*" (1996). Eur. J. Biochem., vol. 241, pp. 682-690.

Rottig, M., et al, "NRPSpredictor2—a web server for predicting NRPS adenylation domain specificity" (2011). Nucleic Acids Res., vol. 39, pp. W362-W367.

Dukkipati V. et al, "Experimental Infection of New Zealand Merino sheep with a suspension of *Mycobacterium avium* subspecies *paratuberculosis* (Map) strain Telford: Kinetics of the immune response, histopathology and Map culture", Vet. Microbiol. Nov. 15, 2016; vol. 195: pp. 136-143.

International Search Report and Written Opinion for PCT Application No. PCT/EP2017/083924, dated Jun. 8, 2018, which is related to this subject application (21 pages).

```
MapK10   1 MKRGDRAYPVTRGQLDIWLAEQTGHLDVAWQLGVLVRIDGAIDPALLHQTMRHVVGEAES 60
            +KRGDRAYPVTRGQLDIWLAEQTGHLDVAWQLGVLVRIDGAIDPALLHQTMRHVVGEAES
S397     1 VKRGDRAYPVTRGQLDIWLAEQTGHLDVAWQLGVLVRIDGAIDPALLHQTMRHVVGEAES 60

MapK10  61 LRASFFEADGQVFQKAVEYSDVDLTFYDLSGSSDPEREVREMTASIQRTPMPLTGPMIKF 120
            LRASFFEADGQVFQKAVEYSDVDLTFYDLSGSSDPEREVREMTASIQRTPMPLTGPM KF
S397    61 LRASFFEADGQVFQKAVEYSDVDLTFYDLSGSSDPEREVREMTASIQRTPMPLTGPMTKF 120

MapK10 121 ALFRTGSAEYYWFTTCHHIAIDGMGIALVGRRIAAVYTALASGKPIPPAFFGSLQDLVGG 180
            ALFRTGSAEYYWFTTCHHIAIDGMGIALVGRRIAAVYTALASGKPIPPAFFGSLQDLVGG
S397   121 ALFRTGSAEYYWFTTCHHIAIDGMGIALVGRRIAAVYTALASGKPIPPAFFGSLQDLVGG 180

MapK10 181 ELEYEASAKFLEDKDYWLAHRPGDGTAGHPPRPADDGRDPYSPSPPVQLDESVIGSVKEL 240
            ELEYEASAKFLEDKDYWLAHRPGDGTAGHPPRPADDGRDPYSPSPPVQLDESVIGSVKEL
S397   181 ELEYEASAKFLEDKDYWLAHRPGDGTAGHPPRPADDGRDPYSPSPPVQLDESVIGSVKEL 240

MapK10 241 SKALGIRRSSVLTAACALLVRGWCADGSDEVVLDFPVSRRVDPKSKTHPGMLAGVVPLVL 300
            SKALGIRRSSVLTAACALLVRGWCADGSDEVVLDFPVSRRVDPKSKTHPGMLAGVVPLVL
S397   241 SKALGIRRSSVLTAACALLVRGWCADGSDEVVLDFPVSRRVDPKSKTHPGMLAGVVPLVL 300

MapK10 301 HAPAAATFADFCRHVDQRSREALRHQQFPTRTLDGEGDFSGPRQAPNRVVVNFVPARLTL 360
            HAPAAATFADFCRHVDQRSREALRHQQFPTRTLDGEGDFSGPRQAPNRVVVNFVPARLTL
S397   301 HAPAAATFADFCRHVDQRSREALRHQQFPTRTLDGEGDFSGPRQAPNRVVVNFVPARLTL 360

MapK10 361 SLADVPATATYTSFGPVGHFGLFFLGFGDQQFLSTVGTGQPLANFDATDLAERLQRILAA 420
            SLADVPATATYTSFGPVGHFGLFFLGFGDQQFLSTVGTGQPLANFDATDLAERLQRILAA
S397   361 SLADVPATATYTSFGPVGHFGLFFLGFGDQQFLSTVGTGQPLANFDATDLAERLQRILAA 420

MapK10 421 MAADPARLLSSLDVLRDPEHAQLEALGNTAVLTRTPGPAVSVPELFATQVARAPQDVALV 480
            MAADPARLLSSLDVLRDPEHAQLEALGNTAVLTRTPGPAVSVPELFATQVARAPQDVALV
S397   421 MAADPARLLSSLDVLRDPEHAQLEALGNTAVLTRTPGPAVSVPELFATQVARAPQDVALV 480

MapK10 481 CEGRSLTYRQLDEASNRLAHLLAGLGAGPGQSVALLFSRSAEAVASILAVLKTGAAYLPI 540
            CEGRSLTYRQLDEASNRLAHLLAGLGAGPGQSVALLFSRSAEA+ +IL VLK+GAAYLPI
S397   481 CEGRSLTYRQLDEASNRLAHLLAGLGAGPGQSVALLFSRSAEAIVAILGVLKSGAAYLPI 540

MapK10 541 DPAAPETRIGFMLADAKPVAALSTAELAGRLEG-HGMTVIDVNDPRIQDRPATALPVPAA 599
            DPA P RIGFMLADA P+ A+STAELA RL G H + VIDV+DP I+ P++ALP P A
S397   541 DPALPGERIGFMLADAAPMVAISTAELAPRLHGQHDVPVIDVHDPAIEAAPSSALPPPGA 600

MapK10 600 DGVAYVIYTSGTTGVPKGVAVTHRNVTQLLGSLDAGLPPAGVWSQCHSYAFDVSVWEIFG 659
            D +AY+IYTSGTTGVPKGVAV+HRNVTQLL + D+GLP GVWSQ HS AFDVSVWEIFG
S397   601 DDIAYLIYTSGTTGVPKGVAVSHRNVTQLL-TADSGLPREGVWSQWHSLAFDVSVWEIFG 659

MapK10 660 ALLRGGRLVVVPEDVTRAPEELHDVLVNEQVSVLTQTPSAVAMLSPQGLESVSLVVVGEA 719
            ALL GGRLVV+P+ V R+P++ H +L++EQVSVL+QTPSA LSP+GLE ++LVV GEA
S397   660 ALLHGGRLVVIPDSVVRSPDDFHALLLDEQVSVLSQTPSAAGTLSPEGLEDLTLVVAGEA 719

MapK10 720 CPAEVVDRWSPGRVMVNAYGPTETTMCVAISAPLAPGMGSPPIGVPVDGAGLFVLDAWLR 779
            CPAE+VDRW+PGR M+NAYGPTETTMCVAISAPLAPGMGSPPIGVPVDGAGLFVLDAWLR
S397   720 CPAELVDRWAPGRTMINAYGPTETTMCVAISAPLAPGMGSPPIGVPVDGAGLFVLDAWLR 779

MapK10 780 PVPPGVVGELYVGGAGVACGYWRRGGLTASWFVACPFGAPGARMYRTGDLVCWRSDGQLD 839
            PVPPGVVGELYV GAGVACGYWRRGGLTAS FVACPFGAPGARMYRTGDLVCWRSDGQLD
S397   780 PVPPGVVGELYVAGAGVACGYWRRGGLTASRFVACPFGAPGARMYRTGDLVCWRSDGQLD 839

MapK10 840 YRGRADEQVKVRGYRIELGEVQAALAALDDVDQAVVIAREDRPGGKRLVGYITGTADPAE 899
            YRGRADEQVKVRGYRIELGEVQAALAALDDVDQAVVIAREDRPGGKRLVGYITGTADPAE
S397   840 YRGRADEQVKVRGYRIELGEVQAALAALDDVDQAVVIAREDRPGGKRLVGYITGTADPAE 899
```

FIG.6 (1)

```
MapK10  900 VRTALAQRLPVYMVPAAVVALDAIPLTPNGKLDTRALPTPEYTGSRYRAPSNAVEETVAG 959
            VRTALAQRLPVYMVPAAVVALDAIPLTPNGKLDTRALPTPEY+ YRAP + EE +AG
S397    900 VRTALAQRLPVYMVPAAVVALDAIPLTPNGKLDTRALPTPEYSTGEYRAPESPTEEILAG 959

MapK10  960 IYAHVLGVERVGVDDSFFDLGGDSISALQVVARARAAGLTCRPRDVFVEQTVARLARVVG 1019
            IYA VLGVERVGVD+SFFDLGGDSISA++VVARARAAGLTCRPRDVFVEQTVARLARVVG
S397    960 IYAEVLGVERVGVDESFFDLGGDSISAMRVVARARAAGLTCRPRDVFVEQTVARLARVVG 1019

MapK10 1020 SGDRAAEVADEGVGPVPPTPIMRWLQAAERAGGATDQFNQTVLVQAPAGVTETEVAIVLQ 1079
            SGDRAAEVADEGVGPVPPTPIMRWLQAAERAGGATDQFNQTVLVQAPAGVTETEVAIVLQ
S397   1020 SGDRAAEVADEGVGPVPPTPIMRWLQAAERAGGATDQFNQTVLVQAPAGVTETEVAIVLQ 1079

MapK10 1080 ALVDRHAMLRLRVTDDGADGWSFEVPEAGSVQARDCLRSVDALSDEALLAARARLNPAAG 1139
            ALVDRHAMLRLRVTDDGADGWSFEVPEAGSVQARDCLRSVDALSDEALLAARARLNPAAG
S397   1080 ALVDRHAMLRLRVTDDGADGWSFEVPEAGSVQARDCLRSVDALSDEALLAARARLNPAAG 1139

MapK10 1140 TMLAALWVEATGQLAVIIHHLAVDAVSWWILLEDLNIAWALHRAGQPVELAPAGTSFARW 1199
            TMLAALWVEATGQLAVIIHHLAVDAVSWWILLEDLNIAWALHRAGQPVELAPAGTSFARW
S397   1140 TMLAALWVEATGQLAVIIHHLAVDAVSWWILLEDLNIAWALHRAGQPVELAPAGTSFARW 1199

MapK10 1200 ARLLDEHARDPEVVGQLDRWKTVTSTPAALPAPRPDVDTYASAGRLSVELDAETTAMLLG 1259
            ARLLDEHARDPEVVGQLDRWKTVTSTPAALPAPRPDVDTYASAGRLSVELDAETTAMLLG
S397   1200 ARLLDEHARDPEVVGQLDRWKTVTSTPAALPAPRPDVDTYASAGRLSVELDAETTAMLLG 1259

MapK10 1260 EVPAAFHAGIHDILLIAFGLAWTEFLGEPGAPIGIDVEGHGRHEELGADIDLSRTVGWFT 1319
            EVPAAFHAGIHDILLIAFGLAWTEFLGEPGAPIGIDVEGHGRHEELGADIDLSRTVGWFT
S397   1260 EVPAAFHAGIHDILLIAFGLAWTEFLGEPGAPIGIDVEGHGRHEELGADIDLSRTVGWFT 1319

MapK10 1320 AKYPVSLDVAGLRWPQVAAGDPALGPVLKRAKEQLRTLPEPLTYGLLRYLNTDVDLAGAD 1379
            AKYPVSLDVAGLRWPQVAAGDPALGPVLKRAKEQLRTLPEPLTYGLLRYLNTDVDLAGAD
S397   1320 AKYPVSLDVAGLRWPQVAAGDPALGPVLKRAKEQLRTLPEPLTYGLLRYLNTDVDLAGAD 1379

MapK10 1380 PPIAFNYLGRQGAASDSAADGWRISQDMSLLGAAAAVPMPLMHAVELNAGTIDTGAGPHL 1439
            PPIAFNYLGRQGAASDSAADGWRISQDMSLLGAAAAVPMPLMHAVELNAGTIDTGAGPHL
S397   1380 PPIAFNYLGRQGAASDSAADGWRISQDMSLLGAAAAVPMPLMHAVELNAGTIDTGAGPHL 1439

MapK10 1440 HAEWTWAPSVLGAEQITRVSRLWFEALAGVCAHVRSGGGGGLTPSDIAPARLTQQQIDEL 1499
            HAEWTWAPSVLGAEQITRVSRLWFEALAGVCAHVRSGGGG LTPSDIAPARLTQQQIDEL
S397   1440 HAEWTWAPSVLGAEQITRVSRLWFEALAGVCAHVRSGGGG-LTPSDIAPARLTQQQIDEL 1498

MapK10 1500 QSRHRIADILPLTPLQQGLLFHSSTAQGNDGMDDMYAVQLDFTLTGPLDADRLREAVRTV 1559
            QSRHRIADILPLTPLQQGLLFHSSTAQGNDGMDDMYAVQLDFTLTGPLDADRLREAVRTV
S397   1499 QSRHRIADILPLTPLQQGLLFHSSTAQGNDGMDDMYAVQLDFTLTGPLDADRLREAVRTV 1558

MapK10 1560 VHRHPHLAALFCDQYDEPVQIIPADPAVEWRYVELDGTGAADADDLIEQLCAAERAAVAD 1619
            VHRHPHLAALFCDQYDEPVQIIPADPAVEWRYVELDGTGAADADDLIEQLCAAERAAVAD
S397   1559 VHRHPHLAALFCDQYDEPVQIIPADPAVEWRYVELDGTGAADADDLIEQLCAAERAAVAD 1618

MapK10 1620 LAGQPVFRTALVRTGGDRHRFVLTSHHILLDGWSLPILLREIFAGYYGQRLPAAGSYRAF 1679
            LAGQPVFRTALVRTGGDRHRFVLTSHHILLDGWSLPILLREIFAGYYGQRLPAAGSYRAF
S397   1619 LAGQPVFRTALVRTGGDRHRFVLTSHHILLDGWSLPILLREIFAGYYGQRLPAAGSYRAF 1678

MapK10 1680 LTWLAERDLDAARRAWGEVLSGFDTPTLVAPEGRLGQGRRGFEKSCVPEQTTRALGELAR 1739
            LTWLAERDLDAARRAWGEVLSGFDTPTLVAPEGRLGQGRRGFEKSCVPEQTTRALGELAR
S397   1679 LTWLAERDLDAARRAWGEVLSGFDTPTLVAPEGRLGQGRRGFEKSCVPEQTTRALGELAR 1738

MapK10 1740 SCHTTLSTVLQAAWAVVLTSLTGRHDVVFGTPRSRVGQLEVDDAEQMVGLLINTVPVRAE 1799
            SCHTTLSTVLQAAWAVVLTSLTGRHDVVFGTPRSRVGQLEVDDAEQMVGLLIN VPVRAE
S397   1739 SCHTTLSTVLQAAWAVVLTSLTGRHDVVFGTPRSRVGQLEVDDAEQMVGLLINAVPVRAE 1798
```

FIG.6 (2)

```
MapK10  1800  ITATTTTAQLLAQLQNSHNDTLEHQHLALNEIHRVTGHDQLFDTLFVYENYPIDSGMTLG  1859
              ITATTTTAQLLAQLQNSHNDTLEHQHLALNEIHRVTGHDQLFDTLFVYENYPIDSGMTLG
S397    1799  ITATTTTAQLLAQLQNSHNDTLEHQHLALNEIHRVTGHDQLFDTLFVYENYPIDSGMTLG  1858

MapK10  1860  ADGLAIAEFTNREYNHYPLTVEALPGPELGLHIEFDTDVFDTASIESLVQRLQRVLVAMS  1919
              ADGLAIAEFTNREYNHYPLTVEALPGPELGLHIEFDTDVFDTASIESLVQRLQRVLVAMS
S397    1859  ADGLAIAEFTNREYNHYPLTVEALPGPELGLHIEFDTDVFDTASIESLVQRLQRVLVAMS  1918

MapK10  1920  TDPDRRLSSLDLLDRGERELVLSTMSGAGVSAPIGVAPQLLAAAVAADPDAPAIVDGARE  1979
              TDPDRRLSSLDLLDRGERELVLSTMSGAGVSAPIGVAPQLLAAAVAADPDAPAIVDGARE
S397    1919  TDPDRRLSSLDLLDRGERELVLSTMSGAGVSAPIGVAPQLLAAAVAADPDAPAIVDGARE  1978

MapK10  1980  LSYRELDDWSTRLARKLIQHGVGPEHAAGVAIERCAELVVAWWAVTKVGGVYAPVNLDHP  2039
              LSYRELDDWSTRLARKLIQHGVGPEHAAGVAIERCAELVVAWWAVTK GGVYAPVNLD+P
S397    1979  LSYRELDDWSTRLARKLIQHGVGPEHAAGVAIERCAELVVAWWAVTKAGGVYAPVNLDYP  2038

MapK10  2040  VERIASVLDTVNAVCVLTCGTDEVAGAGPRPILRIDGLDLSGHSTEPITDADRRSPLRAD  2099
              VERIASVLDTVNAVCVLTCGTDEVAGAGPRPILRIDGLDLSGHSTEPITDADRRSPLRAD
S397    2039  VERIASVLDTVNAVCVLTCGTDEVAGAGPRPILRIDGLDLSGHSTEPITDADRRSPLRAD  2098

MapK10  2100  DTAYLIFTSGSTGVPKGVAVSHTGLLGWAAAQRELFGLGADARVLMVASPTFDASVGELL  2159
              DTAYLIFTSGSTGVPKGVAVSHTGLLGWAAAQRELFGLGADARVLMVASPTFDASVGELL
S397    2099  DTAYLIFTSGSTGVPKGVAVSHTGLLGWAAAQRELFGLGADARVLMVASPTFDASVGELL  2158

MapK10  2160  LAAGSGAALIVAPPQVYAGEALTALLHNQRVGTAILTPTVISTLDRGRLDGLHTLVAVGE  2219
              LAAGSGAALIVAPPQVYAGEALTALLHNQRVGTAILTPTVISTLDRGRLDGLHTLVAVGE
S397    2159  LAAGSGAALIVAPPQVYAGEALTALLHNQRVGTAILTPTVISTLDRGRLDGLHTLVAVGE  2218

MapK10  2220  ACLPELVDGWAPGRQMFNGYGPSETTIWVTCARLTAGHPVRIGAPIPGVCARVLDGWLKP  2279
              ACLPELVDGWAPGRQMFNGYGPSETTIWVTCARLTAGHPVRIGAPIPGVCARVLDGWLKP
S397    2219  ACLPELVDGWAPGRQMFNGYGPSETTIWVTCARLTAGHPVRIGAPIPGVCARVLDGWLKP  2278

MapK10  2280  VPVGVVGELYLSGPALGHGYLGRVDLTAERFVANPFGGPGERMYRTGDLVRWTPEGTLDY  2339
              VPVGVVGELYLSGPALGHGYLGRVDLTAERFVANPFGGPGERMYRTGDLVRWTPEGTLDY
S397    2279  VPVGVVGELYLSGPALGHGYLGRVDLTAERFVANPFGGPGERMYRTGDLVRWTPEGTLDY  2338

MapK10  2340  LGRADNQIKLRGQRIELGEIENTLLACPQVTQAAVTVQDSAAGSQLVAYVTLDHGPSDAD  2399
              LGRADNQIKLRGQRIELGEIENTLLACPQVTQAAVTVQDSAAGSQLVAYVTLDHGPSDAD
S397    2339  LGRADNQIKLRGQRIELGEIENTLLACPQVTQAAVTVQDSAAGSQLVAYVTLDHGPSDAD  2398

MapK10  2400  VRHDTDDADDVAQWRHLYDDLYGADLAATFGEDFRGWNSSYTGEPIPLQEMAEWRSATVD  2459
              VRHDTDDADDVAQWRHLYDDLYGADLAATFGEDFRGWNSSYTGEPIPLQEMAEWRSATVD
S397    2399  VRHDTDDADDVAQWRHLYDDLYGADLAATFGEDFRGWNSSYTGEPIPLQEMAEWRSATVD  2458

MapK10  2460  RIMSLRPRRVLEIGAGSGLLLSQIAPRCDRYVATDFSAVAIDNLARSMEQLQLPWRDRVE  2519
              RIMSLRPRRVLEIGAGSGLLLSQIAPRCDRYVATDFSAVAIDNLARSMEQLQLPWRDRVE
S397    2459  RIMSLRPRRVLEIGAGSGLLLSQIAPRCDRYVATDFSAVAIDNLARSMEQLQLPWRDRVE  2518

MapK10  2520  LLTQPAHVTDGLPPGHFDTIVINSVVQYFPNAGYLADVIDNALELLAPGGSLFIGDVRNH  2579
              LLTQPAHVTDGLPPGHFDTIVINSVVQYFPNAGYLADVIDNALELLAPGGSLFIGDVRNH
S397    2519  LLTQPAHVTDGLPPGHFDTIVINSVVQYFPNAGYLADVIDNALELLAPGGSLFIGDVRNH  2578

MapK10  2580  ALQGAFQTGIALARGGGADAAEIRQRVRHAMLGETELLLAPEFFTNWADSRPAAAGLDIQ  2639
              ALQGAFQTGIALARGGGADAAEIRQRVRHAMLGETELLLAPEFFTNWADSRPAAAGLDIQ
S397    2579  ALQGAFQTGIALARGGGADAAEIRQRVRHAMLGETELLLAPEFFTNWADSRPAAAGLDIQ  2638

MapK10  2640  LKRGLSDNELNRYRYDVVIHKAPAPVRSVAAAPTWSWTDCTDCAGLRDQLAARRPAVVRV  2699
              LKRGLSDNELNRYRYDVVIHKAPAPVRSVAAAPTWSWTDCTDCAGLRDQLAARRPAVVRV
S397    2639  LKRGLSDNELNRYRYDVVIHKAPAPVRSVAAAPTWSWTDCTDCAGLRDQLAARRPAVVRV  2698
```

FIG.6 (3)

```
MapK10  2700  TDIPQAGVIDDVRVEAALAAGLPVADALAAAGSDTAAAVAEELHRVGEATGYRVAVTWGA  2759
              TDIPQAGVIDDVRVEAALAAGLPVADALAAAGSDTAAAVAEELHRVGEATGYRVAVTWGA
S397    2699  TDIPQAGVIDDVRVEAALAAGLPVADALAAAGSDTAAAVAEELHRVGEATGYRVAVTWGA  2758

MapK10  2760  QPGTLSAVFVQDGDQAAEPLTDLYLPPAGARQRTRHANDPRANTKIAQVRERLNAWLPEY  2819
              QPGTLSAVFVQDGDQAAEPLTDLYLPPAGARQRTRHANDPRANTKIAQVRERLNAWLPEY
S397    2759  QPGTLSAVFVQDGDQAAEPLTDLYLPPAGARQRTRHANDPRANTKIAQVRERLNAWLPEY  2818

MapK10  2820  MVPTHIVALDEFPMTTSGKLDRKALPAPDYQDADRYRAPSTAVEEILVGIYGQVLGLERV  2879
              MVPTHIVALDEFPMTTSGKLDRKALPAPDYQDADRYRAPSTAVEEILVGIYGQVLGLERV
S397    2819  MVPTHIVALDEFPMTTSGKLDRKALPAPDYQDADRYRAPSTAVEEILVGIYGQVLGLERV  2878

MapK10  2880  GVDDSFFDLGGDSLSAMRLIAAVNASLNTDLGVRTVFEAPTAAELALRVGSEADRPEPLV  2939
              GVDDSFFDLGGDSLSAMRLIAAVNASLNTDLGVRTVFEAPTAAELALRVGSEADRPEPLV
S397    2879  GVDDSFFDLGGDSLSAMRLIAAVNASLNTDLGVRTVFEAPTAAELALRVGSEADRPEPLV  2938

MapK10  2940  AGERPAVIPLSFAQTRLWFIDQFQGPSPMYNITVALRLSGRLDADALRAALADVVARHES  2999
              AGERPAVIPLSFAQTRLWFIDQFQGPSPMYNITVALRLSGRLDADALRAALADVVARHES
S397    2939  AGERPAVIPLSFAQTRLWFIDQFQGPSPMYNITVALRLSGRLDADALRAALADVVARHES  2998

MapK10  3000  LRTVFATADGTPQQVVIPADRIGFACDVVDARGWPEDRLREAMSAAARYTFDLSAESPLH  3059
              LRTVFATAD TPQQVVIPADRIGFACDVVDARGWPEDRLREAMSAAARYTFDLSAESPLH
S397    2999  LRTVFATADATPQQVVIPADRIGFACDVVDARGWPEDRLREAMSAAARYTFDLSAESPLH  3058

MapK10  3060  TELFARGDDEHVLVVAVHHIAADGWSITPFARDLGVAYASRCAGRDPDWAPLPVQYADYT  3119
              TELFARGDDEHVLVVAVHHIAADGWSITPFARDLGVAYASRCAGRDPDWAPLPVQYADYT
S397    3059  TELFARGDDEHVLVVAVHHIAADGWSITPFARDLGVAYASRCAGRDPDWAPLPVQYADYT  3118

MapK10  3120  LWQRAHLGDVDDPGSRIAAQLDFWTDALAGLPERLQLPTDRPYPAVADHRGARLAVDWPA  3179
              LWQRAHLGDVDDPGSRIAAQLDFWTDALAGLPERLQLPTDRPYPAVADHRGARLAVDWPA
S397    3119  LWQRAHLGDVDDPGSRIAAQLDFWTDALAGLPERLQLPTDRPYPAVADHRGARLAVDWPA  3178

MapK10  5290  ELQQRIGDVAHRHNATSFMVIQTALTVLLAKLGANPDVAVGFPIAGRRDPALDDLVGFFV  5349
              ELQQRIGDVAHRH+ATSFMVIQTALTVLLAKLGANPDVAVGFPIAGRRDPALDDLVGFFV
S397    3179  ELQQRIGDVAHRHDATSFMVIQTALTVLLAKLGANPDVAVGFPIAGRRDPALDDLVGFFV  3238

MapK10  5350  NTLVLRVDAAGDPSFTELLARVRTRSLEAFEHQDVPFEVLVERLNPTRSLTHHPLVQVML  5409
              NTLVLRVDAAGDPSFTELLARVRTRSLEAFEHQDVPFEVLVERLNPTRSLTHHPLVQVML
S397    3239  NTLVLRVDAAGDPSFTELLARVRTRSLEAFEHQDVPFEVLVERLNPTRSLTHHPLVQVML  3298

MapK10  5410  AWQNFAGQDTGPAAGLSLGDVEITPIPVDTHTARMDLTFSVGERWCESGEPGGIGGTVEF  5469
              AWQNFAGQDTGPAAGLSLGDVEITPIPVDTHTARMDLTFSVGERWCESGEPGGIGGTVEF
S397    3299  AWQNFAGQDTGPAAGLSLGDVEITPIPVDTHTARMDLTFSVGERWCESGEPGGIGGTVEF  3358

MapK10  5470  RTDVFDPDSIQTLIGRLRRVLEAMTDDPTQSVWSVDLLDAGEHARLDTLGNRAALTGPPP  5529
              RTDVFDPDSIQTLIGRLRRVLEAMTDDPTQSVWSVDLLDAGEHARLDTLGNRAALTGPPP
S397    3359  RTDVFDPDSIQTLIGRLRRVLEAMTDDPTQSVWSVDLLDAGEHARLDTLGNRAALTGPPP  3418

MapK10  5530  RFDSLPTLFAEQAARTPDAVALVCGGRRMTYRELDEAANRVAHLLRVGAGPGHTVALLF  5589
              RFDSLPTLFAEQAARTPDAVALVCGGRRMTYRELDEA+NR+AHLL GAGPG +VALLF
S397    3419  RFDSLPTLFAEQAARTPDAVALVCGGRRMTYRELDEASNRLAHLLAGLGAGPGQSVALLF  3478

MapK10  5590  SRSAEAIVAILGVLKSGAAYLPIDPALPGERIGFMLADAAPMVAISTAELAPRLHGQHDV  5649
              SRSAEAIVAILGVLKSGAAYLPIDPALPGERIGFMLADAAPMVAISTAELAPRLHGQHDV
S397    3479  SRSAEAIVAILGVLKSGAAYLPIDPALPGERIGFMLADAAPMVAISTAELAPRLHGQHDV  3538

MapK10  5650  PVIDVHDPAIEAAPSSALPPPGADDIAYLIYTSGTTGVPKGVAVSHRNVTQLLTADSGLP  5709
              PVIDVHDPAIEAAPSSALPPPGADDIAYLIYTSGTTGVPKGVAVSHRNVTQLLTADSGLP
S397    3539  PVIDVHDPAIEAAPSSALPPPGADDIAYLIYTSGTTGVPKGVAVSHRNVTQLLTADSGLP  3598
```

FIG.6 (4)

```
MapK10  5710  REGVWSQWHSLAFDVSVWEIFGALLHGGRLVVIPDSVVRSPDDFHALLLDEQVSVLSQTP  5769
              REGVWSQWHSLAFDVSVWEIFGALLHGGRLVVIPDSVVRSPDDFHALLLDEQVSVLSQTP
S397    3599  REGVWSQWHSLAFDVSVWEIFGALLHGGRLVVIPDSVVRSPDDFHALLLDEQVSVLSQTP  3658

MapK10  5770  SAAGTLSPEGLEDLTLVVAGEACPAELVDRWAPGRTMINAYGPTEATVYTAISAPLQPGS  5829
              SAAGTLSPEGLEDLTLVVAGEACPAELVDRWAPGRTMINAYGPTEATVYTAISAPLQPGS
S397    3659  SAAGTLSPEGLEDLTLVVAGEACPAELVDRWAPGRTMINAYGPTEATVYTAISAPLQPGS  3718

MapK10  5830  PAGVPIGFPVPGAGLFVLDESLRPVPPGVVGELYVGGAGVACGYWRRGGLTASWFVACPF  5889
              PAGVPIGFPVPGAGLFVLDESLRPVPPGVVGELYV GAGVACGYWRRGGLTAS FVACPF
S397    3719  PAGVPIGFPVPGAGLFVLDESLRPVPPGVVGELYVAGAGVACGYWRRGGLTASRFVACPF  3778

MapK10  5890  GAPGARMYRTGDLVCWRSDGQLDYRGRADEQVKVRGYRIELGEVQAALAGLDDVEQAVVI  5949
              GAPGARMYRTGDLVCWRSDGQLDYRGRADEQVKVRGYRIELGEVQAALA LDDV+QAVVI
S397    3779  GAPGARMYRTGDLVCWRSDGQLDYRGRADEQVKVRGYRIELGEVQAALAALDDVDQAVVI  3838

MapK10  5950  AREDRPGGKRLVGYITGTADPAEVRTALAQRLPVYMVPAAVVALDAIPLTPNGKLDTRAL  6009
              AREDRPGGKRLVGYITGTADPAEVRTALAQRLPVYMVPAAVVALDAIPLTPNGKLDTRAL
S397    3839  AREDRPGGKRLVGYITGTADPAEVRTALAQRLPVYMVPAAVVALDAIPLTPNGKLDTRAL  3898

MapK10  6010  PTPEYTGSRYRAPSNAVEETVAGIYAHVLGVERVGVDDSFFDLGGDSISAMRVITAINAS  6069
              PTPEYTGSRYRAPSNAVEETVAGIYAHVLGVERVGVDDSFFDLGGDSISAMRVITAINAS
S397    3899  PTPEYTGSRYRAPSNAVEETVAGIYAHVLGVERVGVDDSFFDLGGDSISAMRVITAINAS  3958

MapK10  6070  LGVELAVRTLFEAPTVASLSWRAQTDTARGGQAEEIVPVQTLKEGTGAPLFCIHAAGGLS  6129
              LGVELAVRTLFEAPTVASLSWRAQTDTARGGQAEEIVPVQTLKEGTGAPLFCIHAAGGLS
S397    3959  LGVELAVRTLFEAPTVASLSWRAQTDTARGGQAEEIVPVQTLKEGTGAPLFCIHAAGGLS  4018

MapK10  6130  WSYQVLGNHLDCPIIGIQQAEPQHAAPRSIREMAQSYADRIQETYPDGPYHLVGWSFGGV  6189
              WSYQVLGNHLDCPIIGIQQAEPQHAAPRSIREMAQSYADRIQETYPDGPYHLVGWSFGGV
S397    4019  WSYQVLGNHLDCPIIGIQQAEPQHAAPRSIREMAQSYADRIQETYPDGPYHLVGWSFGGV  4078

MapK10  6190  VAHELAIELQRRGCAIARLVLLDAQPGLDGSVTAPDAALAEQHMMEEALRSHLAAADHDQ  6249
              VAHELAIELQRRGCAIARLVLLDAQPGLDGSVTAPDAALAEQHMMEEALRSHLAAADHDQ
S397    4079  VAHELAIELQRRGCAIARLVLLDAQPGLDGSVTAPDAALAEQHMMEEALRSHLAAADHDQ  4138

MapK10  6250  PHAHRQFNQLVREAGAEGMSRHKRLFDVLFGNARNNIERSKIHEPGVFLGDVTIFSAVRD  6309
              PHAHRQFNQLVREAGAEGMSRHKRLFDVLFGNARNNIERSKIHEPGVFLGDVTIFSAVRD
S397    4139  PHAHRQFNQLVREAGAEGMSRHKRLFDVLFGNARNNIERSKIHEPGVFLGDVTIFSAVRD  4198

MapK10  6310  HEDRSAFLAENWRPYVAGDIVIHEIDCTHDEILNADVVDSYGQRLGQLLGAQRRRELTPP  6369
              HEDRSAFLAENWRPYVAGDIVIHEIDCTHDEILNADVVDSYGQRLGQLLGAQRRRELTPP
S397    4199  HEDRSAFLAENWRPYVAGDIVIHEIDCTHDEILNADVVDSYGQRLGQLLGAQRRRELTPP  4258

MapK10  6370  QRFGADPGDDEPPVR  6384
              QRFGADPGDDEPPVR
S397    4259  QRFGADPGDDEPPVR  4273
```

FIG.6 (5)

ANTIGENIC TRIPEPTIDES DERIVED FROM *MYCOBACTERIUM AVIUM* SUBSP. *PARATUBERCULOSIS* S-TYPE STRAINS, DERIVATIVES AND USES THEREOF

The present invention is directed to the diagnosis, prevention and treatment of diseases resulting from infections by *Mycobacterium avium* subsp. *paratuberculosis*.

*Mycobacterium* is a genus of Actinobacteria and includes pathogens known to cause serious diseases in mammals, including tuberculosis and leprosy.

The mycobacterial cell envelope is unique among prokaryotes in that it contains unusual lipid and carbohydrate compounds, such as lipoarabinomannan and mycolic acids. The mycomembrane, an unusual outer membrane, corresponds to the permeability barrier of which inner leaflet is formed by a parallel arrangement of mycolic acids covalently linked to parietal backbone. Mycolic acids are the main components of this mycomembrane and constitute up to 60% of the lipid content of the cell wall. The outer-most layers of the cell envelope, or capsule, are composed of several types of glycolipids embedded in the saccharidic matrix surrounding the bacillus. The three major classes of type- or species-specific glycolipids include the lipooligosaccharides, phenolic glycolipids and glycopeptidolipids (GPLs). It is not clear why different lipids exist among these species of mycobacteria, but these differences have been exploited to catalog and distinguish species in this genus. Rapid growing mycobacteria, including *M. chelonae, M. scrofulaceum, M. abscessus*, and slow growing mycobacteria such as *M. avium* subsp. *avium* produce GPLs in their cell envelope (Ripoll et al., 2007). Recently, *M. abscessus* strains showing rough colony morphology were found to lack GPLs and the majority of these variants could be linked to a detrimental mutation in one of eight genes in the GPL locus.

*Mycobacterium avium* subsp. *paratuberculosis* (Map or MAP) infects different animals, essentially mammals, including bovine, ovine and caprine animals; the most commonly infected animals being cattle, sheep, goats. In addition to domesticated farm animals, Map also infects wild animals such as red deer, rabbits, bisons and buffalo.

Map is the causative agent of Johne's disease in cattle and other ruminants, a chronic progressive intestinal disease that is difficult to accurately diagnose, especially in the early stages of disease. One of the difficulties in the early diagnosis of Map infection is indeed that the pathogen remains latent for years without development of any clinical signs or disease. Infected but healthy animals, transmit the pathogen either in utero, through contaminated colostrum or milk, or through manure as MAP is shed from infected animals in feces, thus spreading the infection.

This problem of silent transmission has hindered efforts to control or eliminate the disease from dairy herds. Johne's disease is widely distributed on five continents and the most affected countries are in North America, Europe and Australia. According to the most recent National Animal Health Monitoring System survey (NAHMS, 2008), Johne's disease prevalence has increased to over 90% of U.S. dairy herds. Four distinct stages of disease progression have been described as silent infection, subclinical disease, clinical disease, and advanced clinical disease. The last two stages often develop after several years of infection. Typical advanced stage signs are weight loss, diarrhea, lethargy, and increased weakness. However, the economic toll on the dairy industry is the primary motivation for efforts at disease control. A United States Department of Agriculture (USDA) study estimated the loss of approximately $200 per cow each year with an overall economic loss of between $200 million to $250 million dollars annually to the U.S. dairy industry. There is no treatment to Johne's disease in cattle and the affected animals are culled when they begin to exhibit clinical signs of disease, especially decreased milk production for cows.

The accurate and early diagnosis of the disease is thus of outmost importance. In this respect, a suitable diagnostic must be able to discriminate between Map infection and infection by other *M. avium*, such as *M. avium* subsp. *avium* (Maa orMAA), and also infection by *M. bovis*, the causative agent of tuberculosis in cattle (bovine tuberculosis). Moreover, insofar as the animals positively diagnosed are culled, one important need is also to provide a diagnostic test limiting the undetermined results, i.e. those results which do not allow any decision to be made on the basis of the diagnosis result.

Recently, it has also been shown that Map is associated to Crohn's Disease (CD) in humans. CD is a gastrointestinal disorder, characterized inter alia by severe abdominal pain, diarrhea, bowel obstruction. Map is suspected to be involved in the disease process of CD or other gastrointestinal disorders.

Although the importance of Johne's disease in cattle and the potential involvement in CD, the causative mycobacteria Map is not yet entirely characterized, especially due to the difficulty in culturing the mycobacteria. Map is indeed an extremely slow-growing mycobacteria and requires fastidious culture conditions to grow.

Two lineages of Map have recently been identified, which are classified as type I/III or S-type (ovine) and type II or C-type (bovine) strains. The S-type isolates are readily distinguishable from C-type isolates inter alia based on genome sequencing studies.

There is thus a need for improved diagnostic tests to detect specifically *paratuberculosis* infection, which are simple, rapid, noninvasive, that can be performed by veterinarians or producers without expensive laboratory equipment and which limits the undetermined results. There is also a need for veterinary diagnostics that are sensitive (to detect MAP at early stages of infection) and specific (identity of MAP and not other microorganisms) to eliminate MAP from the commercial food supply especially due to its suspected involvement on CD.

Bacteriologic culture is the most accurate method of diagnosis, since it can detect infection during both the subclinical and clinical stages of disease, but it is time-consuming, requiring as many as 12 weeks of incubation, and is also labor-intensive. The intradermal skin test evaluates the delayed-type hypersensitivity reaction of an animal by injection of *M. avium* subsp. *paratuberculosis* extracts; however, problems involving antigenic cross-reactivity with other mycobacteria have limited its usefulness. Serologic tests for diagnosis of *paratuberculosis* based on mycobacterial whole-cell antigen mixtures or secreted proteins are relatively easy to perform but suffer from a lack of specificity, especially for the S-type. In tests that measure a cell-mediated host response, it has been demonstrated that young animals and uninfected cattle often respond to mycobacterial whole-cell antigen mixtures or secreted proteins in the gamma interferon test without showing any evidence of infection.

In this respect, it is noted that most of the previously known antigen-based diagnostic tests for Johne's disease used a complex mixture of antigens, many of which are highly conserved among mycobacterial species; they thus give high number of false positive reactions. Moreover, there are only around 40 genes which have been identified as exclusively present in the MAP genome in comparison to the closely related *M. avium* subsp. *avium* (Maa or MAA). Therefore, considering the high degree of similarity between MAP and MAA, specific antigens for use in diagnostic tests and vaccines for MAP-infection have been difficult to identify and considerable research has been directed towards the discovery of MAP specific antigens with potential diagnostic value.

In this search for *M. avium* subsp. *paratuberculosis*-specific antigens, the present inventors have previously discovered that all Map strains they tested produce a lipopentapeptide (L5P) instead of GPLs produced by many non-tuberculous mycobacteria such as *M. avium* subsp. *avium* (Maa). The sequence of the pentapeptide is based on Phe-Val-Ile-Phe-Ala, the lipopentapeptide L5P is produced by the non-ribosomal protein synthase (Nrp) of Map. The inventors have previously chemically synthesized L5P and shown that L5P is the target for a highly specific humoral response and that the major epitopes of the L5P are localized in the peptidyl moiety of the molecule (see also example 2 of the present experimental section). They also showed that L5P is the target for a specific humoral response in a subset of human patients with Crohn disease (CD). The L5P is thus a molecular signature of Map, opening now possibilities for the diagnosis of Map infection. This antigen has been used successfully in the serodiagnosis of Johne's disease in cattle (see inter alia WO2009/053844 and U.S. Pat. No. 8,883,173) and in T-cell assay (Holbert et al., 2015).

The inventors have however now shown that the lipopentapeptide L5P, is a signature specific to C-type Map, and is absent from S-type.

There is thus a need for improved diagnostic tests to detect *M. paratuberculosis* infection, and especially diagnostic tests specific to S-type Map. There is thus inter alia a need for an antigenic signature specific to S-type Map, as specific and sensitive as the signature recently identified by the inventors for the C-type isolates of Map. A good diagnostic antigen is ideally one that is able to be recognized by the immune cells and antibodies of MAP-affected animals, even in subclinical stages of infection, thus allowing diagnosis on the basis of humoral response and cell mediated response of infected animals.

Moreover, for the diagnosis of Map infection, either C-type or S-type, as with many other animal diseases, efforts need to be concentrated on the development of tests that can be performed by veterinarians or animal producers without expensive laboratory equipment. In this context, there is inter alia a need for tests which make use of hydrosoluble antigens, not requiring the use of solvents like methanol or ethanol.

Non-ribosomally synthesized peptides include a diverse class of important metabolites such as antibiotics. Non-ribosomal peptides (NRP) are usually 3-10 amino acids in length and are synthesized by large multi-modular enzymes called non-ribosomal-peptide synthetases (NRPSs). As the name implies, these peptides are not assembled by ribosome, but rather are RNA template and ribosomal independent to allow for maximum biological flexibility by incorporating many unique amino acids. In Map the mps1 gene encodes a NRPS with 5 modules that have been previously shown to be involved in production of the pentapeptidic moiety of the lipopentapeptide (L5P) (Biet et al., 2008).

The present inventors have now demonstrated that, depending on the strain type, Map produce different lipopeptide components. They have demonstrated by biochemical and physico-chemical analyses that typical lipopeptides from Map are different in S-type (lipotripeptide) and C-type strains (lipopentapeptide). They have inter alia found that the Map S-type produces the tripeptide H-D-Phe-N-Me-L-Val-L-Ala-OMe (SEQ ID NO:1), attached in N-terminal to a lipid moiety, namely a 20-carbon saturated fatty acid chain; this lipotripeptide will be designated L3P in the following. They have moreover demonstrated that this lipotripeptide is cell surface exposed, and have proven the immunoreactivity of this compound, as well as its capacity to induce humoral response and cell-mediated response.

In the context of the present invention, the amino-acids are designated by their usual symbols in the three-letters code; DPhe or D-Phe designates D-Phenylalanine, NMeVal or N-Me-Val designates N-methylated valine, Ala-OMe designates O-methyl esterified Alanine.

These findings of the inventors allow them to propose this tripeptide, as well as variants, derivatives and conjugates thereof as a signature of Map S-type, and the use thereof for the diagnosis or treatment of Map-associated diseases, especially Map S-type.

Moreover, the inventors have also demonstrated that specific chemical modifications to the lipopentapeptide produced by C-type strains give rise to a hydrosoluble analogue of this lipopentapeptide, having the same immunoreactivity as the natural or synthetic lipopentapeptide. These findings of the inventors allow them to propose hydrosoluble analogues of the lipotripeptide and of the lipopentapeptide Map S-type and C-type respectively.

DETAILED DESCRIPTION OF THE INVENTION

The present invention is directed to the L3P lipotripeptide and its peptidyl moiety specific to S-type strain, as well as derivatives and conjugates thereof; the invention also concerns the use of these antigens in different methods and tests for detecting Map infection, especially by detecting humoral response and cell mediated response of infected animals. The invention is also directed to a genetic signature and a MALDI-TOF (Matrix-Assisted Laser Desorption Ionization-Time Of Flight) spectrometry signature of S-type MAP.

The present inventors have also been able to identify a hydrosoluble analogue of the lipopentapeptide L5P, which is as specific as the natural L5P and thus suitable in diagnosis of Map, especially C-type Map.

According to a first aspect, the invention is directed to a tripeptide corresponding to the peptidyl moiety of the lipotripeptide specific to Map S-type, namely the tripeptide H-D-Phe-N-Methyl-L-Val-L-Ala-OMe, and to variants thereof. This tripeptide is indeed specific to S-type strains or isolates of Map as demonstrated by the inventors, and is recognized by antibodies specific to Map S-type.

The invention thus more generally concerns a tripeptide comprising a N-terminal Phenylalanine, a Valine and a C-terminal Alanine, linked by peptide bonds, and to variants thereof. The three amino acids F (Phe), V (Val) and A (Ala) may be naturally occurring amino acids, or non-canonical variants thereof.

In this respect, in a tripeptide according to the invention, the N-terminal phenylalanine residue is preferably a D-Phenylalanine. The Valine and Alanine are preferably L amino acids.

Moreover, it is preferred that the Valine be modified, namely by incorporation of an N-alkyl moiety, especially a methyl moiety, thus mimicking the natural tripeptide.

Similarly, the C-terminal Alanine is preferably O-modified, especially by incorporation of an O-alkyl ester moiety, preferably a O-methyl, thus mimicking the natural tripeptide.

The tripeptide according to the invention is thus preferably to be chosen in the group consisting in.
(a) a tripeptide of formula H-D-Phe-N-Methyl-L-Val-L-Ala-OMe (SEQ ID NO:1),
(b) a tripeptide of formula H-L-Phe-N-Methyl-L-Val-L-Ala-OMe (SEQ ID NO:2),
(c) a tripeptide of formula H-D-Phe-L-Val-L-Ala-OMe (SEQ ID NO:3);
(d) a tripeptide of formula H-D-Phe-N-Methyl-L-Val-L-Ala-OH (SEQ ID NO:4);
(e) a tripeptide of formula H-L-Phe-L-Val-L-Ala-OMe (SEQ ID NO:5);
(f) a tripeptide of formula H-D-Phe-L-Val-L-Ala-OH (SEQ ID NO:6);
(g) a tripeptide of formula H-L-Phe-N-Methyl-L-Val-L-Ala-OH (SEQ ID NO:7); and
(h) a tripeptide of formula H-L-Phe-L-Val-L-Ala-OH (SEQ ID NO:8).

The tripeptide according to the present invention is preferably a synthetic tripeptide, by opposition to a native tripeptide, namely a tripeptide which has not been synthesized by mycobacteria.

A preferred tripeptide is an isolated tripeptide, namely not part of a mycobacteria cell envelope.

The invention also provides tripeptide variants of the tripeptides defined above, namely tripeptide variants of the tripeptides (a) to (h), obtained for example by one or more of the following chemical modifications:
replacement of L-Val by D-Val, replacement of L-Ala by D-Ala, or simultaneous replacement of L-Val and L-Ala by D-Val and D-Ala;
modification of the peptidic bond or peptide backbone, inter alia via N-hydroxylation, ester linkages (α-hydroxy acids); insertion of extra methylene groups (β- and γ-amino acids); peptoids, azapeptides, oligoureas, arylamides, oligohydrazides; or a peptidomimetic of the tripeptide with modified backbone or linkage;
retro-inversion of the tripeptide sequence;
N-alkylation of the azote atom of Phe, Val and/or Ala, preferably N-methylation or N-ethylation of the Val and/or Ala, preferably of the Val;
Replacement of the —OH or —OCH$_3$ group at the C-terminus of the Alanine, by another O-alkyl moiety, preferably by O-ethyl or O-butyl;
Amidation of the C-terminus of Ala.

A tripeptide or tripeptide variant according to the invention is able to react with specific anti-Map antibodies, inter alia in Elisa tests as described in the experimental section.

"Specific anti-Map antibodies" herein refers to antibodies which are directed against antigenic determinants present in *Mycobacterium avium* subsp. *paratuberculosis* (Map) and absent in other species of mycobacteria and also absent in other subspecies of *M. avium*, i.e. said antibodies react with Map and do not cross-react with other mycobacteria. Preferably, said antibodies belong to the IgM, IgG1 or IgG2 class. It is preferred that specific anti-Map antibodies according to the invention are antibodies directed against S-type Map.

A tripeptide or tripeptide variant according to the invention is able to specifically react with specific anti-Map S-type antibodies. Specific anti-Map S-type antibodies are for example antibodies found in the serum of animals infected by Map S-type, which do not cross react with antigens of other mycobacteria, especially do not cross react with antigens of Maa and *M. bovis*. Cross-reaction with antibodies specific to Map C-type is however expected, due to the similar structure of L5P, characterizing C-type strains, and of L3P, characterizing the S-type strains. Specifically, a tripeptide or tripeptide variant according to the invention reacts with the same antibodies as those recognizing natural or synthetic L3P disclosed in this invention and in the experimental section.

In place or in addition to the above-mentioned modifications, the invention also concerns a tripeptide conjugate, consisting or comprising a tripeptide or tripeptide variant as disclosed above, further modified by:

addition of a non-peptide protecting or capping moiety at the N-terminus, at the C-terminus, or simultaneously at the N- and C-terminus,
N-acylation of the N-terminal Phe, preferably N-acetylation, inter alia N-acylation with a $C_1$ to $C_{30}$ acyl moiety, which is not a fatty acid moiety,
glycosylation, biotinylation, labeling, including labeling by a fluorophore, conjugation to a protein carrier, derivatization with a bi-functional spacer arm for further conjugation (either in liquid phase or on a solid support);
N-acylation of the N-terminal Phe with a $C_1$ to $C_{30}$ aliphatic acyl moiety, most preferably a $C_{10}$ to $C_{28}$ fatty acid moiety, and even most preferably with a $C_{18}$-$C_{22}$ saturated or unsaturated fatty acid moiety.

A preferred conjugate of the present invention is obtained by N-acylation of the N-terminal Phe by a lipid, preferably a saturated or unsaturated fatty acid moiety, thus giving rise to a lipotripeptide. A preferred $C_{10}$ to $C_{28}$ fatty acid moiety is a $C_{10}$ to $C_{28}$ saturated or unsaturated fatty acid moiety, preferably saturated fatty acid moiety, and most preferably a $C_{18}$-$C_{22}$ saturated fatty acid moiety. According to a most preferred embodiment, the terminal Phe is N-acylated with an eicosanoic acid acyl chain.

A tripeptide conjugate according to the invention is able to specifically react with specific anti-Map antibodies, inter alia in Elisa tests as described in the experimental section, and more preferably with anti-Map S-type antibodies. Specifically, a tripeptide conjugate according to the invention reacts with the same antibodies as those recognizing natural or synthetic L3P disclosed in this invention and in the experimental section.

According to a specific embodiment of the tripeptide, tripeptide variant or tripeptide conjugate as disclosed above, the methyl ester present at the C-terminus of Ala in the natural tripeptide is substituted by another alkyl ester, inter alia ethyl ester, propyl or butyl ester, or the C-terminal Ala is amidated, preferably by protein conjugation, or with a polyethylene glycol moiety. According to a preferred embodiment, the C-terminal Ala is amidated with a polyethylene glycol (PEG) moiety. Such a PEG moiety has advantageously the formula —$(CH_2)_3$—$O(CH_2CH_2O)_2$—$(CH_2)_3NHCOCH_2OCH_2COOH$, such that the C-terminus of the tripeptide, tripeptide variant or tripeptide conjugate has the formula —C(O)—NH—$(CH_2)_3$—$O(CH_2CH_2O)_2$—$(CH_2)_3NHCOCH_2OCH_2COOH$.

Alternatively, or in addition to this modification at the C-terminus, the N-terminus of the Phe may also be modified by addition of a PEG moiety, which is the same or different from the PEG moiety potentially added at the C-terminus. A particularly preferred PEG moiety has the formula X—$(CH_2CH_2O)_n$—CO—NH wherein X is an amine or alkyl moiety and n is an integer, preferably n is 1, 2, 3, 4 or 5.

A tripeptide, tripeptide variant or tripeptide conjugate according to this embodiment also, is able to specifically react with specific anti-Map antibodies, as detailed for the previous embodiments of the invention. The inventors have indeed demonstrated that the addition of the PEG moiety increases the hydrosolubility of the compound, without interfering with the ability of an oligopeptide to interact with specific antibodies, by showing in example 2, that the hydrosoluble analogue of L5P has the same immunogenicity as natural L5P; these results can be extended to the chemically related tripeptide, tripeptide variant and conjugate as disclosed.

Figure 9:
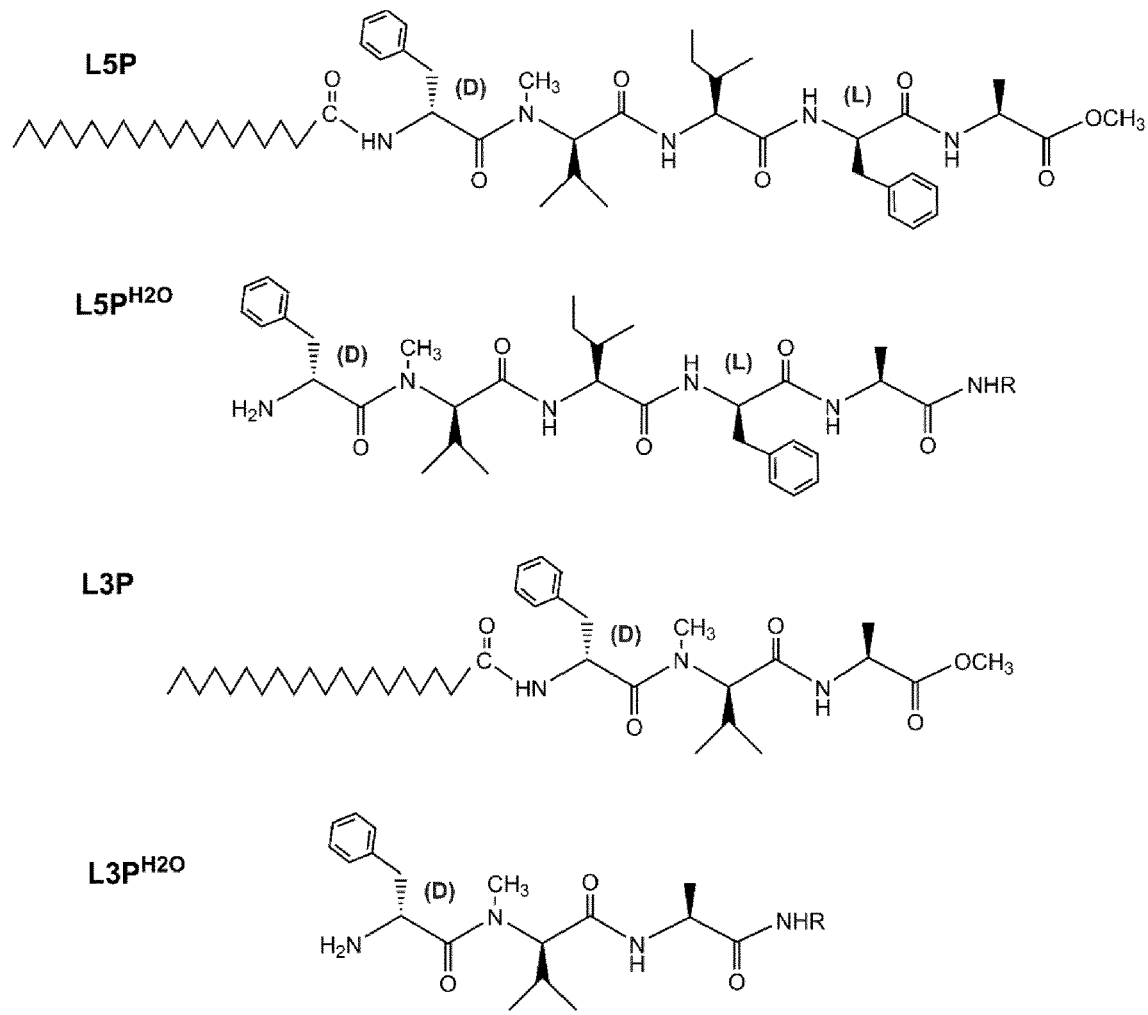

According to a more preferred embodiment, the invention is directed to a tripeptide, wherein the C-terminal Ala is amidated with a polyethylene glycol (PEG) moiety and wherein the $NH_2$ group of the N-terminal Phenylalanine is unmodified. Such a compound is illustrated in FIG. 9.

The different compounds of the invention, namely tripeptides, tripeptides variants and tripeptide conjugates can be prepared by conventional processes for synthesizing proteins, such as, for example, solid phase peptide synthesis, and classical chemistry.

If needed, the tripeptides or tripeptide variants can be labelled or coupled to a solid support. Labels and solid supports suitable for immunoassays, and methods for labelling peptides as well as for coupling them to said supports are well known to the skilled person.

According to a second aspect, the invention is directed to an antigen which is specific to *M. avium* subsp. *paratuberculosis* (Map) S-type, preferably for use in diagnosing Map infection in an animal. Such an antigen is to be chosen from the group consisting in a tripeptide or tripeptide variant of the invention, and a tripeptide conjugate of the invention, as detailed according to the first aspect of the invention. All the preferred embodiments detailed in the preceding section in connection with the first aspect of the invention are applicable to this second aspect of the invention.

The antigen of the invention is the first identified antigen which is specific to Map S-type, even if cross-reactivity with C-type is to be expected due to the close chemical structure of L3P and L5P. There is indeed no commercially available antigen specific to Map S-type. This new antigen, specific to S-type, has a thus high diagnostic value. In this respect, it is to be noted that the diagnosis of Map infection in sheep, carried out with the lipopentapeptide present in C-type, is insufficiently specific, as it gives a high number of undetermined results and false negatives (see inter alia FIG. 13).

The antigens of the invention are preferably to be used for diagnosis of Map infection in an animal susceptible to Map infection, preferably a mammal, most preferably in ovine or caprine animal. The antigen is inter alia capable of discriminating between an infection by *M. avium* subsp. *paratuberculosis* (Map) S-type and infection by Maa or *M. bovis*.

According to a third aspect, the invention is moreover relative to different methods using the specificity and sensitivity of the new antigens of the invention, namely to methods for specifically detecting the presence of Map and/or quantifying Map, especially Map S-type in a sample, methods for diagnosing Map infection, especially Map S-type infection, methods for detecting humoral immune response and cell-mediated immune response against Map, especially Map S-type. The methods are advantageously used to detect, diagnose or quantify Map S-type in a subject prone to Map S-type infection.

In one embodiment, the invention is directed to a method for the detection of specific anti-Map antibodies, or for their quantification, in a sample, comprising contacting said sample with an antigen specific to Map. The antigen to be used in this method is an antigen as described above according to the second aspect of the invention, namely an antigen chosen from the group consisting in a tripeptide or tripeptide variant of the invention, and a tripeptide conjugate of the invention, according to the first aspect of the invention. The contacting step is to be carried out under conditions allowing the formation of an antigen-antibody complex with said antigen.

The method is preferably a method for the specific detection of antibodies against S-type strains of Map. The antigen used in the method is indeed based on the tripeptide Phe-Val-Ala, which is specific to the S-type of Map and not present in C-type Map or other mycobacteria. Due to the structure similarity between the S-type tripeptide and the C-type pentapeptide, it is however expected that the method detects both anti-Map S-type antibodies and anti-Map C-type antibodies, collectively referred to as "specific anti-Map antibodies", in the sample. In any case, the method allows to accurately detect anti-Map antibodies and to specifically detect anti-Map S-type antibodies.

The detection method is advantageously to be carried out ex vivo or even preferably in vitro. According to this method, the detection of an antigen-antibody complex with the antigen of the invention is indicative of the presence of specific anti-Map antibodies and more preferably of anti-Map S-type antibodies. The antigen-antibody complex can further be quantified, in order to quantify the anti-Map antibodies, present in the sample. Such a quantification may be of importance, inter alia for differentiating animals at different stages of Map infection, e.g. for determining their infectivity level.

The method can be carried out simultaneously or sequentially with other antigens, either specific to other pathogens, for example in the context of a general sanitary control, or specific to Map C-type should it be necessary to discriminate between C-type and S-type strains. The antigen of the invention can advantageously be used in detection methods already known and inter alia in the methods disclosed in WO2009/053844.

The method of the invention can also be carried out with more than one antigen according to the invention, for example with two distinct antigens, e.g. at least one tripeptide or tripeptide variant of the invention, and at least one tripeptide conjugate, especially one lipotripeptide, namely a tripeptide conjugated to a fatty acid.

This method may also be carried out with a sample obtained from a human patient affected by Crohn's Disease, for example in order to decipher the link between Map and CD.

According to a further embodiment, the application is directed to a method for diagnosing Map infection in a subject, comprising contacting a sample obtained from said subject with an antigen according to the second aspect of the present invention.

According to this embodiment, the detection of an antigen-antibody complex with said antigen of the invention is indicative of Map infection or of a previous Map infection history, in the subject, i.e. indicative whether the subject has been infected by Map, provided that the subject has not been vaccinated against Map. This method is particularly suitable for detecting Map S-type infection, especially in animals more prone to S-type than C-type infection, like sheep and goats.

The method according to this aspect can discriminate between Map infection and *M. bovis* infection or *M. bovis* vaccination, in an animal. This feature is important, especially for cattle vaccinated against *M. bovis* infection.

The diagnostic method as described is particularly suitable for diagnosing Map infection in animals at early stages of infection, namely before the classical symptoms of Map infection arise, especially in sheep and goats. This diagnostic method may also be carried out in humans, with a view to study the link between infection by Map and CD occurrence.

As described above in the context of the detection methods, the diagnosis method of the invention can be carried out simultaneously or sequentially with additional distinct antigens, either specific to other pathogens, or specific to Map C-type. The antigen of the invention can moreover advantageously be added to the diagnosis methods already known and inter alia to the methods disclosed in WO2009/053844.

The method can also be carried out with more than one antigen according to the invention, for example with at least one tripeptide or tripeptide variant of the invention, and at least one tripeptide conjugate, especially one lipotripeptide, namely a tripeptide conjugated to a fatty acid.

According to a still further embodiment, the invention is also directed to a method for detecting humoral immune response directed against Map in a subject, comprising contacting a biological sample obtained from said subject with an antigen of the invention. This method of detecting humoral response is preferably carried out ex vivo or in vitro. The detection of an antigen-antibody complex with the antigen of the invention is indicative of humoral immune response directed against Map. The humoral response detected by this method may be either the result of Map infection, of a previous Map infection, or of Map vaccination.

This method is particularly suitable for detecting humoral immune response directed against Map S-type, especially in animals more prone to S-type than C-type infection, like sheep and goats, as the antigens is specific to Map S-type.

The method according to this aspect can discriminate between humoral immune response against Map and response against *M. bovis*.

The method as described is particularly suitable for detecting humoral immune response against Map infection in animal at early stages of infection, namely before the classical symptoms of Map infection arise, especially in sheep and goats.

As described above regarding the other methods of the invention, this method can be carried out simultaneously or sequentially with additional distinct antigens, either specific to other pathogens or specific to Map C-type. The method can also be carried out with more than one antigen according to the invention, for example with at least a tripeptide or tripeptide variant of the invention, and at least a tripeptide conjugate, especially a lipotripeptide, e.g; a tripeptide conjugated to a fatty acid.

In the different methods of the invention as described, the detection of the antigen-antibody complex is preferably carried out by ELISA (enzyme-linked immunosorbent assay), by radioimmunoassay, electrophoresis, immunofluorescence or Western Blot. The antigen of the invention, used in the methods, thus advantageously comprises any tag or chemical group aiming at facilitating the detection of the antigen-antibody complex, for example a fluorophore or an enzymatic moiety.

For the different methods of the invention which are carried out on a sample, the sample may be any appropriate biological sample obtained inter alia from a subject, preferably from an animal and more preferably from a mammal.

Appropriate sample are blood sample, serum sample, faeces sample, milk sample, lymph node biopsy, gut biopsy and urine sample. Other samples are inter alia biopsies of bowel tissues and tissue from bowel resection, especially in humans affected by Crohn's Disease. Particularly preferred samples are blood, serum, faeces and milk.

The different methods according to this third aspect of the invention are particularly advantageous in that they do not require any step of pre-adsorption of the sample with antigens of mycobacteria which are not *M. avium*, they especially do not require pre-adsorption step with antigens of *M. phlei*. The methods of the invention are thus preferably carried out without such pre-adsorption steps, as required by the commercially available diagnostic tests.

The diagnostic tests based on the host response and focused on detecting an antibody response have however some drawbacks. Early-diagnosis of MAP infection using serodiagnostic assays is sometimes hindered by the fact that affected animals can take a long time, to develop detectable serum antibody responses, at least using existing antigens. This drawback is partially overcome by the new antigens of the invention, which allow to detect serum antibody responses at an earlier stage than with previously existing antigens.

Moreover, other approaches for early diagnosis include the identification of MAP-specific antigens that detect cell mediated immune (CMI) responses such as the secretion of antigen-specific IFNγ or lymphocytes proliferation, elicited early after exposure to mycobacteria. The inventors have shown that the antigens based on the lipopeptide present in the envelope of Map are antigens that are also suitable to elicit cell mediated immune response. This point is illustrated in Holbert et al, 2015, with L5P and the results are expected to be also applicable to L3P, given the intrinsic nature of these compounds and their close chemical structure. As demonstrated in example 3 and FIG. 15, the CMI response, inter alia upregulation of T-cells proliferation, is even stronger with L3P than with L5P.

In another embodiment, the invention is thus also directed to a method for evaluating cell-mediated immune (CMI) response directed against Map in a subject, using the antigens of the invention. Preferably the cell-mediated immune response detected using the antigens of the invention is a T-cell response, and more preferably a CD25+ CD8 T cell response.

The antigen of the invention, as defined above, can indeed be used for evaluating in vitro or in vivo the T-cell immune response directed against Map, and especially against Map S-type. This can be done by the usual techniques for in vitro or in vivo detection of the cellular immune response.

For instance, a method for evaluating the T-cell immune response of a subject with respect to Map, especially Map S-type, is based on the detection of the activated T lymphocytes after incubation with the antigen of the invention, under conditions allowing the activation of the T lymphocytes present in a sample.

More specifically the invention is directed to a method for evaluating the CMI response directed against Map in a subject, comprising the steps of:
A) contacting a biological sample obtained from said subject with an antigen of the invention, and
B) detecting cytokine expression by the cells present in the biological sample or detecting lymphoproliferation.

The detection of cytokine expression or the detection of lymphoproliferation, depending on the nature of step B, is indicative of a cell immune response directed against Map in the subject.

This method of detecting CMI response is preferably carried out ex vivo or in vitro.

The method may also be carried out in vivo; in such an embodiment, the antigen of the invention is to be administered to the subject, and then the delayed-type hypersensitivity cell-mediated immune responses are detected by skin tests.

The method is particularly suitable for detecting CMI response directed against Map S-type, especially in animals more susceptible to S-type than C-type infection, like sheep and goats. As confirmed by the example 3, such a method however also allows detection of Map C-type infection.

The method according to this aspect can discriminate between CMI response against Map and response against *M. bovis*.

The cytokine expression to be detected at step B) of the method is preferably IFNγ or IL-10, and more preferably IFNγ.

The sample to be used in carrying out this method is preferably as described above for the other methods of the invention. Particularly preferred samples are blood or PBMC isolated from blood. In any of the methods disclosed above, the subject is preferably an animal more prone to Map S-type infection than Map C-type infection, especially an ovine or caprine animal, preferably sheep or goat. Given the link between Map infection and CD in human, the subject may also be a human, preferably a human affected by CD, or suspected to be infected by MAP.

As already detailed, the different methods according to the third aspect of the invention can be carried out simultaneously or sequentially with additional distinct antigens, either specific to other pathogens or specific to Map C-type, should it be necessary to discriminate between C-type and S-type strains. The methods can also be carried out with more than one antigen according to the invention, for example with at least one tripeptide or tripeptide variant of the invention, and at least one tripeptide conjugate, especially one lipotripeptide, namely a tripeptide conjugated to a fatty acid. The methods can also be carried out with at least one antigen according to the invention in combination with at least one antigen specific to C-type strains, such as a derivative or analogue of L5P as disclosed in WO2009/053844 or in the present invention, namely a hydrosoluble analogue of L5P.

All the methods as described can advantageously be carried out inter alia with samples obtained from non-symptomatic cattle.

According to a fourth aspect, the invention also concerns a composition comprising an antigen of the invention, thus specific to *M. avium* subsp. *paratuberculosis* (Map) S-type, for use as immunogenic composition. The immunogenic composition advantageously comprises additional components, in addition to the antigen of the invention. It may comprise adjuvants and/or pharmaceutically acceptable carriers. Suitable carriers are for example large macromolecules such as proteins, polysaccharides, amino acid copolymers, liposomes. Suitable adjuvants are inter alia aluminium salts, muramylpeptides, or CpG oligodeoxynucleotides. In a composition according to this aspect of the invention, the antigen to be used is preferably a tripeptide conjugate according to the 1$^{st}$ aspect of the invention, specifically conjugated to a compound known to trigger an immune response.

An immunogenic composition may also comprise additional distinct antigens, either specific to other mycobacteria or to other pathogens, or different antigens according to the invention. For example, the immunogenic composition may comprise a tripeptide, tripeptide variant or tripeptide conjugate according to the invention, in combination with at least one further antigen, for example an antigen specific to Map C-type strains, inter alia the L5P tripeptide disclosed in WO2009/053844 or a variant or derivative thereof, or an hydrosoluble analogue of L5P as disclosed in a further aspect of the present invention. The immunogenic composition may also advantageously comprise different antigens according to the invention, e.g. at least two different, or at least 3, 4 or 5 different, for example one or more tripeptide or tripeptide variant and one or more tripeptide conjugate according to the invention.

Such an immunogenic composition may be useful for immunizing a subject against Map S-type infection, especially for vaccinating a subject against Map S-type infection. When the composition comprises a combination of an antigen of the invention with an antigen based on L5P, such a composition allows the vaccination of a subject against Map infection, irrespective of the Map strain. The immunizing composition according to the invention may also be used for generating an immune response in humans, with a view to preventing Crohn's Disease, especially for generating a protective immune response.

When used as a vaccine, the immunogenic composition of the invention is preferably used as a booster dose.

The invention thus also concerns a method for vaccinating a subject against infection by Map S-type, comprising administering to said subject an immunogenic composition as disclosed above.

Such a vaccine is particularly appropriate for animals susceptible to Map S-type infection, and especially cattle, even more preferably ovine and caprine animals, such a sheep and goats.

According to still another aspect, the invention is also directed to a diagnostic kit for diagnosing *Mycobacterium avium* subsp. *paratuberculosis* (Map) infection in a subject, comprising an antigen according to the invention, and reagents for detecting an antigen-antibody complex.

Preferably such a kit also comprises controls, especially positive and negative controls, representative of presence and absence of Map infection. The diagnostic kit according to the invention is particularly suitable for diagnosing Map S-type infection, especially in animals more frequently infected by S-type than by C-type strains, especially ovine and caprine animals, such as sheep and goats. The kit may also comprise additional antigens, especially antigens specific to C-type strains, such as derivative or analogue of L5P as disclosed in WO2009/053844 or in the present invention, namely a hydrosoluble analogue of L5P. The kit may also comprise additional antigen specific to pathogens frequently infecting cattle, such as antigen specific to *M. bovis*. Such a kit may for example be a dipstick diagnostic device.

According to still another aspect, the invention is also directed to different methods for detecting the presence of *M. avium* subsp. *paratuberculosis* (Map) S-type, or determining that a tested bacterium is Map S-type, by non-immunological methods.

The present inventors have indeed analyzed the msp1 gene of S-type and C-type strains, and have shown (see example 1) that there is a deletion of around 6.3 kb in the msp1 gene of S-type strain with respect to the corresponding gene of C-type strains. This genetic difference can advantageously be used to characterize a tested bacterium as a Map S-type, or to detect the presence of Map S-strain in a sample.

The invention is thus also directed to a method for genetically determining whether a tested bacterium is Map S-strain or for detecting the presence of Map S-strain in a sample, comprising:

amplifying the genomic DNA of the tested *Mycobacterium*, or the DNA present in the sample, with the following primers:
forward primer P1 GTGCAGTACGCCGACTACAC (SEQ ID NO:10) and
reverse primer P3 ACCGGGAAAACAGCAGTG (SEQ ID NO:12), and
detecting an amplified product having a length of about 1112 bases.

The amplification step is preferably carried out by PCR. The detection is carried out by any appropriate method, well known to the skilled person. The length of the amplified product is preferably about 1112 bases, plus or minus 10%, namely between 1000 bases and 1224 bases.

It cannot be excluded that an amplified fragment of a length of about 7.4 kb be obtained. The presence of such an amplified fragment, in the absence of a fragment of about 1112 bp, is not characterizing a Map S-strain, but rather a Map C-strain.

The sample is preferably a biological sample, especially a sample as disclosed according to the other aspects of the invention.

The invention also concerns a method for genetically discriminating between a *Mycobacterium avium* subsp. *paratuberculosis* (Map) C-type and S-type, comprising:
amplifying the genomic DNA of a *Mycobacterium* with the following primers:
forward primer P1 GTGCAGTACGCCGACTACAC (SEQ ID NO:10);
reverse primer P2: AGAAACCGATCAGCTCGTCG (SEQ ID NO:11) and
reverse primer P3 ACCGGGAAAACAGCAGTG (SEQ ID NO:12).
detecting an amplified product;
wherein an amplified product of a length of about 356 bases is indicative of C-type and an amplified product of a length of about 1112 bases is indicative of S-type. The length of the amplified product characterizing the C-type strain is 356 bases, plus or minus 10%, namely between 320 bases and 392 bases.

The inventors have also demonstrated that, by analyzing a biological sample by mass spectrometry or by NMR, the presence of the lipotripeptide L3P consisting of the tripeptide H-D-Phe-N-Methyl-L-Val-L-Ala-OMe (SEQ ID NO:1), wherein the N-terminal Phenylalanine is N-acylated with an eicosanoic acid acyl chain, which is indicative of the presence of Map S-strain, gives rise to a signal characteristic of said L3P; for example a peak at a mass-to-charge ratio (m/z) of 680 atomic mass units (amu), together with extra peaks differing by 14 amu (i.e. one methylene unit) assigned to variable lengths of the fatty acid moiety, when the sample is analyzed by mass spectrometry, especially MALDI-TOF.

Such peaks are not present in sample comprising only C-type, and more generally in samples not comprising Map S-type (FIG. 1).

The invention is thus also directed to a method for detecting the presence of Map S-strain in a sample, comprising:
analyzing by mass spectrometry the sample, e.g. by MALDI-TOF;
detecting a peak at a mass-to-charge ratio (m/z) of 680 atomic mass units (amu) and potentially also peaks differing by 14 amu, inter alia 694 amu and/or 708 amu, which are as intense as 680 amu.

The detection of such a peak or peaks allows to conclude that the sample comprises Map S-type envelope, and thus is indicative of Map S-type presence or infection.

The mass spectrometry is preferably MALDI-TOF.

The sample to be used is preferably a biological sample, especially a biological sample as detailed previously. A particularly preferred biological sample according to this embodiment of the invention is a sample from lymph nodes.

When lymph nodes are used, a suitable protocol is the following: the lymph nodes frozen at −20° C. are incubated in liquid nitrogen and crushed in a mortar (diameter 15 cm) with a pestle until a fine powder is obtained. The powder thus obtained is transferred with liquid nitrogen into a 50 mL tube. The tube is then set to −20° C., unclogged, while the nitrogen evaporates and then sent under cold conditions to lipid chloroform extraction then and treated to mass analysis.

By way of contrast, the detection of a peak of 940 amu is indicative of the presence of Map C-type in the sample. The method as disclosed thus allows the rapid and specific detection of Map S-type infection, and also allows to discriminate between S-type and C-type infections.

Figure 7:
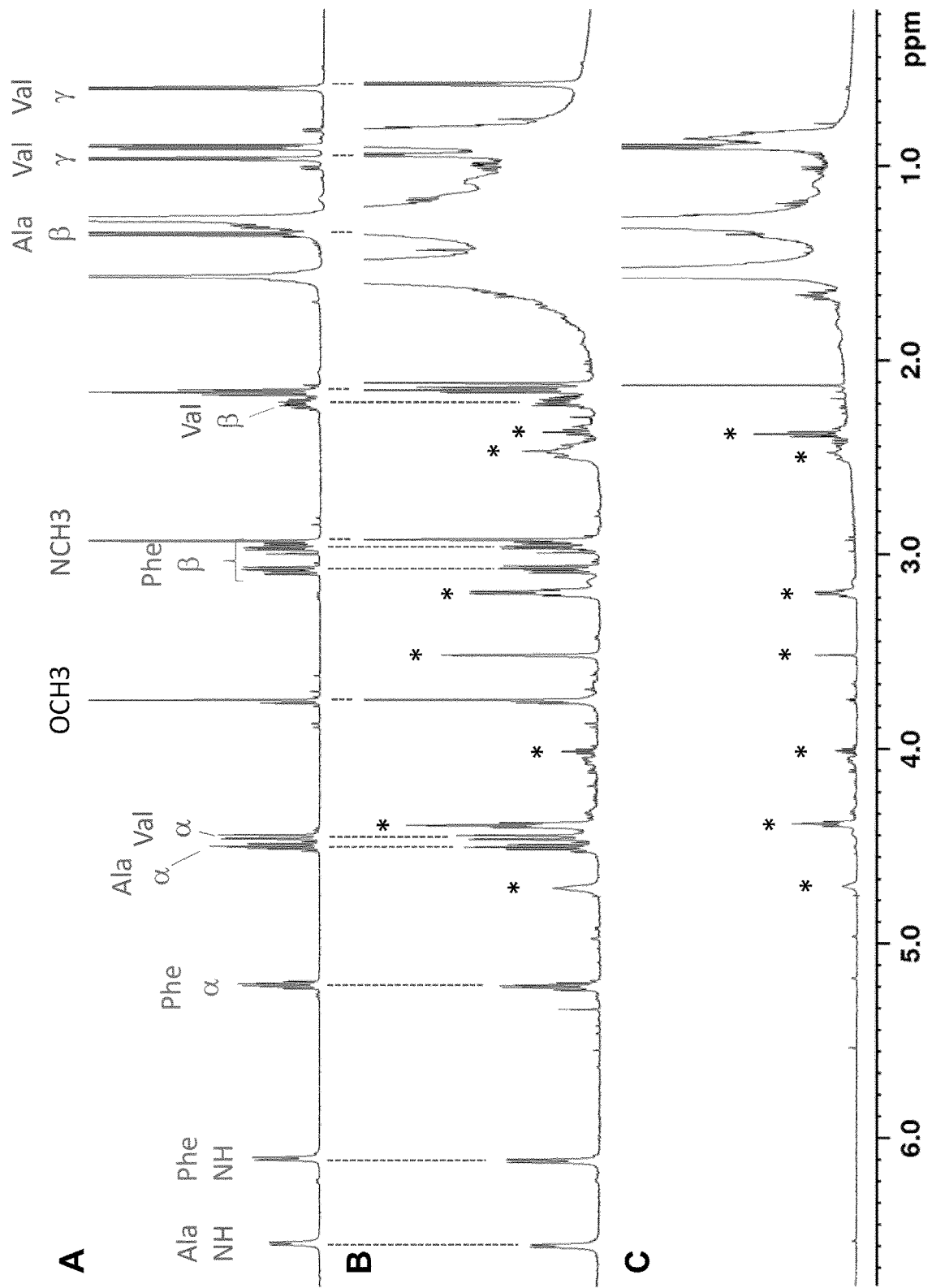

The inventors have also demonstrated, using NMR spectroscopy, the presence of L3P in a biological sample. Indeed $^1$H-NMR spectra of purified native and synthetic L3P show similar profiles with the typical signals for L3P, including peak multiplicities, coupling constants and chemical shifts (FIG. 7).

The invention is thus also directed to a method for detecting the presence of Map S-strain in a sample, comprising:
analyzing by NMR spectroscopy the sample;
detecting the typical signals of L3P as depicted in FIG. 7A, especially the main peaks as depicted in FIG. 7A.

The present inventors have also identified specific modifications of the lipopeptides of *M. avium* subsp. *paratuberculosis*, namely of the lipopentapeptide of C-strains and of the lipotripeptide of S-strains, greatly enhancing the hydrosolubility of these lipopeptides. These lipopeptides are indeed naturally not hydrosoluble, but soluble in methanol or ethanol. These solvents may prove to be difficult to manipulate, especially with a view to developing rapid and easy-to-use diagnosis kits, which can be performed by veterinarians or producers without expensive laboratory equipment. Accordingly, the invention is also directed to a pentapeptide conjugate comprising a pentapeptide core having the sequence H-Phe-Val-Ile-Phe-Ala-OH (SEQ ID NO:13), wherein the 5 amino acids are independently natural amino acids or modified amino acids, either D or L amino acids, and wherein the pentapeptide core is further modified by one or more of the following modifications:
the C-terminal Alanine is amidated with a polyethylene glycol (PEG) moiety;
the C-terminal Alanine is amidated with a PEG moiety and the N-terminal Phenylalanine is N acylated;
the N terminal Phenylalanine is modified by addition of a PEG moiety;
the C-terminal Alanine is amidated with a PEG moiety and the N-terminal Phenylalanine is modified by addition of a PEG moiety, which is identical or different to the C-terminal PEG moiety.

The pentapeptide core may advantageously have the H-D-Phe-N-Methyl-L-Val-L-Ala-O-Me (SEQ ID NO:14) and the modifications disclosed above. Such a lipopentapeptide analogue is illustrated in FIG. 9.

A particularly preferred PEG moiety according to this aspect of the invention is the PEG moiety having the formula $(CH_2)_3$—$O(CH_2CH_2O)_2$—$(CH_2)_3NHCOCH_2OCH_2COOH$.

The pentapeptide conjugates as disclosed above are hydrosoluble analogues of the lipopentapeptide disclosed in WO2009/053844. They can be used in the different diagnosis and detection methods disclosed in WO2009/053844, in place of the synthetic lipopentapeptide, which is not hydrosoluble. The pentapeptide analogues of the invention are thus advantageously used in methods for diagnosing Map infection in a subject, preferably Map C-type infection. They can also be used in the different methods disclosed in the present invention, in combination with a tripeptide, tripeptide variant or conjugate according to the invention, for example in methods aiming at discriminating C-type strains and S-type strains.

The tripeptide conjugates comprising the same modifications as detailed above for the pentapeptide conjugate, and having as peptidyl core the tripeptide according to the invention, are also within the scope of the invention.

The present invention will be further illustrated by the experimental section which follows, which refers to the identification of L3P and its study, including its specific reactivity with anti-Map antibodies, as well as the design of hydrosoluble analogues of the lipopeptide L5P. These examples are given only by way of illustration of the invention and do not constitute in any way a limitation thereof.

LEGEND OF THE FIGURES

FIG. 1: Mass spectrometry analysis of the lipids from Map. MALDI-TOF spectra of chloroform/methanol-extracted lipids from C-type Map K-10 (A), S-type Map S397 (B), purified native L3P (C) and synthetic L3P (D). The peak at 940 amu corresponds to L5P in the lipid extract of the C-type strain K-10, but is absent from the native lipids extracted from S397. The peak at 680 amu corresponds to the L3P.

Figure 2:
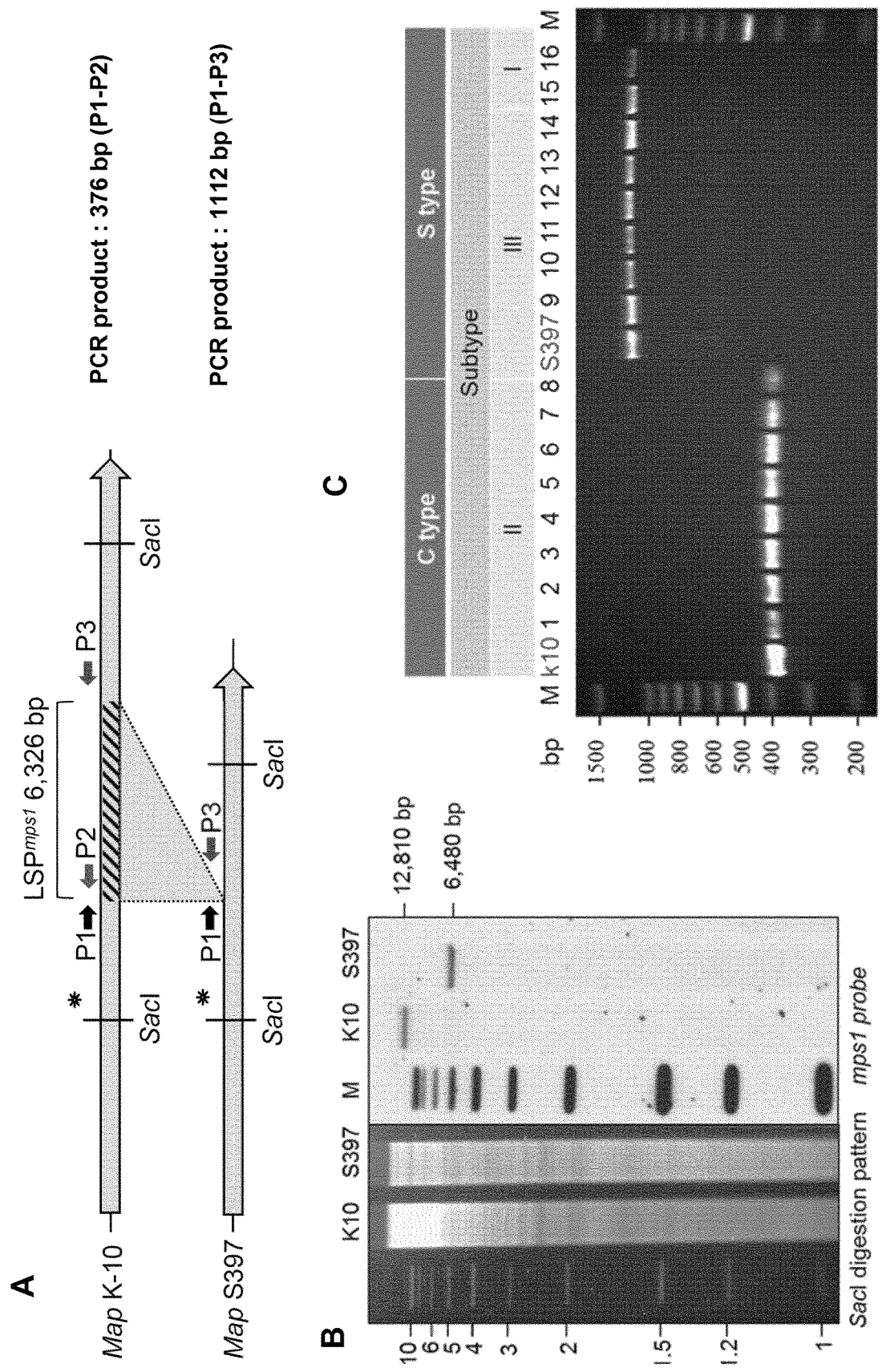

FIG. 2: DNA analysis of the mps1 deletion in the S-type strains. (A) Schematic illustration showing the mps1 coding region in K-10 and S397. The larger arrow indicates the mps1 coding sequence with the SacI sites and primer binding locations shown. The asterisk shows the location of the labeled probe used in the experiment. The shaded area represents the 6.3 kb segment that is present uniquely in the K-10 strain. The same primers were used for the experiment in panel C. (B) Agarose gel and Southern blot of SacI-digested genomic DNAs. The right half of panel B shows the respective sizes of the SacI fragment after hybridization with the labeled probe. Molecular size standards (M) are indicated in kilobase pairs in the left margin. The K-10 fragment is over 10 kb and the S397 fragment is approximately 6.5 kb. (C) Amplification products from a panel of C- and S-type Map DNAs using a three-primer amplification approach where P1 is the forward primer and P2 and P3 are the reverse primers used in a single reaction. The primers were designed such that the resulting PCR products would be of different sizes depending on the presence or absence of the $LSP^{mps1}$. This experiment was performed using a collection of 18 C-type and S-type strains previously characterized and genotyped (Biet et al., 2012). See Table 1 for details about these strains.

Figure 3:
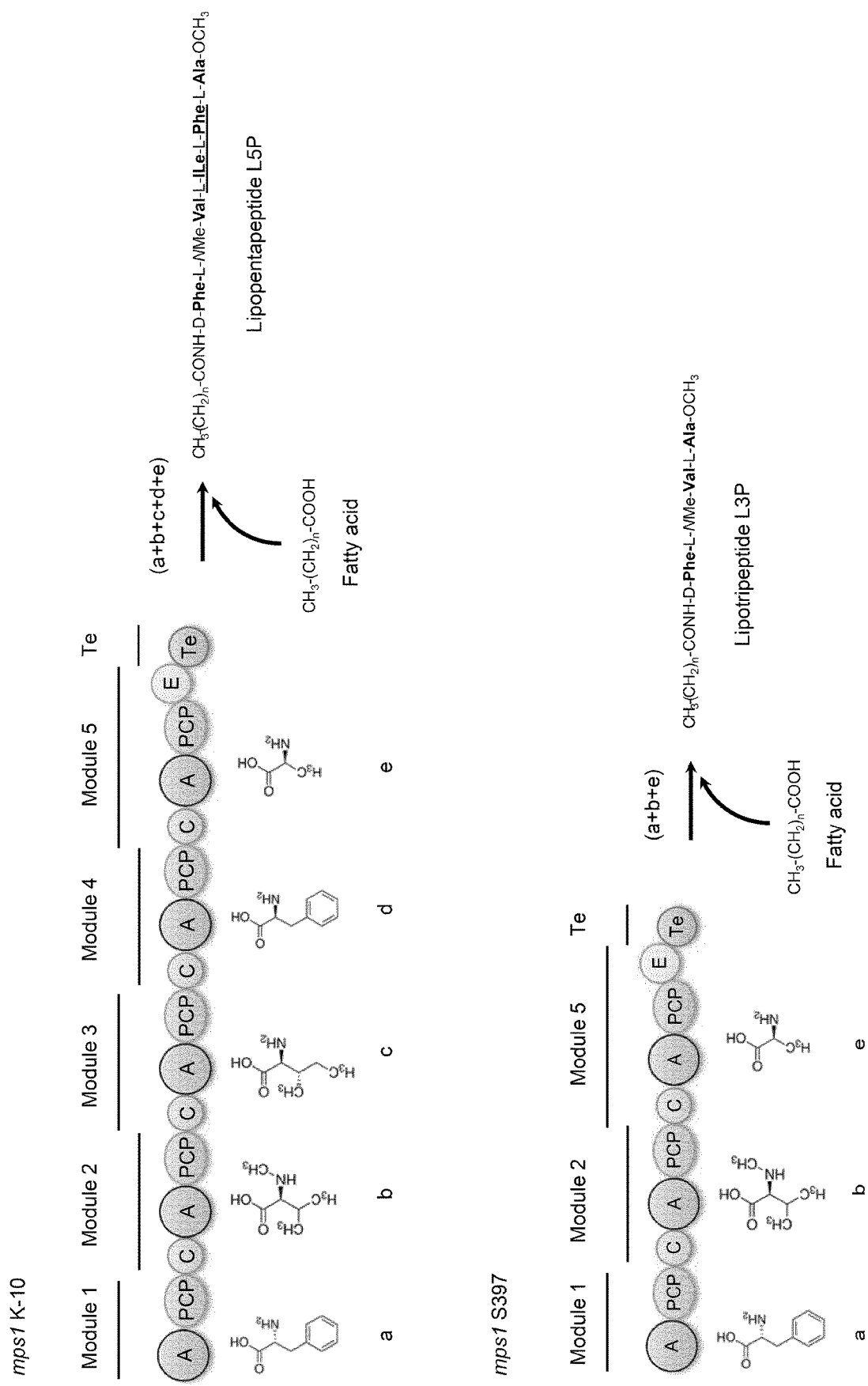

FIG. 3: Proposed model for NRP assembly of L3P and L5P in Map. Shown are the modules and domains predicted for Mps1 in K-10 and S397. Based on comparative sequence analysis, modules 3 and 4 are predicted to be absent in S397. When the 3- and 5-amino acid peptide moieties are combined with the fatty acid (n=18-20), the lipopeptide emerges. The underlined amino acids in L5P are missing in L3P. C=condensation domain; A=adenylation domain; PCP=peptidyl carrier domain; E=epimerisation domain and Te=thioesterase domain to release the full-length peptide chain.

Figure 4:
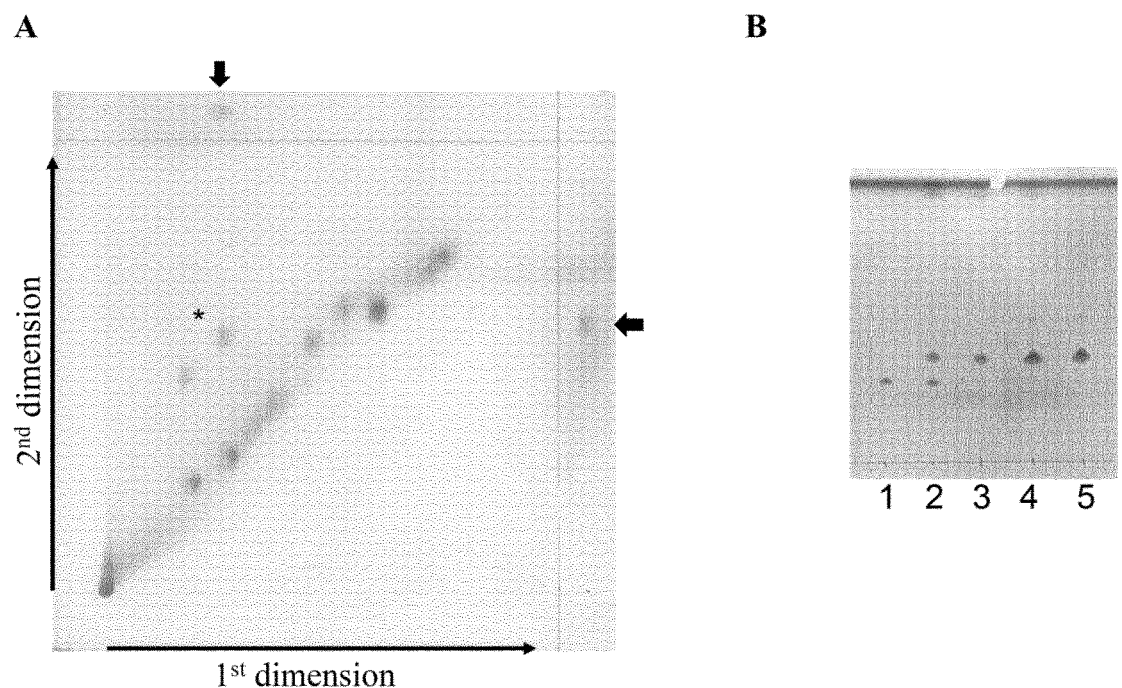

FIG. 4: S-type Map contains L3P. (A) 2-D TLC of total S397 lipids (500 µg spotted), using chloroform/methanol (96:4) as first dimension and toluene/acetone (80:20) as second dimension, and chemically synthesized L3P (15 µg) as a marker (black arrows). The asterisk indicates the position of native L3P. (B) 1-D TLC of the purified native L3P (line 3), compared to the synthetic controls L5P (line 1) and L3P (line 5) using chloroform/methanol (95:5) as the solvent system. The samples are also loaded as mixtures of the adjacent spots: synthetic L5P and purified native L3P (line 2), purified native L3P and synthetic L3P (line 4). The TLC plates were sprayed with 10% copper sulfate in 8% phosphoric acid, and lipids were visualized by heating.

Figure 5:
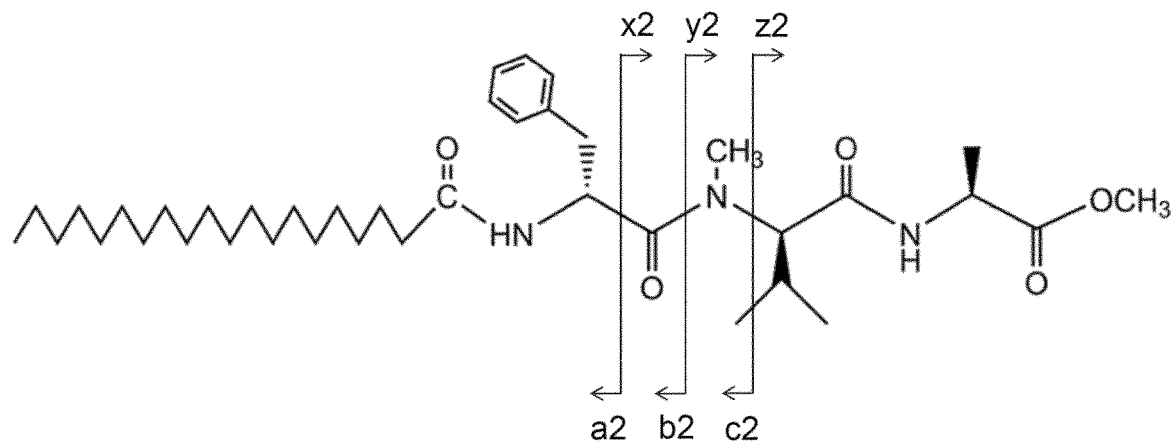

FIG. 5: Tandem MS spectra of purified native and synthetic L3P show identical fragmentation patterns. L3P purified from S397 lipids was analyzed by MALDI-TOF MS/MS and compared to synthetic L3P and L5P. Structure of L3P and typical fragmentation at the Phe-N-Methyl-Val bond. Table 2 reports the ions originating from the fragmentation at the Phe-N-Methyl-Val bond.

FIG. 6 (6-1 to 6-5): Alignment of Mps1 sequences from Map K-10 and S397. The amino acid sequences of Mps1 of K-10 (SEQ ID No: 16) was aligned with its homologue in S397 (SEQ ID No:17) by using the NCBI BLAST program with the BLOSUM64 matrix allowing gaps, Gap Costs: Existence: 11 Extension: 1, Compositional adjustments: Conditional compositional score matrix adjustment. The sequence corresponding to the LSP not present in S397, amino acids 179 to 5289 (underlined), was excluded.

The alignment statistics give 98% of identities (4175/4275), 98% of positives (4218/4275) and 0.7% of gaps (3/4275).

FIG. 7: $^1$H-NMR spectra of purified native and synthetic L3P show similar profiles. Synthetic L3P (A) and native L3P purified by preparative 2-D TLC (B) were analyzed by $^1$H-NMR and compared to a contaminant compound (C) which partially co-eluted with the native L3P (typical extra peaks indicated with an asterix).

Figure 8:
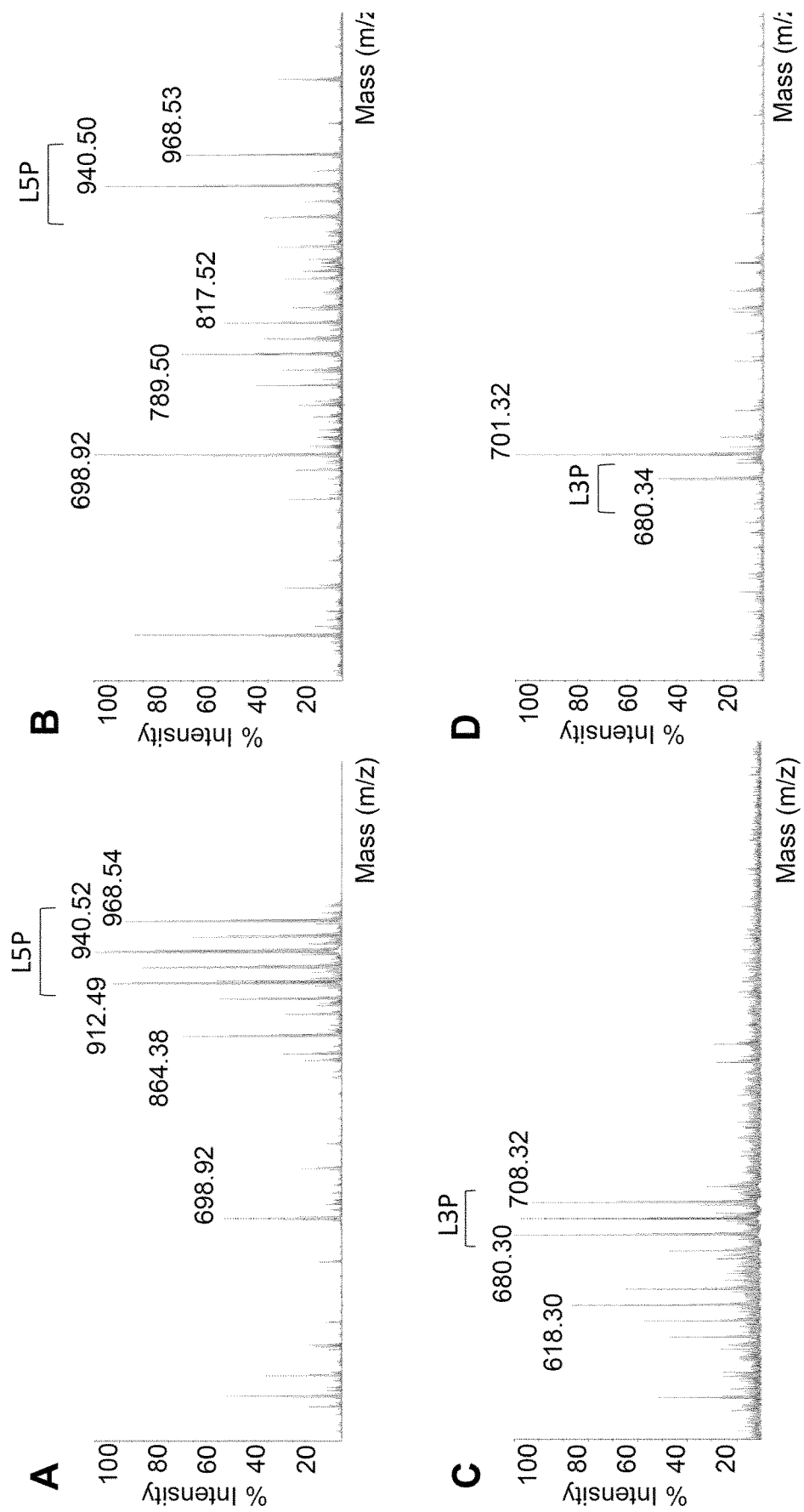

FIG. 8: The native S397 L3P and the native K-10 L5P are cell surface-exposed. MALDI-TOF spectra of cell bound (A and C) and cell surface-exposed (B and D) lipids from C-type Map K-10 (A and B), and S-type Map S397 (C and D). The peak at 940 amu corresponds to L5P in the lipid extracts of the C-type strain K-10 and the peak at 680 amu to the L3P in S-type strain S397.

FIG. 9: Structures of the lipopeptides L5P and L3P identified in *M. avium* ssp. *paratuberculosis* (Map) and of their respective L5P hydrosoluble analogues $L5P^{H2O}$, and $L3P^{H2O}$ (R=$(CH_2)_3$—$O(CH_2CH_2O)_2$—$(CH_2)_3NHCOCH_2OCH_2COOH$).

Figure 10:
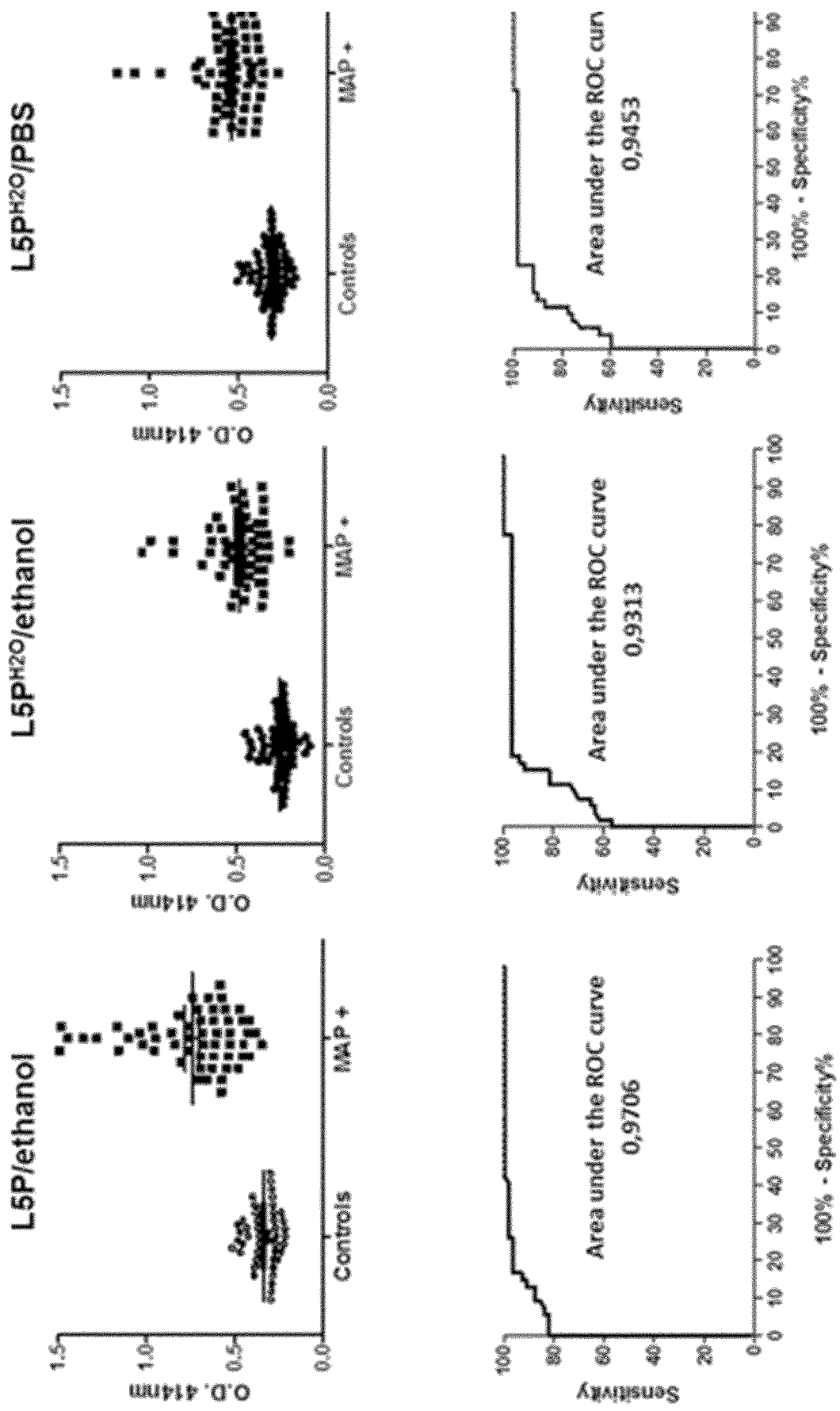

FIG. 10: Receiver operating characteristic (ROC) analysis of detection by ELISA of the antibody response against the L5P and $L5P^{H2O}$ using bovine sera. L5P is hydrophobic and solubilized in ethanol, and $L5P^{H2O}$ was used in ethanol or in PBS.

Figure 11:
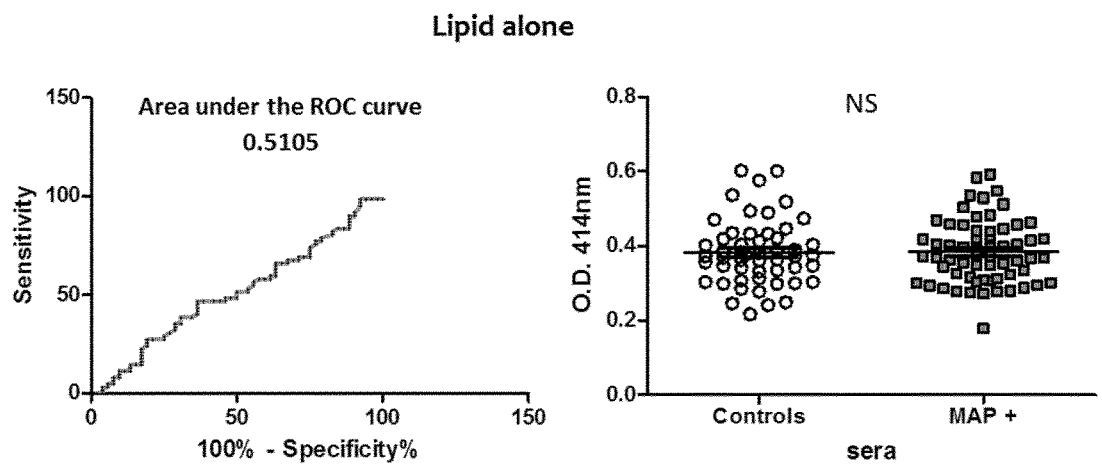

MAP+: Sera from bovine infected by Map and 53; Controls: sera from healthy bovine FIG. 11: ROC analysis of detection by ELISA of the antibody response against the lipid moiety of L5P using bovine sera. The lipid (eicosanoic acid) is hydrophobic and solubilized in ethanol.

Figure 12:
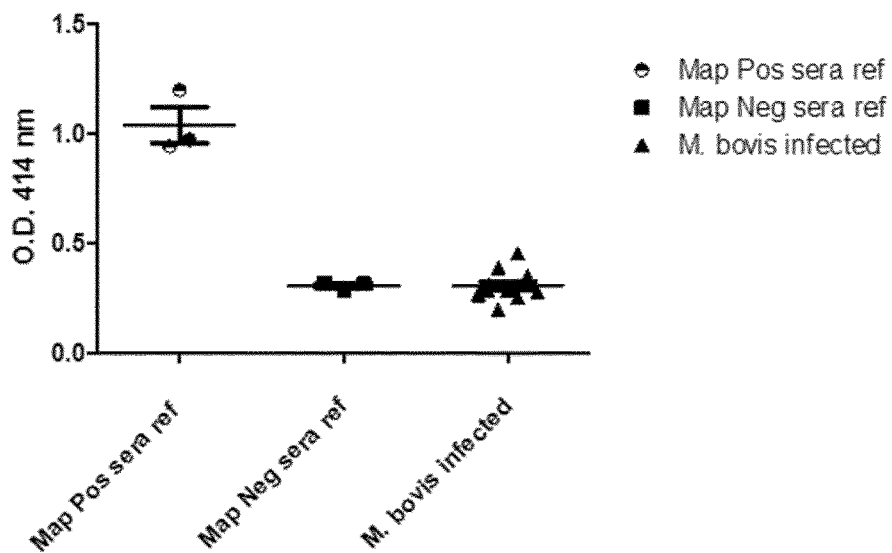

FIG. 12: Recognition of the L5P by sera of Map-infected bovines compared to *M. bovis*-infected bovines and Map-negative controls. The ELISA was performed with serial twofold dilution of reactive sera and the results are expressed as the means of triplicates.

Figure 13:
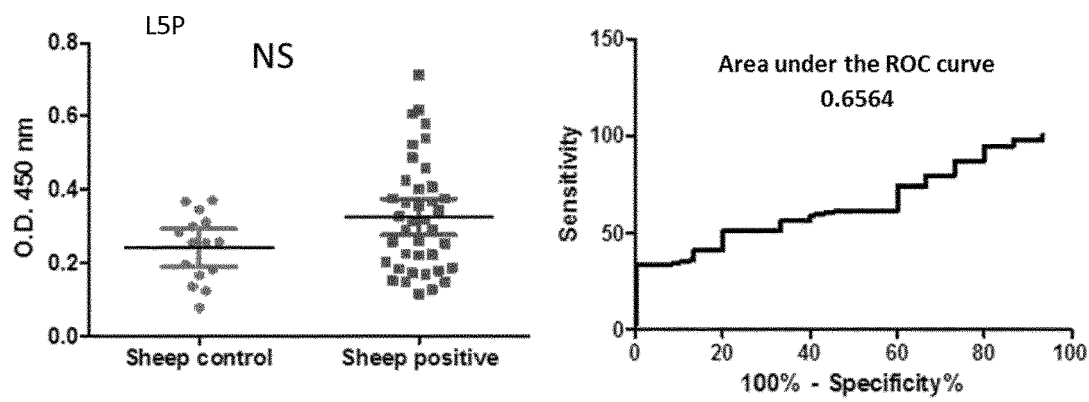

FIG. 13: Immunodetection of L5P by sheep sera naturally or experimentally infected with S-type strains of Map. (Control n=15, positive n=39)

Figure 14:
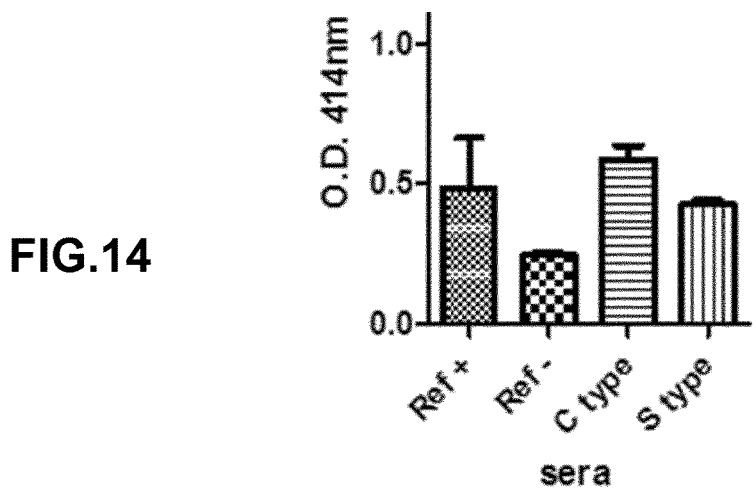

FIG. 14: ELISA recognition of L3P by bovine or sheep sera (n=3) naturally infected with C- or S-type strains of Map, respectively. Ref +; reference bovine positive serum to Map (n=3). Ref −; reference bovine negative serum to Map (n=3).

Figure 15:
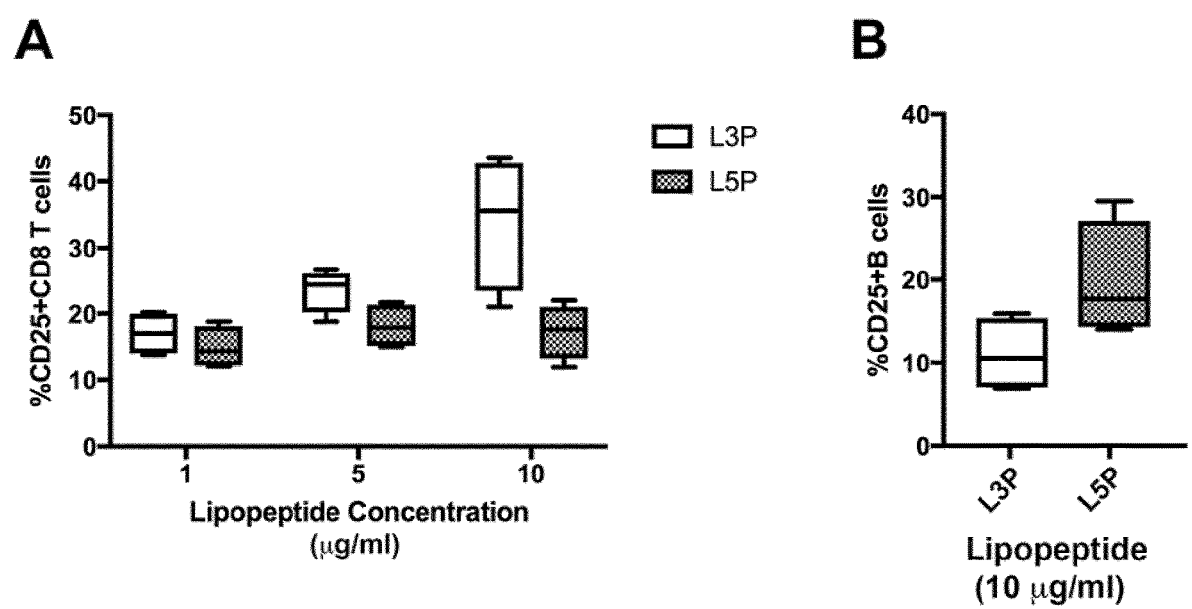

FIG. 15: T cell and B cell response to the Map lipopeptides. Proliferation of CD25+ T cells (FIG. 15A) and B cells (FIG. 15B) after culture of PBMCs isolated from cows naturally infected with Map and exposed to lipopeptides. Results are presented as percentage of CD25+ T or B cells (mean±SEM).

Figure 16:
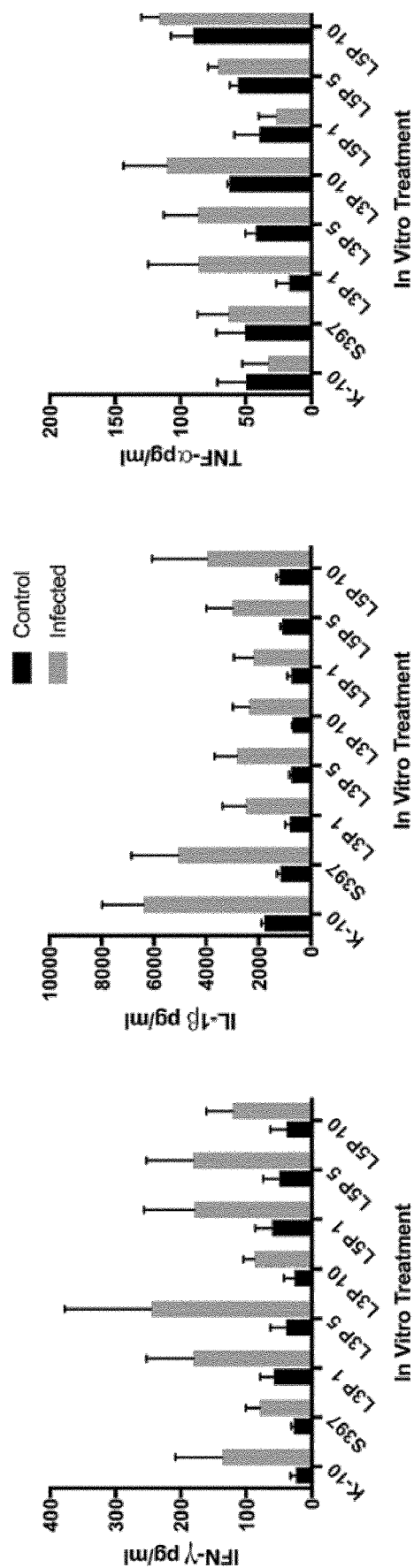

FIG. 16: Cytokine secretion by PBMCs after 24-hour stimulation with Map lipopeptides. Shown are cytokines measurements on PBMCs isolated from control cows and cows naturally infected with Map. Results are expressed as picograms/ml for IFN-γ (left), IL-1β (middle) and TNF-α (right) after stimulation with either bovine (K-10) or ovine (S397) strains of Map or lipopeptides L3P and L5P (1 µg/ml (1); 5 µg/ml (5); 10 µg/ml (10)). Histogram bars represent the mean with error bars indicating the SEM.

EXAMPLES

Example 1: Identification of Cell Wall Peptidolipid of *M. avium* subsp. *Paratuberculosis* (Map) Ovine Strain (S-Type)

Mycobacteria have a complex cell wall structure that includes many lipids; however, even within a single subspecies of *Mycobacterium avium* these lipids can differ. Total lipids from an *M. avium* subsp. *paratuberculosis* (Map) ovine strain (S-type) contained no identifiable glycopeptidolipids or lipopentapeptide, yet both lipids are present in other *M. avium* subspecies. The inventors determined the genetic and phenotypic basis for this difference using sequence analysis as well as biochemical and physicochemical approaches. This strategy showed that a nonribosomal peptide synthase, encoded by mps1, contains three amino acid specifying modules in all ovine strains analyzed, compared to five modules in bovine strains (C-type). Sequence analysis predicted these modules would produce the tripeptide Phe-N-Methyl-Val-Ala with a lipid moiety, termed lipotripeptide (L3P). Comprehensive physicochemical analysis of Map S397 extracts confirmed the structural formula of the native L3P as D-Phe-N-Methyl-L-Val-L-Ala-OMe attached in N-ter to a 20-carbon fatty acid chain. These data demonstrate that Map S-type strains, which are more adapted in sheep, produce a unique lipid. Implications for these lipid differences may include pathoevolution toward host specificity and disease presentation.

Introduction:

Map is considered as a genetically homogenous subspecies of *M. avium*, especially among bovine, human and wildlife isolates (Wu et al., 2006). However, two primary lineages have emerged following extensive phylogenetic analyses and comparative genomic studies (Biet et al., 2012). These lineages are classified as type I/III or S-type (ovine) and type II or C-type (bovine) strains. Map appears to have emerged from the common ancestor, *M. avium* subsp. *hominissuis*, to yield these two lineages. The Map C-type was first isolated from cattle and is the most commonly isolated type, while the Map S-type are typically isolated from sheep and are less prevalent. The S-type isolates are readily distinguishable from C-type isolates based on genome sequencing studies (Li et al., 2005, Bannantine et al., 2012). But these two lineages can also be readily discriminated by genotyping methods due to single nucleotide polymorphisms (Marsh et al., 1999) as well as deletions/insertions of large DNA segments (termed large sequence polymorphisms or LSP) using phylogenetic techniques such as variable number tandem repeats (Lefrancois et al., 2013), single sequence repeats (Amonsin et al., 2004, Thibault et al., 2008), representational difference analysis (Dohmann et al., 2003) and hsp65 sequencing (Turenne et al., 2006). Furthermore, genomic hybridization of S-type strains on a C-type microarray revealed a large 23-gene deletion in S-type strains (Marsh et al., 2006). However, in no case has a genetic difference been linked to a phenotypic difference between C- and S-type strains, until this study.

In addition to the genotypic distinctions between S- and C-type strains, phenotypic differences involving growth characteristics have been noted since the middle of the last century. The S-type strains are more fastidious and have slower growth rates in laboratory media than C-type strains. In contrast to C-type, the S-type strains do not grow readily on Herold's egg yolk media or Middlebrook 7H9 media that is not supplemented with egg yolk (Whittington et al., 2011). Nutrient limitation will kill S-type strains but it is only bacteriostatic for C-type (Gumber et al., 2009). Motiwala and coworkers have shown transcriptional changes in human macrophages infected with C-type, human and bison isolates, which induce an anti-inflammatory gene expression pattern, while the Map S-type isolates showed expression of pro-inflammatory cytokines (Motiwala et al., 2006), (Stevenson et al., 2002, Biet et al., 2012). Furthermore, many of the S-type strains are pigmented while C-type strains are not. On the transcriptional level, C- and S-type strains exposed to low iron or heat stress conditions had different mRNA expression patterns (Gumber & Whittington, 2009). Furthermore, iron storage in low iron conditions was only observed in the C-type but not S-type strains (Janagama et al., 2009) and virulence adhesin differences were characterized (Lefrancois et al., 2013). In this study, differences in a lipopeptide that is a component of the mycobacterial cell envelope were identified between C- and S-type strains.

Non-ribosomally synthesized peptides include a diverse class of important metabolites such as antibiotics. Nonribosomal peptides (NRP) are usually 3-10 amino acids in length and are synthesized by large multi-modular enzymes called non-ribosomal-peptide synthetases (NRPSs). These peptides are not assembled by ribosome, but rather are RNA template and ribosomal independent to allow for maximum biological flexibility by incorporating many unique amino acids. Although 10% of bacterial NRPS genes are non-modular (Wang et al., 2014), most have a modular organization where each module specifies the sequential addition of an amino acid. Several kilobases of DNA are needed for each module that consists of three domains termed the adenylation domain, peptidyl carrier domain and condensation domain. The adenylation domain binds ATP, selects its cognate amino acid building block and performs substrate acyl adenylation. Amino acid translocation occurs with the peptidyl carrier domain. The largest NRPS yet discovered is from *Photorhabdus luminescens* (WP_011146892; 16,367 aa) and contains 15 modules (Wang et al., 2014). This may represent the upper limit of NRPSs. In Map the mps1 gene encodes a NRPS with five modules that have been previously shown to be involved in production of the pentapeptidic moiety of the lipopentapeptide (L5P) (Biet et al., 2008).

The objective of this study was to identify the composition of lipopeptides in the S-type strains of Map and determine if they are different from the C-type strains.

Genetic characterization allowed the inventors to predict the production of different lipopeptide components, depending on the strain type. Synthesis of the predicted S-type lipopeptide together with thorough biochemical and physico-chemical analyses demonstrated that typical lipopeptides from Map are different in S-type (lipotripeptide) and C-type strains (lipopentapeptide). Overall, the inventors reveal key elements of Map cell wall change, involving genes and lipopeptides, occurring on the patho-evolution of the subspecies *paratuberculosis*.

Results:

The Lipid Composition Differs Between C- and S-Type Strains of Map.

A panel of genetically diverse Map strains isolated from different animal species appears similar in their lipid profiles when analyzed by thin layer chromatography (TLC) in a single dimension (1-D) (Biet et al., 2008). However, the analysis of extracted lipids from both the S397 and K-10 Map (sequenced strains characteristic of S- and C-type, respectively) revealed a striking difference by Matrix-Assisted Laser Desorption Ionization-Time Of Flight Mass Spectrometry (MALDI-TOF MS). Only the C-type strain showed a major peak at a mass-to-charge ratio (m/z) of 940 atomic mass units (amu) (FIG. 1A), which corresponds to the $[M+Na]^+$ ion of the previously characterized L5P (Riviere et al., 1996). Additional minor peaks were also observed differing by 14 amu (including a peak at m/z 968 amu), all of which are present uniquely in the C-type strain, and assigned to variable lengths of the fatty acid moiety of the L5P (Biet et al., 2008, Eckstein et al., 2006). Instead of the ion peaks at m/z 940±14 amu, the extracted lipids from the S397 strain show three major peaks at 680, 694 and 708 amu (FIG. 1B). The rest of the MS spectra were nearly identical between the two strains. These data indicate that the lipid composition of the S397 sheep strain is different from that of the C-type strains and does not include the L5P molecule.

The Mps1 Gene is Different Between C- and S-Type Strains.

A comparative genomic study was performed to determine the genetic basis for the absence of L5P in S397. While approximately 28 genes are necessary for GPL biosynthesis (Ripoll et al., 2007), the peptide core of L5P in Map is assembled by the product of a single nrps gene, termed mps1 (Biet et al., 2008). The mps1 gene of Map K-10 is also known by the locus tag MAP_1420 and has a size of 19.15 kb encoding 6,384 amino acids (Li et al., 2005). This gene is under the control of the LuxR regulator and has shown increased transcription when exposed to cow's milk (Alonso-Hearn et al., 2010). It has been suggested that the pentapeptide moiety is non-ribosomally assembled by the modules encoded by this gene (Eckstein et al., 2006), therefore, it was of interest to examine the homolog in the S-type strain. However, previous de novo whole genome assemblies of the Map S397 genome using the available Roche GS20, Roche FLX (i.e. 454), and Sanger sequence data (Bannantine et al., 2012) were unsuccessful at producing a complete assembly of the mps1 gene due to the large size and the presence of long, highly syntenic repeats in the amino-acid-specifying modules. Therefore two large sequence gaps were present in mps1 in the S-type genome.

While genome sequencing revealed that the mps1 gene is present in the S-type strain, the question of why that strain does not produce L5P remained unanswered. To address this, additional sequence data were obtained to completely assemble the region containing mps1 in the S397 genome. Surprisingly, the mps1 gene was only 12,822 bp in size compared to 19,148 bp in the K-10 genome, representing a difference of 6,326 bp. Southern blot analysis was used to confirm the 6.3 kb deletion (FIGS. 2A and 2B). By taking advantage of two SacI restriction sites that border the deletion (FIG. 2A), it was observed that the S397 SacI fragment was approximately 6 kb smaller than the corresponding fragment in K-10 (FIG. 2B).

The deletion was further characterized by PCR analysis and tested across multiple strains (Table 1). To verify that the difference in size of the mps1 gene is characteristic of all sheep strains, a PCR to detect this large sequence polymorphism ($LSP^{mps1}$) was developed based on the model described by Semret et al. (Semret et al., 2006). From the mps1 locus in K-10, three primers (P1, P2, and P3, forward primer P1 GTGCAGTACGCCGACTACAC (SEQ ID NO:10); reverse primer P2: AGAAACC-GATCAGCTCGTCG (SEQ ID NO:11) and reverse primer P3 ACCGGGAAAACAGCAGTG (SEQ ID NO:12) were designed and used in a single reaction to amplify DNA depending on the presence or absence of the 6.3 kb region (FIG. 2A). The primers were designed so that the size of the PCR product is different when using this 3-primer combination. The P1-P3 pair results in no amplification from C-type DNA due to the large distance between primers. However, P1-P2 results in successful amplification since they are only separated by 376 bp (FIG. 2C). Conversely, the P1-P2 primer combination does not work in S-type strains since P2 is located within the $LSP^{mps1}$ (FIG. 2A). However, P1-P3 does amplify S-type DNA because they are only separated by 1,112 bp due to the $LSP^{mps1}$ (FIG. 2C). Collectively, these results confirmed the boundaries of the deletion and showed it is consistent in all ten S-type strains tested including characteristic subtypes I and III.

TABLE 1

Source of strains or DNA used and their genotyping characterization

| Strain ID | Host origin | Type Subtype | Country |
|---|---|---|---|
| K10 | Bovine | C II | USA |
| S397 | Ovine | S III | USA |
| 235G | Ovine | S I | UK, Shetland |
| M189 | Ovine | S I | UK, Scotland |
| 22G | Ovine | S III | ES, Basque |
| 269OV | Ovine | S III | ES, Basque |
| FO21 | Ovine | S III | ES, Aragon |
| OVICAP16 | Caprine | S III | ES, Andalucia |
| OVICAP34 | Ovine | S III | ES, Basque |
| OVICAP49 | Ovine | S III | ES, Navarra |
| PCR311 | Caprine | S III | ES, Balearic |
| 13 | Bovine | C II | France |
| 20 | Bovine | C II | France |
| 47 | Bovine | C II | France |
| 54 | Bovine | C II | France |

TABLE 1-continued

Source of strains or DNA used and their genotyping characterization

| Strain ID | Host origin | Type Subtype | Country |
|---|---|---|---|
| 64 | Bovine | C II | France |
| 85 | Bovine | C II | France |
| 104 | Bovine | C II | France |

NRPS Encoded by Mps1 is Missing Modular Domains in the S-Type Strains.

The NRPS of mps1 is modular in its organization such that each module specifies the incorporation of one amino acid in the peptidic moiety of the lipopeptide. It became of interest to examine how the LSP$^{mps1}$ deletion might have affected lipopeptide production in the S-type strains. Using bioinformatics (Rottig et al., 2011), the functional modules and domains within each module of the NRPS were identified and this analysis established that the S-type NRPS is composed of 3 modules while the C-type has 5 modules. Furthermore, these analyses have established the nature and the position of the NRPS domains in S-type along with the domains present in C-type but missing in the S-type strain (FIG. 3). Comparison of the protein sequences corresponding to the three domains of Mps1 present in both strains shows a perfect homology suggesting a same functionality in terms of amino acid assembly (see FIG. 6).

Altogether, the sequence analysis and bioinformatic predictions of NRPS module composition identified the tripeptide Phe-Val-Ala as the antigen backbone. By analogy with the known L5P, the inventors therefore predicted that the S397 strain produces a lipotripeptide, named L3P, bearing the same structural formula as L5P but missing the two amino-acids L-Ile and L-Phe (FIG. 3).

S-Type Strains Produce a Lipid Antigen Identical to the Synthetic Lipotripeptide L3P.

To determine if S-type Map effectively produces this novel L3P antigen, the L3P molecule was chemically synthesized and compared with the native source of lipid (either the crude or the purified lipid extract from S397).

The synthetic L3P was obtained by solid-phase peptide synthesis using Fmoc chemistry and purified by chromatography on silica gel. It was then used as a control in a series of physico-chemical comparative analyses to formally identify the S-type lipid antigen.

Analysis and Purification by TLC

The analytical 2-dimensional (2-D) TLC of S397 lipid extracts shows a spot, not as prominent as L5P in C-type strains, co-migrating with the synthetic L3P (FIG. 4A). After loading a preparative 2-D TLC with 7 mg of crude extract obtained from 317 mg of cells (dry weight), the spot of interest was purified by scraping the silica gel and subsequent elution in $CH_2Cl_2$/methanol 95:5 (vol/vol). The resulting purified native antigen (approximately 50 µg) is clearly different from the C-type Map L5P, and it co-migrates with the synthetic L3P, as shown by the 1-D TLC (FIG. 4B).

Analysis by MALDI-TOF MS and MS/MS

The peak of the synthetic L3P at m/z 680 amu ([M+Na]$^+$ ion) matches that of the native antigen from the S397 strain, whether in the crude extract or in the purified lipids (FIGS. 1B, 1C and 1D). The extra peaks differing by 14 amu (i.e. one methylene unit) observed for the native antigen (FIGS. 1B and 1C) suggest the presence of different fatty acid chain lengths. In particular, the compound at m/z 708, which co-elutes with the L3P in 2-D TLC, may correspond to the L3P with a C22 acyl chain. The presumed L3P antigen is O-methylated at the C-terminus, as are the synthetic L3P and the L5P from C-type Map (Biet et al., 2008). Indeed MALDI-TOF MS of both the synthetic and native L3P compounds showed, after saponification, a down-shift of 14 amu of the molecular ion, due to the hydrolysis of the O-methyl ester group from the C-terminus (data not shown).

Additional MS/MS analysis was conducted to confirm the structure of the putative L3P compound. Importantly, the purified S397 lipid and the synthetic compound displayed identical MS/MS spectra. Probably because of the unusual structure of the lipopeptide, specifically the acylation at the N-terminus and the presence of an N-Methyl-Val residue, fragmentation of the peptide moiety of the synthetic L3P did not yield all the expected canonical couples of fragment ions, namely, the [a, b, c] ions from the N-terminus and the [x, y, z] ions from the C-terminus (FIG. 5). Nevertheless, from the parental ion m/z 680 amu, the major observed fragmentation peaks were shared between synthetic and native L3P and were totally in agreement with the structural formula of the L3P. Representative fragment ions detected and corresponding to all the possible cleavages of the peptidic bond between the Phe and the N-Methyl-Val residues are shown in Table 2. This bond has been chosen because i) it gives the most complete sampling of the various fragment ions expected after cleavage of a peptide bond (FIG. 5) and ii) it is conserved in both the L3P and L5P lipopeptides and ideally located to discriminate between these two compounds. Indeed, L3P and L5P share a common structure at the N-terminus, from the C20 fatty acid to N-Methyl-Val (FIG. 3). MS/MS analysis of the parental ions at m/z 694 and 708 amu of the native L3P variants confirmed the identity of the [a, b, c] fragment ions (N-terminal moiety of the lipopeptide with variation of 14 or 28 amu for the fragment ions, according to the variation of the length of the fatty acyl chain) and of the [x, y, z] fragment ions (invariant C-terminal moiety regardless of the length of the fatty acyl chain) (Table 2). Fewer expected fragment ions were detected with the 694 species of the L3P, probably due to the lower intensity observed with the corresponding parental ion.

Finally, MS/MS analysis of the L5P parental ion at 940 amu confirmed the assignment of these fragment ions: the [a, b, c] ions were identical between L3P and L5P, and the [x, y, z] ions increased in agreement with the presence of two additional amino acids (Table 2). Collectively, these data are consistent with an identity of structure between the purified native S397 lipid and the synthetic L3P, i.e. a tripeptide sequence Phe-N-Methyl-Val-Ala with a N-ter C20 fatty acid and a C-ter methyl ester.

TABLE 2

Ions originating from the fragmentation at the Phe-N-Methyl-Val bond.

| Antigen Source | L3P native | L3P synthetic | L3P native | L3P native | L5P synthetic |
|---|---|---|---|---|---|
| Parental ion (m/z) | 680.7 | 680.7 | 694.5 | 708.6 | 940.7 |
| Fatty acyl chain | C20 | C20 | C21 | C22 | C20 |
| a2 | 436.7 | 436.7 |  | (464.5)* | 436.5 |
| x2 | (267.3) | (267.3) |  |  | 527.4 |
| b2 | 464.6 | 464.6 | (478.4) | 492.5 | (464.5) |
| y2 | 239.5 | 239.5 | 239.3 | 239.2 | 499.4 |
| c2 | 495.7 | 495.7 |  | 523.4 | 495.5 |
| z2 | 208.3 | 208.3 | 208.2 | 208.2 | 468.4 |

*in brackets: peak of low intensity

Analysis by Nuclear Magnetic Resonance (NMR) Spectroscopy.

To confirm the structure of the native antigen, $^1$H-NMR spectroscopy was performed on the presumed L3P purified from the lipid extract of S397 cells.

Results of the NMR analysis were in agreement with the structure proposed for the native L3P. $^1$H-NMR spectra of the purified S397 lipid and the synthetic L3P are overlapping (FIGS. 7A and 7B), showing all the characteristic peaks for Phe, N-Methyl-Val and Ala, including peak multiplicities, coupling constants and chemical shifts (Table 3). The spectra revealed three resonances characteristic of the alpha protons of Phe, Val and Ala at 5.20, 4.47 and 4.50 ppm respectively. Two resonances typical of the amide region instead of three, between 6.0 and 7.0 ppm, confirm that one of the amino acids has no amide proton. The presence of a singlet at 2.92 ppm is consistent with the presence of a N-Methyl group on this amino acid.

TABLE 3

Characteristic 1H NMR data for the native purified L3P
The synthetic L3P gives similar data

| Chemical shift (ppm) | Peak multiplicity, Coupling constant | Assignment* |
|---|---|---|
| 0.61 | Doublet, J = 6.8 Hz | γ-CH$_3$ Val |
| 0.97 | Doublet, J = 6.4 Hz | γ-CH$_3$ Val |
| 1.35 | Doublet, J = 7.4 Hz | β-CH$_3$ Ala |
| 2.22 | Multiplet | β-CH Val |
| 2.92 | Singlet | N—CH$_3$ Val |
| 2.95/3.06 | 2 Doublets of doublet, J = 13.4 Hz | β-CH$_2$ Phe |
| 3.52 | Singlet | O—CH$_3$ |
| 4.47 | Doublet, J = 10.9 Hz | α-CH Val |
| 4.50 | Pentet | α-CH Ala |
| 5.20 | Multiplet | α-CH Phe |
| 6.08 | Doublet, J = 7.9 Hz | NH Phe |
| 6.52 | Doublet, J = 7.6 Hz | NH Ala |

*The assigned protons are underlined

The assignments (Table 3) were determined by the $^1$H-$^1$H-COSY NMR experiment where typical spin systems were observed for the three amino-acids.

$^1$H-NMR spectrum of the purified S397 shows additional peaks in comparison to the synthetic L3P (FIGS. 7A and 7B). These peaks may originate from distinct contaminant compound(s) which partially co-elute with the L3P during the preparative 2-D TLC. Indeed, the $^1$H-$^1$H-COSY NMR spectra show that spin systems of the extra peaks are not linked to any of the L3P peaks. Moreover, when the preparative TLC silica gel was scraped in the zone adjacent to that of L3P, the resulting eluted compound unambiguously gave a 1H-NMR spectrum displaying all the peaks that could not be attributed to L3P in the characteristic range from 2 to 5 ppm (FIG. 7C). Due to the resolution limit of the 2-D TLC and to the very low amount of native antigen, the complete purification of the antigen could not be achieved.

Nevertheless these results, together with the MS data highlighting the presence of L3P, demonstrate that the S397 strain produces a lipid content with, at least, the L3P compound.

Analysis of the Optical Purity

Finally, the optical purity of the individual amino acids within the native L3P was determined by gas chromatography coupled to MS after hydrolysis of the lipopeptide in 6N DCI in D$_2$O.

The results demonstrated the presence of the enantiomeric forms of D-Phe (91.4%), N-Methyl-L-Val (99.0%) and L-Ala (98.3%) (data not shown). Notably, in the course of this analysis, the identity of the three predicted amino acids was also confirmed based on their retention time and their mass spectra. Overall, the structure proposed for the L3P (FIG. 5) produced by S-type Map from the sequence of the mps1 gene has been confirmed: a peptidic core as D-Phe-N-Methyl-L-Val-L-Ala attached mostly to a 20-carbon fatty acid chain.

Lipopeptides are Cell Surface-Exposed

It has been assumed for a long time that L5P is localized in the cell wall of Map, but to the best of inventors' knowledge this has never been experimentally demonstrated. Analysis by MALDI-TOF MS of the lipids extracted from surface-exposed materials of Map K-10 shown that L5P is localized in the outer-most layers of the cell envelope (FIGS. 8A and 8B). Control TLC established that cord factor, a lipid which is never exposed at the mycobacterial cell surface (Ortalo-Magne et al., 1996) is indeed absent from the surface-exposed material analyzed here (data not shown), thus strengthening the inventors' conclusions.

Similarly, L3P was detected in surface-exposed materials prepared from Map S397 (FIG. 8D). MS/MS analysis of the compound at m/z 680 confirmed its identity as L3P, since all the representative fragment ions are present (data not shown). Minor amounts of cord factor were also detected in the surface extract of S397 (data not shown), suggesting a certain degree of cellular lysis for that strain. Nevertheless, the fact that the cell-bound and surface-exposed fractions displayed different lipid compositions (FIGS. 8C and 8D) suggests that L3P should be present at the cell surface of the S-type strain. But additional experiments are needed to confirm this localization. In both cases, detection of lipopeptides in the cell-bound lipidic fraction (FIGS. 8A and 8C) implies that they are also present within deeper layers of the cell-envelope.

Discussion:

In the process of characterizing the differences in lipids among C-type and S-type strains of Map, the inventors uncovered a new LSP not previously described. LSPs have been shown to distinguish Map from other *M. avium* subspecies, including *hominissuis* and *silvaticum*. In addition, three S-type-specific LSPs were characterized by genomic hybridization to DNA microarrays (Marsh et al., 2006). While these LSPs usually span several genes and range in size from 4.5 kb to over 65 kb, the LSP reported here is located exclusively within the mps1 gene and spans 6.3 kb of DNA present in C-type strains, but not in any of the S-type strains examined. It is likely that this LSP remained hidden, despite extensive genomic comparison studies, because it is entirely contained within a single gene. This newly discovered LSP now provides an additional target to distinguish S-type from C-type strains of Map.

Over 10% of the mycobacterial genome is coded for proteins involved in lipid metabolism. Large genes, including mmpL/S, pks and nrp are involved in lipid biosynthesis or transport (Ripoll et al., 2007), but the role of each of these needs to be determined by investigating genetic differences and correlating those to phenotypic differences as has been accomplished for lipooligosaccharides in *M. smegmatis*. Although numerous genetic differences between C- and S-type Map strains have been reported, the inventors' results represent the first example of a genetic difference that has been phenotypically defined. It had been previously thought that all Map strains produce L5P since only one bovine strain had been evaluated by 2-D TLC (Eckstein et al., 2006) and several other Map strains examined by 1-D TLC (Biet et al., 2008); however, 1-D TLC did not resolve differences due to limits of the technique. The difference in lipid composition was discovered only through extensive biochemical and physicochemical analysis of lipid extracts combined with detailed sequence and assembly of the large and highly repeated mps1 gene in the S-type strain.

Based on TLC analysis, Map does not produce GPLs but instead contains a lipopeptide molecule (Biet et al., 2008) initially termed Lipopeptide-I (Riviere et al., 1996) and later Para-LP-01 (Eckstein et al., 2006). This nonpolar lipid, most recently termed L5P for lipopentapeptide, is an abundant molecule in Map and is not detected in *M. avium* subsp. *avium* (Eckstein et al., 2006). It has been demonstrated that L5P is antigenic in antibody-based tests (Biet et al., 2008, Verdier et al., 2013) with minor cell-mediated immune responses, and can stimulate IFN-γ (Holbert et al., 2015). The inventors further show for the first time that L5P is clearly surface-exposed, i. e. localized in the outer-most layers of the cell envelope. The antigenicity of L3P in the S-type strains has yet to be tested, but as the L3P amino acids are conserved with that of L5P, it is unlikely that L3P will enable the specific detection of S-type Map strains.

The unique mycobacterial cell wall is important in the physiology of these bacteria and has been studied for its properties on immune stimulation and increased virulence (Howard et al., 2006, Bernut et al., 2014). Considering that L3P shares with L5P and GPLs a cell-envelope surface localization, and depending on the presence/absence of GPLs and lipopeptides described herein for a small subset of closely related mycobacteria, their physiological properties may change greatly depending on the mycobacterial strain and their evolutionary history.

NRPSs create substantial biological flexibility because no ribosomes or RNA template are needed for peptide assembly. The ribosome recognizes only 20 naturally occurring amino acids for peptide assembly; however, NRPS can specify over 500 amino acids, creating unlimited peptides for highly specialized biological functions (Walsh et al., 2013). In this study the inventors showed that the tripeptide produced in S-type strains consists of only one naturally occurring amino acid, L-Ala, and two that are "non-coded" amino acids. The C-type mps1 has five modules encoding a lipopentapeptide, but there are examples of two NRP genes, arranged in tandem, that together encode a five module NRPS to construct the antibiotic nocardicin A (Gaudelli et al., 2015). Perhaps to further increase diversity in these nonribosomal peptides, known NRPSs can be classified into three groups, linear, iterative and nonlinear. In linear NRPSs, the sequence of the resulting peptide chain is entirely determined by the number and order of the modules. Iterative NRPSs use their modules or domains more than once in the assembly of one single product. Nonlinear NRPSs involve complex scenarios with parallel nonlinear organization of domains and unusual arrangements such as internal cyclisation or incorporation of small soluble molecules. Data from this study show that mps1 for both L3P and L5P NRPSs are linear in organization.

Could the defined change in peptide length described in this study be enough to account for host preferences in C- and S-type strains of Map? S-type has a substantial host preference for sheep, but not exclusively, since S-type has also recently been isolated from several Arabian camels (Ghosh et al., 2012). However, C-type has a broader host range since it has been isolated from many ruminant species, including goat, deer and bison (Biet et al., 2012, Sibley et al., 2007). Nonetheless, there is a clear host preference or adaptation among these strains. It may be possible that this subtle change in peptide composition could define the growth rates or other phenotypic differences between these types. However, it can be excluded the fact that this NRP is responsible for pigment production reported in the S-type strains (Biet et al., 2012), since the inventors observed that L3P is colorless (data not shown). Regardless, it is clear that both lipopeptides share common epitopes since D-Phe, N-Methyl-L-Val and L-Ala are conserved in both Map types. The two amino acids missing from the S-type strain L3P are L-Ile and L-Phe. Mutational studies will confirm this point.

Rough and smooth colony appearance among *Mycobacterium* species is not only attributed to changes in their lipid composition (Wright et al., 1996) but also to virulence and drug resistance (Kansal et al., 1998, Howard et al., 2006). In fact L5P disappears when Map are cultured in cow's milk but is present in high abundance when cultured in Middlebrook 7H9 media (Alonso-Hearn et al., 2010), suggesting that the lipid profile of Map changes significantly when exposed to different environments. But there may be much more going on biologically that accounts for these lipid differences. Only recently were lipopeptides shown to interact with TLR2 receptors on key immune cells (Jimenez-Dalmaroni et al., 2015). Much research is still needed in this area to understand the biological significance of subtle lipid changes among mycobacterial species and isolates.

Materials and Methods:

Culture of S-Type Map.

S397 is an S-type strain of Map that has been previously characterized by whole genome sequencing (Bannantine et al., 2012). It was initially isolated from a Suffolk breed of sheep in Iowa in 2004. Both strains S397 and K-10 were cultured in Middlebrook 7H9 media (BD Biosciences, San Jose, Calif.) supplemented with 10% OADC, 0.05% TWEEN 80 (Polyoxyethylenesorbitan monooleate) and 2 μg/mL Mycobactin J. The culture conditions were 37° C. with no shaking in 2-liter Erlenmeyer flasks each containing 500-mL volumes of media. Milligram quantities were obtained from multiple cultures for downstream analyses.

Sequencing and Assembly of Mps1.

A combination of sequencing and assembly strategies were required to fully assemble the mps1 gene from Map S397. The large size of this gene and the presence of long repeats resulted in incomplete mps1 assembly regardless of the assembler employed (MIRA v. 3.9.9, Roche gsAssembler v. 2.6, and Velvet v. 0.7.09). Targeted de novo subassemblies of the mps1 region were created by first extracting reads that mapped to the region via MIRA's mirabait functionality using the partial contigs that aligned with MAP_1420 from K-10 and the MAP4_2425 homolog (Bannantine et al., 2014) as targets, and then de novo assembling those reads with MIRA. This was done in an iterative fashion and was supplemented as needed with additional targeted subcloning, PCR, and Sanger sequencing of the mps1 gene region until full unambiguous assembly was obtained. The GenBank accession number for mps1 in Map S397 is KP720596.

Southern Hybridization Analysis.

Mycobacteria were grown to late log phase in Middlebrook 71H9 medium (10 mL) and harvested by centrifugation at 6,000×g for 10 min. The bacteria were heat killed for 10 min at 95° C. The pellet was resuspended in 10 mL of TE buffer (10 mM Tris-HCl [pH 7.6], 1 mM EDTA) and centrifuged again at 6,000×g for 10 min. The semidried mycobacterial pellet was resuspended into 1 mL TE buffer (10 mM Tris-HCl [pH 7.6], 1 mM EDTA). After the addition of 200 μL of lysozyme (200 mg/mL) and incubation overnight at 37° C., 100 μL of SDS 10% and 50 μL Proteinase K (Macherey-Nagel) were added and incubated 4 hours at 56° C. 100 µL of 10% CTAB were mixed and incubated for 1 h at 65° C. 1 volume of phenol-chloroform-isoamyl alcohol (25:24:1 (vol/vol)) was added and the solution was vigorously mixed and then centrifuged at 14,000×g for 5 min in phase lock gel (Qiagen). The supernatant was mixed with 1 volume of chloroform-isoamyl alcohol (24:1 (vol/vol)) and centrifuged again. The DNA was precipitated by the addition of 0.8 volume of isopropanol and 0.3 M sodium acetate (final concentration). After centrifugation for 30 min at 14,000×g, the DNA was air dried, dissolved in 50 µL of TE buffer (10 mM Tris-HCl [pH 7.6], 1 mM EDTA), and stored at −20° C. until further use.

Southern blot of Map DNA was performed as previously described (Southern, 1975, van Soolingen et al., 1994) with some modifications. The mps1 DNA probe was prepared by PCR amplification of a 491-bp fragment sequence specific for Map using the primers described in this study (table 4).

PCRs were performed starting from 10 ng of chromosomal DNA of Map strain K-10 by using a TC-512 thermal cycler (Techne). The PCR product was purified on Macherey-Nagel spin columns according to the manufacturer's instructions. The probe was biotin labeled with the NEBlot Phototope kit (New England Biolabs) by following the instructions of the manufacturer. Digestion was performed with 3 µg of DNA prepared as described above and 7 U of SacI (Promega) at 37° C. for at least 6 h. Fragments were resolved by agarose gel electrophoresis and transferred onto Immobilon-S nylon membranes (Millipore) by vacuum transfer with the Vacu-Gene system (Pharmacia LKB Biotechnology). Detection of DNA fragments hybridizing with the biotinylated probe was performed with the Phototope-Star detection kit for nucleic acids (New England Biolabs), according to the manufacturer's instructions. The 2-Log DNA Ladder (New England Biolabs) was used as a molecular size marker.

TABLE 4 primer sequences:

```
Primer 1: forward primer; primers 2 and 3: reverse primers
- target: MIRU 292
Primer 1: CTTGAGCAGCTCGTAAAGCGT (SEQ ID NO:18)-
Primer 2: GCTGTATGAGGAAGTCTATTCATGG (SEQ ID NO:19)
- target: MIRU X3
Primer 1: AACGAGAGGAAGAACTAAGCCG (SEQ ID NO:20)-
Primer 2: TTACGGAGCAGGAAGGCCAGCGGG (SEQ ID NO:21)
- target: VNTR 25
Primer 1: GTCAAGGGATCGGCGAGG (SEQ ID NO:22)-
Primer 2: TGGACTTGAGCACGGTCAT (SEQ ID NO:23)
- target :VNTR 47
Primer 1: CGTTGCGATTTCTGCGTAGC (SEQ ID NO:24)-
Primer 2: GGTGATGGTCGTGGTCATCC (SEQ ID NO:25)
- target: VNTR 3
Primer 1: CATATCTGGCATGGCTCCAG (SEQ ID NO:26)-
Primer 2: ATCGTGTTGACCCCAAAGAAAT (SEQ ID NO:27)
- target: VNTR 7
Primer 1: ACAACGAAACCTACCTCGTC (SEQ ID NO:28)-
Primer 2: GTGAGCTGGCGGCCTAAC (SEQ ID NO:29)
- target: VNTR 10
Primer 1: GACGAGCAGCTGTCCGAG (SEQ ID NO:30)-
Primer 2: GAGAGCGTGGCCATCGAG (SEQ ID NO:31)
- target: VNTR 32
Primer 1: CCACAGGGTTTTTGGTGAAG (SEQ ID NO:32)-
Primer 2: GGAAATCCAACAGCAAGGAC (SEQ ID NO:33)
- target: msp1 probe
Primer 1: CGCGGCGAGCGGGAGCTGGTGC (SEQ ID NO:34)-
Primer 2: CGCAGCGGGGAGCGCCGGTCGG (SEQ ID NO:35)
- target: LSP mps1
Primer 1: GCAGTACGCCGACTACAC (nt 3-20 of SEQ ID NO:10)-
Primer 2: AGAAACCGATCAGCTCGTCG (SEQ ID NO:11)
Primer 3: ACCGGGAAAACAGCAGTG (SEQ ID NO:12)
- target: LSP A 20
Primer 1: GGCGTTACAGAATTGCCTTG (SEQ ID NO:36)-
Primer 2: GCTCGAAGTTGGAGATCAGG (SEQ ID NO:37)
Primer 3: GTACGTGGTGACCAATGTCG (SEQ ID NO:38)
- target: LSP A 4-11
Primer 1: TAGAAGGTGCGGGAAAGTTG (SEQ ID NO:39)-
Primer 2: GTCTATCTGGCGGTGCTCTC (SEQ ID NO:40)
Primer 3: GTCGAAGCAGCGTTGATTGT (SEQ ID NO:41)
- target: GyrA locus 34
Primer 1: TGTTCTTCACCACCCAGGGCCGGG (SEQ ID NO:42)-
Primer 2: TTGAGCGACAGCAGGTAGTCGTCGGCG (SEQ ID NO:43)
- target: GyrB locus 45
Primer 1: TTGGTGCGCCGCAAGAGCGCAACCG (SEQ ID NO:44)-
Primer 2: ATTTCAGCTTGTACAGCGGTGGC (SEQ ID NO:45)
```

Reference: Thibault, et al (2007) Semret et al. (2006) and Castellanos et al. (2007)

Reaction Conditions for LSP$^{mps1}$ Amplification.

A panel of Map isolates described in Table 1 was tested for the presence or absence of the large sequences identified within the genes mps1 of K-10 compared to S397. This was done with a multiplex PCR approach (Semret et al., 2006) using a set of three primers: two primers (forward and reverse) designed towards the flanking regions (bridging primers) of the LSP and a third primer designed to recognize a sequence internal to the LSP (internal primer). The primers were designed such that the resulting PCR products would be of different sizes depending on the presence or absence of the LSP understudy. Primer sequences are provided in Table 4. The PCR mixture comprised 2 µL of DNA solution added to a final volume of 25 µL containing 0.1 µL of GoTaq Flexi DNA polymerase (5 U/µL Promega), 2 mM (each) dATP, dCTP, dGTP, and dTTP (Promega); 5 µL of 5×PCR buffer supplied by the manufacturer; 1 µM of each primers; 1 µL of dimethyl sulfoxide (Sigma); 1.5 mM of $MgCl_2$ and 5 µL of 5M betaine solution (Sigma). The reactions were carried out using a TC-512 thermal cycler (Techne). PCR conditions were as follows: 1 cycle of 5 min at 94° C.; 30 cycles of 30 s at 94° C., 30 s at 62° C., and 30 s at 72° C.; and 1 cycle of 7 min at 72° C. To detect presence or absence of each LSP, PCR products were analyzed by electrophoresis using 1.5% agarose gels.

Bioinformatic Prediction of Peptide Composition from NRPS Sequence.

The peptide composition of the lipopeptides analyzed in this study were deduced from DNA sequence comparisons between K-10 and S397 strains as well as a bioinformatics approach using domain prediction software including the NCBI web tools ncbi.nlm.nih.gov/Structure/cdd/wrpsb.cgi and the web site of PKS/NRPS Analysis at nrps.igs.umary-land.edu/nrps. Peptide composition was determined using the web-based server NRPSpredictor2 (Rottig et al., 2011).

Chemical Synthesis of the Lipopeptides.

The control lipopeptides (L3P and L5P) were synthesized on solid phase using the standard Fmoc chemistry protocol, as previously described (Biet et al., 2008). After cleavage from the resin, the crude L3P product was purified on a silica gel column using $CH_2Cl_2$/methanol as eluent (from 98:2 to 97:3 (vol/vol)), and 80 mg of the lipopeptide were obtained (yield 80% based on the net peptide content). The synthetic L3P was characterized by electrospray ionization MS (Q-Tof Micro Waters), quantitative amino acid analysis (AAA) (after hydrolysis with 6N HCl at 110° C. for 48 h and using a Beckman 6300 analyzer) and NMR (Bruker 400 MHz instrument).

MS: $C_{39}H_{67}N_3O_5$ (calcd 657.5081) m/z 658.5155 $[M+H]^+$, 680.4994 $[M+Na]^+$.

AAA: Ala 1 (1), Phe 0.96 (1), and an extra peak typical of N-Methyl-Val.

$^1$H NMR ($CDC_3$): δ 0.60 (d, 3H, $CH_{3\gamma}$ Val, J=6.68 Hz), 0.90 (t, 3H, $CH_3$ lipid, J=7.05 Hz), 0.96 (d, 3H, $CH_{3\gamma}$ Val, J=6.41 Hz), 1.25-1.29 (m, 32H, 16 $CH_2$ lipid), 1.35 (d, 3H, $CH_3\beta$ Ala, J=7.21 Hz), 1.53-1.59 (m, 2H, $CH_2CH_2CO$ lipid), 2.15 (t, 3H, $CH_2CO$ lipid, J=7.60 Hz), 2.18-2.27 (m, 1H, CHβ Val), 2.93 (s, 3H, $NCH_3$), 2.97 (dd, 1H, $1CH_2\beta$ Phe, $J_{1CH2\beta,CH\alpha}$=8.16 Hz), 3.08 (dd, 1H, $1CH_2\beta$ Phe, $J_{1CH2\beta,CH\alpha}$=8.04 Hz $J_{1CH2\beta,1CH2\beta}$=13.36 Hz), 3.74 (s, 3H, $OCH_3$), 4.45 (d, 1H, CHα Val, J=11.04 Hz), 4.5 (p, 1H, CHα Ala, $J_{CH\alpha,NH}$=7.2 Hz), 5.17-5.24 (dt, 1H, CHα Phe, $J_{CH\alpha,NH}$=6.09 Hz), 6.13 (bd, 1H, NH Phe), 6.59 (bd, 1H, NH Ala), 7.18-7.30 (5H, Ph).

$^{13}$C NMR ($CDCl_3$): δ 14.08 ($CH_3$ lipid), 17.86 ($CH_3\beta$ Ala), 18.64, 19.65 ($CH_{3\gamma}$ Val), 22.67 ($CH_2$ lipid), 25.53 ($CH_2CH_2CO$ lipid), 25.84 (CHβ Val), 29.21, 29.34, 29.45, 29.64, 29.68 ($CH_2$ lipid), 30.96 ($NCH_3$), 31.91 ($CH_2$ lipid), 36.44 ($CH_2CO$ lipid), 38.97 ($CH_2\beta$ Phe), 47.89 (CHα Ala), 50.38 (CHα Phe), 52.28 ($OCH_3$), 63.12 (CHα Val), 127.11, 128.57, 129.33, 135.80 (Ph), 169.05 (CO Val), 172.55 (CO lipid), 172.94 (CO Ala), 173.41 (CO Phe).

Lipid Extraction, 2-D TLC and 1-D TLC.

The culture of the S-type strain of Map afforded 317 mg of cells (dry weight). Lipids were extracted with chloroform/methanol (1:2 then 2:1 (vol/vol)) resulting in 7.6 mg of product. For analytical purposes, 500 µg of this crude extract were loaded on 2-D TLC plates and eluted using chloroform/methanol (96:4 (vol/vol)) in the first dimension followed by toluene/acetone (80:20 (vol/vol)) in the second dimension. Control synthetic L3P was deposited at 15 µg in chloroform and served as a marker for each dimension. TLC plates were revealed by spraying 10% copper sulfate in 8% phosphoric acid, followed by charring.

For the L3P purification, 7 mg of the crude extract in 100 µL of $CH_2Cl_2$ were loaded on preparative silica gel 60 $F_{254}$ 2-D TLC (20×20 cm, thickness 0.5 mm) (Merck) and eluted using the same solvent systems as above. After scraping the spot of interest (~7 mm diameter) off the silica plate, the L3P was eluted in batch with 4 times 500 µL of $CH_2Cl_2$/methanol 95:5 (vol/vol). The evaporation under argon afforded approximately 50 µg of purified native antigen. The adjacent silica gel zone below (~6 mm diameter spot) was treated using the same procedure for the NMR control.

This purified native L3P was analyzed by silica gel 60 $F_{254}$ 1-D TLC in comparison to both synthetic controls L3P and L5P (approximately 2 µg of each). The TLC was eluted with $CH_2Cl_2$/methanol 95:5 (vol/vol) and revealed as described above.

Surface-Exposed Material Preparation.

The surface-exposed material was recovered from myco-bacteria treated with 10 g of glass beads as previously described (Ortalo-Magne et al., 1996). Chloroform and methanol were added to the filtrates derived from this treatment obtain a partition mixture composed of chloroform/methanol/water (3:4:3 (vol/vol/vol)), then the organic phases were washed with water and evaporated to dryness to yield the cell surface-exposed lipids. The treated bacteria were extracted as described above to yield the cell bound lipids. Presence of cord factor was monitored by TLC developed in chloroform/methanol (90:10 (vol/vol)) and revelation by spraying 0.2% anthrone in sulfuric acid, followed by charring.

Analytical Procedures.

MALDI-TOF/TOF-MS and MS/MS analyses were conducted in the positive ionization and reflectron mode by accumulating 10 spectra of 250 laser shots, using the 5800 MALDI TOF/TOF Analyser (Applied Biosystems/Absciex) equipped with a Nd:Yag laser (349 nm wavelength). For MS and MS/MS data acquisitions, uniform, continuous, and random stage motion was selected at a fixed laser intensity of 4000 (instrument-specific units) and 400 Hz pulse rate and 6000 (instrument-specific units) and 1000 Hz, respectively. For MS/MS data acquisition, the fragmentation of selected precursors ions was performed at a collision energy of 1 kV using air as collision gas. Lipid samples were dissolved in chloroform and were directly spotted onto the target plate as 0.5 µl droplets, followed by the addition of 0.5 µL of matrix solution (10 mg of 2,5-dihydroxybenzoic acid (Sigma-Aldrich).$mL^{-1}$ in $CHCl_3$/$CH_3OH$, 1:1 (vol/vol)). Samples were allowed to crystallize at room temperature. Spectra were externally calibrated using lipid standards.

For comparative NMR analyses, 1-D $^1$H and $^1$H-COSY $^1$H/$^1$H (COrrelation SpectroscopY), compounds were dissolved in $CDCl_3$/$CD_3OD$ (1:1 (vol/vol), 99.8% purity, Euriso-top, CEA Saclay, France). Experiments were conducted using a 600 MHz Bruker NMR spectrometer equipped with cryosonde. $^1$H chemical shifts are given in parts/million (ppm) downfield from internal tetramethylsilane at 0 ppm. All experiments were recorded at 295° K without sample spinning. The Bruker pulse programs were used and optimized (pulse lengths and delays) for each 1-D or 2-D experiments. Data were analyzed using the TopSpin (Bruker BioSpin) software.

Example 2: Serological Results Using L5P Hydrosoluble Analogue and L3P to Detect Map Materials and Methods:
1. Material and Methods
a. Chemical Synthesis of the Antigens.

The antigens were synthesized manually on solid phase using Fmoc chemistry.

The L3P lipopeptide was prepared using a 4-hydroxymethylbenzoyl resin (HMBA-AM resin, Novabiochem) as previously described (Biet et al., 2008). After cleavage from the resin, the crude L3P was purified on a silica gel column using $CH_2Cl_2$/methanol as eluent (from 98/2 to 97/3 v/v), and 80 mg of the lipopeptide were obtained (yield 80%).

The $L5P^{H2O}$ antigen was prepared by attaching N-(Fmoc-13-amino-4,7,10-trioxa-tridecanyl)-diglycolic acid (Novabiochem) to a Wang resin using 1-(mesitylene-2-sulfonyl)-3-nitro-1,2,4-triazole and N-methylimidazole (B. Blankemeyer-Menge et al., 1990). The capping, coupling and deprotection steps were performed as previously described (Biet et al., 2008).

The product was cleaved from the resin with aqueous trifluoroacetic acid (TFA)/triisopropylsilane/$H_2O$ 95/2.5/2.5 v/v/v for 2 hours at room temperature. After filtration of the resin, the filtrate was concentrated, and diluted with $CH_2Cl_2$/$H_2O$ 50/50. The organic phase was extracted twice with $H_2O$. The aqueous phases were pooled and lyophilized. The crude $L5P^{H2O}$ was purified by reverse-phase flash chromatography using a gradient of $H_2O$+0.1% TFA/$CH_3CN$+0.1% TFA from 70/30 to 50/50 and 126 mg of the peptide derivative were obtained (yield 88%).

The purified compounds L3P and $L5P^{H2O}$ were characterized by electrospray ionization MS (Q-Tof Micro Waters), quantitative amino acid analysis (AAA) (after hydrolysis with 6N HCl at 110° C. for 48 h and using a Beckman 6300 analyzer) and NMR (Bruker 400 MHz instrument).

L3P:
MS: $C_{39}H_{67}N_3O_5$ (calcd 657.5081) m/z 658.5155 [M+H]$^+$, 680.4994 [M+Na]$^+$.

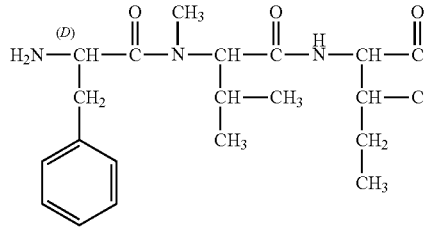

AAA: Ala 1 (1), Phe 0.96 (1), and an extra peak typical of N-Methyl-Val.

$^1$H NMR (CDCl$_3$): δ 0.60 (d, 3H, CH$_{3\gamma}$ Val, J=6.68 Hz), 0.90 (t, 3H, CH$_3$ lipid, J=7.05 Hz), 0.96 (d, 3H, CH$_{3\gamma}$ Val, J=6.41 Hz), 1.25-1.29 (m, 32H, 16 CH$_2$ lipid), 1.35 (d, 3H, CH$_3$β Ala, J=7.21 Hz), 1.53-1.59 (m, 2H, CH$_2$CH$_2$CO lipid), 2.15 (t, 3H, CH$_2$CO lipid, J=7.60 Hz), 2.18-2.27 (m, 1H, CHβ Val), 2.93 (s, 3H, NCH$_3$), 2.97 (dd, 1H, 1CH$_2$β Phe, J$_{1CH2\beta,CH\alpha}$=8.16 Hz), 3.08 (dd, 1H, 1CH$_2$β Phe, J$_{1CH2\beta,CH\alpha}$=8.04 Hz J$_{1CH2\beta,CH\beta}$=13.36 Hz), 3.74 (s, 3H, OCH$_3$), 4.45 (d, 1H, CHα Val, J=11.04 Hz), 4.5 (p, 1H, CHα Ala, J$_{CH\alpha,NH}$=7.2 Hz), 5.17-5.24 (dt, 1H, CHα Phe, J$_{CH\alpha,NH}$=6.09 Hz), 6.13 (bd, 1H, NH Phe), 6.59 (bd, 1H, NH Ala), 7.18-7.30 (5H, Ph).

$^{13}$C NMR (CDCl$_3$): 14.08 (CH$_3$ lipid), 17.86 (CH$_3$β Ala), 18.64, 19.65 (CH$_{3\gamma}$ Val), 558 22.67 (CH$_2$ lipid), 25.53 (CH$_2$CH$_2$CO lipid), 25.84 (CHβ Val), 29.21, 29.34, 29.45, 29.64, 29.68 (CH$_2$ lipid), 30.96 (NCH$_3$), 31.91 (CH$_2$ lipid), 36.44 (CH$_2$CO lipid), 38.97 (CH$_2$β Phe), 47.89 (CHα Ala), 50.38 (CHα Phe), 52.28 (OCH$_3$), 63.12 (CHα Val), 127.11, 128.57, 129.33, 135.80 (Ph), 169.05 (CO Val), 172.55 (CO lipid), 172.94 (CO Ala), 173.41 (CO Phe).

$L5P^{H2O}$:
MS: $C_{47}H_{73}N_7O_{12}$ (calcd 927.5317) m/z 928.5383 [M+H]$^+$, 950.5099 [M+Na]$^+$.

AAA: Ala 1 (1), Phe 1.79 (2), Ile 0.90 (1), and an extra peak typical of N-Methyl-Val.

$^1$H NMR (MeOD): δ 0.68 (d, 3H, CH$_{3\gamma}$ Val, J=6.56 Hz), 0.79 (d, 3H, CH$_{3\gamma}$ Val, J=6.64 Hz), 0.81 (d, 3H, CH$_{3\gamma}$ Ile, J=6.89 Hz), 0.85 (t, 3H, CH$_{3\delta}$ Ile, J=7.38 Hz), 1.01-1.09 (m, 1H, 1CH$_{2\gamma}$ Ile), 1.30 (d, 3H, CH$_3$β Ala, J=7.12 Hz), 1.45-1.51 (m, 1H, 1CH$_{2\gamma}$ Ile), 1.70-1.81 (m, 5H, CHβ Ile, CH$_2$ D and K), 2.08-2.14 (m, 1H, CH$_2$β Val), 2.92 (dd, 1H, 1CH$_2$β Phe), 3.01 (dd, 1H, 1CH$_2$β Phe), 3.05 (s, 3H, NCH$_3$), 3.13 (dd, 1H, 1CH$_2$β Phe), 3.20 (dd, 1H, 1CH$_2$β Phe), 3.23 (t, 2H, CH$_2$ C or L, J=6.86 Hz), 3.33 (t, 2H, CH$_2$ C or L, J=6.84 Hz), 3.48-3.54 (m, 4H, CH$_2$ E and J), 3.56-3.64 (m, 8H, CH$_2$ F, G, H and I), 4.04 (s, 2H, CH$_2$ B), 4.06-4.10 (m, 1H, CHα Ile), 4.18 (s, 2H, CH$_2$ A), 4.23-4.28 (q, 1H, CHα Ala), 4.47 (d, 1H, CHα Val, J=10.96 Hz), 4.61 (dt, 1H, CHα Phe), 4.68 (dt, 1H, CHα Phe), 7.16-7.19 (m, 2H, NH PEG), 7.21-7.38 (m, 10H, 2Ph), 7.97 (d, NH Ile), 8.13 (d, NH Phe).

$^{13}$C NMR (MeOD): δ 11.34 (CH$_3$δ Ile), 15.75 (CH$_{3\gamma}$ Ile), 18.34 (CH$_3$β Ala), 19.87, 20.00 (2CH$_{3\gamma}$ Val), 26.10 (CH$_{2\gamma}$ Ile), 28.50 (CHβ Val), 30.35, 30.38 (CH$_2$ D and K), 32.05 (NCH$_3$), 37.69, 37.90 (CH$_2$ C and L), 38.14, 38.61 (2CH$_2$β Phe), 50.56 (CHα Ala), 53.35, 55.93 (CHα Phe), 59.50 (CHα Ile), 64.94 (CHα Val), 69.22 (CH$_2$ A), 69.82, 70.11 (CH$_2$ E and J), 71.28, 71.31, 71.52, 71.58 (CH$_2$ B, F, G, H, and I), 127.87, 129.08, 129.56, 130.27, 130.35, 130.59, 135.26, 138.28 (Ph), 171.06, 171.92, 172.20, 172.85, 173.25, 173.63, 174.43 (CO).

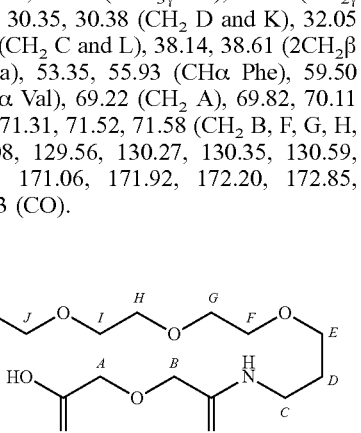

b. Sera

The potential of L5P and L3P as Map diagnostic antigen was assessed by ELISA. To validate thoroughly the diagnostic value of these molecules with appropriate sample sizes, the inventors used collection of sera already extensively described (Leroy et al, Proteomics 2007) (Mercier et al., Veterinary Record (2010) (Schinköthe J et al. J Comp Pathol. 2016 August-October; 155(2-3):218-30) (Dukkipati V S Vet Microbiol. 2016 Nov. 15; 195:136-143). They also used sera from animals infected by *M. bovis* form (J L Moyen Laboratoire Départemental d'Analyse & de Recherche de Dordogne).

c. Antibody ELISA Procedure

Preparation of antigen solution: The synthetic L5P lyophilized was carefully dissolved with ethanol or methanol. The required volume of ethanol to give a stock concentration of 1 mg/ml was added in the tube. The lyophilisate was then allowed to resuspend for at least 2 hours (gentle stirring). It is recommended to keep the working solution at room temperature taking care to avoid evaporation. L5P was used at a working concentration of 25 μg/mL in ethanol or methanol. 50 μL of antigen preparation were added in each well of the microplate Nunc Maxisorp and incubated for 18 hours at 4° C. with PPD or water-soluble variant. For the L5P coating plate were incubated 18 hours at 37° C. until total methanol evaporation (do not cover the plate). Plates were then washed three times with 200 μL of PBS containing 0.05% TWEEN 20 (Polyoxyethylenesorbitan monolaurate) (PBS-T), and 50 μL Blocking Buffer PBS-TG (PBS-0.05% TWEEN 20 (Polyoxyethylenesorbitan monolaurate), 0.5% Gelatin ref BIO-RAD 170-6537) were added to each well and incubated for 1 hour 30 min at 37° C.

After removing the blocking buffer 50 μL of primary antibody or serum diluted (1/100) in PBS-TG to each well were added and plates were incubated for 1 hour 30 at 37° C.

Plates were washed five times with 200 μL of PBS-T, and 50 μL of a solution of Recombinant Protein G Peroxidase Conjugated (reference 31499, Thermo Scientific) diluted at 0.5 μg/mL in PBS 0.05% TWEEN 20 (Polyoxyethylenesorbitan monolaurate) were added to each well and plates were incubated for 1 hour at room temperature.

Plates were then washed five times with 200 μL of PBS-T, and HRP substrate were added. The plates were read photometrically at 414 nm.

d. Storage

Before solubilization, L5P can be conserved at 4° C. or −20° C., and after solubilization at room temperature less than 2 days.

Results:

$L5P^{H2O}$ is a Suitable Hydrosoluble Derivative of L5P:

The L5P is very hydrophobic and does behave very differently as compared to conventional proteic antigens which are hydrosoluble. It is soluble in DMSO, $CHCl_3$, $CH_2Cl_2$, MeOH and EtOH (<1 mg/ml), but insoluble in water or aqueous buffers. Glass containers are thus to be used, and contacts with polypropylene/ependorf surface are to be minimized. Material handling like dilution and transfer steps is also to be minimized.

These properties of L5P are thus likely to cause difficulties in using a diagnostic test based on the L5P as antigen.

The inventors have thus developed a hydrosoluble derivative of L5P, named $L5P^{H2O}$, in order to circumvent these potential difficulties. The structure of L5P and $L5P^{H2O}$ are illustrated in FIG. 9.

FIG. 10 shows the performance of L5P and the hydrosoluble derivative $L5P^{H2O}$ on a panel of previously well-defined sera (Leroy et al, Proteomics 2007) including 60 positive sera from bovine infected by Map (MAP+) and 53 sera from healthy bovine (Controls). In ROC analysis of L5P, the area under the curve and its standard error were found equal to 0.97 (95% confidence interval, 0.94557 to 0.9955) and 0.01269, respectively. The $L5P^{H2O}$ was successfully evaluated whether in ethanol or in PBS. In ROC analysis, the area under the curve and its standard error were found equal to 0.9313 (95% confidence interval, 0.8843 to 0.9783) and 0.02398, and 0.9453 (95% confidence interval, 0.9064 to 0.9841) and 0.01981, respectively.

These results confirm that both L5P and $L5P^{H2O}$ have satisfying performance in the diagnosis of Map infection in bovine.

The inventors have moreover confirmed that the antibody response detected with sera of infected animals is not directed against the lipid moiety of L5P, as can be deduced from the results illustrated in FIG. 11.

It can thus be concluded that:

- L5P is a valuable biomarker to detect animal infected by Map. It was validated in ELISA using collections of sera from cattle.
- The ELISA detection relies on the L5P peptide since the lipid moiety does not discriminate control from infected animals
- A high quality hydrosoluble L5P derivative was synthesized.
- The hydrosoluble antigen $L5P^{H2O}$ is a satisfying synthetic mimic of L5P and can be advantageously used in a standard ELISA diagnostic test for detecting Map-infected animals.

L5P is Suitable to Discriminate Animals Infected by Map Versus *M. bovis:*

The inventors have then confirmed that L5P is an antigen specific for Map, absent from *M. bovis* and which does not cross-react with sera of animals infected by *M. bovis*. The corresponding results are illustrated in FIG. 12.

This antigen can therefore be used to discriminate animals infected with *M. bovis* from animals infected with Map. The same property is to be expected for the hydrosoluble analogue of L5P.

L5P is not Optimal as a Diagnostic Antigen in the Context of Ovine *Paratuberculosis* Induced by Map of S-Type:

The results illustrated in FIG. 13 show that less than half of the sheep sera do not appear to contain anti-L5P antibodies. In sheep the majority of strains of Map isolated are of type S and the inventors demonstrated (see example 1) that these strains do not produce the L5P, but rather the closely-related antigen called L3P (see FIG. 9 and example 1). This different antigenic composition of S-type strains is in agreement with the ELISA results presented in FIG. 13.

In view of the high number of undetermined diagnoses as illustrated in FIG. 13, it can be deduced that L5P does not seem suitable as a diagnostic antigen in the context of ovine *paratuberculosis* induced by Map of S-strain.

Use of L3P in the Map Serodiagnosis:

The inventors have then used L3P in Elisa serodiagnosis test, using the same protocol as detailed above for L5P. The results are presented in FIG. 14. These results show that L3P is recognized by the antibodies of animals infected by Map of S-type.

Anti-Map antibodies present in the serum of animals infected with C-type strains cross react with the L3P. These results are not surprising given the structures of the antigens that share epitopes. These results suggest that L3P, together with L5P, could be used for specific diagnosis of sheep (or other animal) infected with strains of type S.

The L3P will thus improve the serological diagnosis of Map in a context of infection with type S strains. Technical optimization of the ELISA protocol, especially steps of coating and saturation is in progress. The comprehensive evaluation of infected animals with accurately characterized strains is also in progress using a large collection of sera.

It is to be noted that these results were performed with a limited number of reference sera from bovines infected by C-type strains and sera from ovines infected by S-type strains. They nevertheless show that S-type is detected with L3P as antigen in the ELISA.

Example 3: L3P Promotes a Cell-Mediated Immune Response Whereas L5P Promotes B Cell Responses The present inventors have also confirmed that L3P elicits a cell mediated immune response as well as humoral response. By comparison with the immunoreactivity of L5P, they have moreover highlighted differences between L3P and L5P, namely they have demonstrated that there is a dose-dependent effect observed for L3P on upregulation of CD25+ CD8 T cells from infected cows, while L5P effects were static. In contrast, L5P demonstrated a significantly stronger induction of CD25+ B cells from infected animals compared to L3P.

Methods:
PBMC Isolation and Stimulation for Flow Cytometry and Cytokine Measurements.

Peripheral blood mononuclear cells (PBMCs) were isolated from control non-infected (n=4) and cattle naturally infected with C-type Map (n=4) to determine if lipoproteins, L3P and L5P (structures disclosed in FIG. 9), can elicit immunological responses. Sixty ml of blood was collected via jugular venipuncture into a syringe containing 2× acid-citrate-dextrose to obtain PBMCs.

PBMCs were resuspended at a final concentration of $8 \times 10^6$/ml in complete medium consisting of RPMI-1640 with 2 mM I-glutamine and 25 mM HEPES (Gibco, Grand Island, N.Y.) and supplemented with 10% fetal calf serum (Gibco), 100× penicillin-streptomycin (Gibco). Cells were plated in 24-well culture plates and incubated for 24 hr at 39° C. in 5% $CO_2$ in a humidified atmosphere with the following treatment groups, nonstimulated (NS; negative control), pokeweed mitogen (PWM, 10 µg/ml, positive control; Sigma, St. Louis, Mo.), and four antigens that included whole cell sonicated extracts of Map strains K-10 and S397 (10 µg/ml); lipoproteins L3P and L5P (1, 5, 10 µg/ml concentrations). The lipoproteins had to be solubilized in 100% methanol to 1 mg/ml concentrations and then diluted in the complete medium to final concentrations indicated above. This diluted solvent-lipopeptide mixture did not affect cell viability or response capabilities. After a 24-hr stimulation, the supernatants were harvested by centrifugation at 400×g for 5 min. Supernatants were removed without disturbing the cells in culture and stored at −20° C. until cytokine measurement. Cytokines IFN-γ, IL-1, IL-2, IL-4, IL-6 and TNF-α were all measured using Ciraplex bovine multiplex cytokine arrays (Aushon Biosystems, Billerica, Mass.).

For flow cytometry, PBMCs were cultured in replicate 48-well flat-bottom plates (Nunc Technologies, Rochester, N.Y.) as described above with the same culture conditions and in vitro treatments. After incubating for either 3 days (NS, PWM) or 6 days (NS, antigens), cell populations were defined by labeling with 50 µl of a cocktail of primary antibodies to CD4, CD8, gamma delta T cell receptor (γδ TCR), and B cells, along with a CD25 activation marker (Washington State University Monoclonal Antibody Center, Pullman, Wash.). After a 15-min incubation at room temperature (RT), plates were centrifuged for 2 min at 400×g, the supernatant was decanted, and 50 µl of a secondary antibody cocktail was added, which included APC/Cy7 anti-mouse IgG2a (Southern Biotech, Birmingham, Ala.), AF350 anti-mouse IgG2b (Invitrogen, Waltham, Mass.), and BUV395 anti-mouse IgG3 (BDBiosciences, San Diego, Calif.). Live/Dead populations were separated using Zombie Yellow™ Fixable Viability Dye (Biolegend, San Diego, Calif.). Cells were analyzed on a BDBiosciences LSRII Cytometer using FACSDiva V8.0.1 software. Further analysis was done using FlowJo® v10.2 (FLOWJO, LLC) software.

Results:
After 24 hr culture, there was a dose-dependent proliferation of CD25+ CD8 T cells from infected cows stimulated with L3P. By contrast, L5P stimulated cells remained static over the range of lipopeptide concentrations (FIG. 15A). S397, S-type Map strain, which contains L3P, produced a slightly stronger response than K-10 strain, which has L5P, although this difference was not significant (data not shown). In contrast, effects of lipopeptides on CD25+ B cells were reversed as L5P promoted a significantly (P<0.0002) stronger response compared to L3P (FIG. 15B). No significant differences were observed between L3P and L5P in CD25+ CD4 or CD25+ γδ T cell populations (data not shown). Both L3P and L5P elicited cytokine responses to IFN-γ, IL-1β and TNF-α with no significant differences between the L3P or L5P treatments (FIG. 16). However, significant differences were observed between infected and control cells (P<0.0001 for IFN-γ and IL-1β, P<0.03 for TNF-α; FIG. 16). Interestingly, a dose-dependent effect (P<0.0006) of L5P concentration was observed on TNF-α secretion by PBMCs. IL-4 and IL-6 were not detected following stimulation with either lipopeptide (data not shown).

In the present study, L5P preferentially resulted in the upregulation of activated B cells (CD25+B cells), a finding that correlates with previous studies demonstrating this lipopentapeptide produces strong humoral responses in cattle and sheep (Biet et al., 2008). In contrast, L3P more distinctly upregulated T cell proliferation (CD25+CD8 T cells) in a dose-dependent manner, suggesting more of a Th1 immune response to this cell wall component. These results suggest that genomic differences between L3P and L5P may translate to antigenic differences that present immunological diversity within the infected host.

BIBLIOGRAPHIC REFERENCES

Alonso-Hearn, M., T. M. et al, (2010). *Innate Immun* 16: 235-247.
Amonsin, A., L. L. et al, (2004). *J. Clin. Microbiol.* 42: 1694-1702.
Bannantine, J. P., et al, (2014). *Genome announcements* 2.
Bannantine, J. P. et al, (2012). *BMC Genomics* 13: 89.
Bernut, A., J. L. et al, (2014). *Proc. Natl. Acad. Sci. U.S.A.* 111: E943-952.
Biet, F. et al, (2008). *Vaccine* 26: 257-268.
Biet, F. et al, (2012). *BMC Microbiol* 12: 264.
Blankemeyer-Menge B. et al. Tetrahedron Letters (1990) 31, 1701]
Dohmann, K., B. et al, (2003). *J. Clin. Microbiol.* 41: 5215-5223.
Eckstein, T. M., S. et al, (2006). *J. Biol. Chem.* 281: 5209-5215.
Gaudelli, N. M., D. H. Long & C. A. Townsend, (2015). *Nature* 520: 383-387.
Ghosh, P., C. et al, (2012). *PLoS One* 7: e31947.
Gumber, S., D. L. et al, (2009). *Vet. Microbiol.* 133: 344-357.

Gumber, S. & R. J. Whittington, (2009). *Vet. Microbiol.* 136: 82-90.
Holbert, S., M. et al, (2015). *Res. Vet. Sci.* 102: 118-121.
Howard, S. T., E. et al, (2006). *Microbiology* 152: 1581-1590.
Janagama, H. K. et al, (2009). *Microbiology* 155: 3683-3690.
Jimenez-Dalmaroni, M. J. et al, (2015). *Innate Immun* 21: 175-193.
Kansal, R. G., R. Gomez-Flores & R. T. Mehta, (1998). *Microb. Pathog.* 25: 203-214.
Lefrancois, L. H. et al, (2013). *J. Bacteriol.* 195: 4844-4853.
Li, L., et al (2005). *Proc. Natl. Acad. Sci. U.S.A.* 102: 12344-12349.
Marsh, I., et al (1999). *Mol. Cell. Probes* 13: 115-126.
Marsh, I. B., et al (2006). *J. Bacteriol.* 188: 2290-2293.
Motiwala, A. S., et al (2006). *Infect. Immun.* 74: 6046-6056.
NAHMS, (2008) Johne's disease on U.S. dairies, 1991-2007. *USDA-APHIS-VS-CEAH* Fort Collins, Colo. Center for Epidemiology and Animal Health: 1-4.
Ortalo-Magne, A. et al, (1996). *J. Bacteriol.* 178: 456-461.
Ripoll, F. et al, (2007). *BMC Genomics* 8: 114.
Riviere, M. et al, (1996). *Eur. J. Biochem.* 241: 682-690.
Rottig, M., et al, (2011). *Nucleic Acids Res.* 39: W362-367.
Semret, M. et al, (2006). *J. Clin. Microbiol.* 44: 881-887.
Sibley, J. A. et al, (2007). *J. Wildl. Dis.* 43: 775-779.
Southern, E. M., (1975). *J. Mol. Biol.* 98: 503-517.
Stevenson, K. et al, (2002). *J. Clin. Microbiol.* 40: 1798-1804.
Thibault, V. C. et al, (2008). *J. Clin. Microbiol.* 46: 4091-4094.
Turenne, C. Y. et al, (2006). *J. Clin. Microbiol.* 44: 433-440.
van Soolingen, D. et al, (1994). *Methods Enzymol.* 235: 196-205.
Verdier, J. et al (2013). *PLoS One* 8: e62780.
Walsh, C. T. et al, (2013). *Angewandte Chemie. International Ed. In English* 52: 7098-7124.
Wang, H. et al, (2014). *Proc. Natl. Acad. Sci. U.S.A.* 111: 9259-9264.
Whittington, R. J. et al, (2011). *J. Clin. Microbiol.* 49: 1822-1830.
Wright, E. L. et al, (1996). *J. Clin. Microbiol.* 34: 2475-2478.
Wu, C. W. et al, (2006). *J. Bacteriol.* 188: 711-723.

The invention claimed is:

1. An isolated synthetic tripeptide chosen from the group consisting of:
    (a) a tripeptide of formula H-D-Phe-N-Methyl-L-Val-L-Ala-OMe (SEQ ID NO:1);
    (b) a tripeptide of formula H-L-Phe-N-Methyl-L-Val-L-Ala-OMe (SEQ ID NO:2);
    (c) a tripeptide of formula H-D-Phe-L-Val-L-Ala-OMe (SEQ ID NO:3);
    (d) a tripeptide of formula H-D-Phe-N-Methyl-L-Val-L-Ala-OH (SEQ ID NO:4);
    (e) a tripeptide of formula H-L-Phe-L-Val-L-Ala-OMe (SEQ ID NO:5);
    (f) a tripeptide of formula H-D-Phe-L-Val-L-Ala-OH (SEQ ID NO:6);
    (g) a tripeptide of formula H-L-Phe-N-Methyl-L-Val-L-Ala-OH (SEQ ID NO:7); and
    (h) a tripeptide of formula H-L-Phe-L-Val-L-Ala-OH (SEQ ID NO:8).

2. A composition comprising an antigen specific to *Mycobacterium avium* subsp. *paratuberculosis* (Map) S-type, wherein the antigen is chosen from the group consisting of
    (i) an isolated synthetic tripeptide according to claim 1; and
    (ii) an isolated synthetic tripeptide comprising a tripeptide according to (i), wherein the Phenylalanine at the N-terminus is N-acylated with a $C_1$ to $C_{30}$ acyl moiety, which is not a fatty acid moiety.

3. A diagnostic kit for diagnosing *Mycobacterium avium* subsp. *paratuberculosis* (Map) S-type infection in a subject, comprising an antigen specific to Map S-type and reagents for detecting an antigen-antibody complex, wherein the antigen is chosen from:
    (i) an isolated synthetic tripeptide according to claim 1; and
    (ii) an isolated synthetic tripeptide comprising a tripeptide according to (i), wherein the Phenylalanine at the N-terminus is N-acylated with a $C_1$ to $C_{30}$ acyl moiety, which is not a fatty acid moiety.

4. An antigenic composition comprising
    A) (i) an isolated synthetic tripeptide according to claim 1; or
        (ii) an isolated synthetic tripeptide comprising a tripeptide according to (i), wherein the Phenylalanine at the N-terminus is N-acylated with a $C_1$ to $C_{30}$ acyl moiety, which is not a fatty acid moiety; and B) a pentapeptide conjugate comprising a pentapeptide core having the sequence H-Phe-Val-Ile-Phe-Ala-OH (SEQ ID NO:13), wherein the 5 amino acids are independently natural amino acids or modified amino acids, and wherein the pentapeptide core is further modified by amidation of C-terminal Alanine with a polyethylene glycol moiety;

amidation of C-terminal Alanine with a polyethylene glycol moiety and N-acylation of the N-terminus; or addition of a polyethylene glycol moiety at the N-terminus of the pentapeptide;

wherein said pentapeptide conjugate is hydrosoluble and wherein said polyethylene glycol has the structure $(CH_2)_3$—$O(CH_2CH_2O)_2$—$(CH_2)_3NHCOCH_2OCH_2COOH$.

5. A method for in vitro detection of specific anti-*Mycobacterium avium* subsp. *paratuberculosis* (Map) antibodies in a sample, comprising contacting said sample with an antigen, wherein said antigen is chosen from the group consisting of:

(i) an isolated synthetic tripeptide chosen from the group consisting of:
  (a) a tripeptide of formula H-D-Phe-N-Methyl-L-Val-L-Ala-OMe (SEQ ID NO:1);
  (b) a tripeptide of formula H-L-Phe-N-Methyl-L-Val-L-Ala-OMe (SEQ ID NO:2);
  (c) a tripeptide of formula H-D-Phe-L-Val-L-Ala-OMe (SEQ ID NO:3);
  (d) a tripeptide of formula H-D-Phe-N-Methyl-L-Val-L-Ala-OH (SEQ ID NO:4);
  (e) a tripeptide of formula H-L-Phe-L-Val-L-Ala-OMe (SEQ ID NO:5);
  (f) a tripeptide of formula H-D-Phe-L-Val-L-Ala-OH (SEQ ID NO:6);
  (g) a tripeptide of formula H-L-Phe-N-Methyl-L-Val-L-Ala-OH (SEQ ID NO:7); and
  (h) a tripeptide of formula H-L-Phe-L-Val-L-Ala-OH (SEQ ID NO:8); and (ii) an isolated synthetic tripeptide comprising a tripeptide according to (i), wherein the Phenylalanine at the N-terminus is N-acylated with a $C_1$ to $C_{30}$ acyl moiety, which is not a fatty acid moiety;

contacting sample with reagents for detecting an antigen-antibody complex with said antigen; and detecting an antigen-antibody complex with said antigen;

wherein the detection of the antigen-antibody complex with said antigen is indicative of the presence of specific anti-Map antibodies.

6. The method according to claim 5, wherein the sample is a sample of blood, serum, faeces, milk, lymph nodes, gut biopsies or urine.

7. A method for diagnosing Map infection in a subject, comprising contacting a sample obtained from said subject with an antigen, wherein said antigen is chosen from the group consisting of:

(i) an isolated synthetic a tripeptide chosen from the group consisting of:
  (a) a tripeptide of formula H-D-Phe-N-Methyl-L-Val-L-Ala-OMe (SEQ ID NO:1);
  (b) a tripeptide of formula H-L-Phe-N-Methyl-L-Val-L-Ala-OMe (SEQ ID NO:2);
  (c) a tripeptide of formula H-D-Phe-L-Val-L-Ala-OMe (SEQ ID NO:3);
  (d) a tripeptide of formula H-D-Phe-N-Methyl-L-Val-L-Ala-OH (SEQ ID NO:4);
  (e) a tripeptide of formula H-L-Phe-L-Val-L-Ala-OMe (SEQ ID NO:5);
  (f) a tripeptide of formula H-D-Phe-L-Val-L-Ala-OH (SEQ ID NO:6);
  (g) a tripeptide of formula H-L-Phe-N-Methyl-L-Val-L-Ala-OH (SEQ ID NO:7); and
  (h) a tripeptide of formula H-L-Phe-L-Val-L-Ala-OH (SEQ ID NO:8); and (ii) an isolated synthetic tripeptide comprising a tripeptide according to (i), wherein the Phenylalanine at the N-terminus is N-acylated with a $C_1$ to $C_{30}$ acyl moiety, which is not a fatty acid moiety;

contacting sample with reagents for detecting an antigen-antibody complex with said antigen; and detecting an antigen-antibody complex with said antigen;

wherein the detection of the antigen-antibody complex with said antigen is indicative of Map infection or Map infection history, in a subject not vaccinated against Map.

8. The method according to claim 7, wherein the detection of an antigen-antibody complex is carried out by enzyme-linked immunosorbent assay (ELISA), radioimmunoassay, electrophoresis, immunofluorescence or Western Blot.

9. A method for in vitro detecting humoral immune response directed against Map in a subject, comprising contacting a biological sample obtained from said subject with an antigen, wherein said antigen is chosen from the group consisting of:

(i) an isolated synthetic tripeptide chosen from the group consisting of:
  (a) a tripeptide of formula H-D-Phe-N-Methyl-L-Val-L-Ala-OMe (SEQ ID NO:1);
  (b) a tripeptide of formula H-L-Phe-N-Methyl-L-Val-L-Ala-OMe (SEQ ID NO:2);
  (c) a tripeptide of formula H-D-Phe-L-Val-L-Ala-OMe (SEQ ID NO:3);
  (d) a tripeptide of formula H-D-Phe-N-Methyl-L-Val-L-Ala-OH (SEQ ID NO:4);
  (e) a tripeptide of formula H-L-Phe-L-Val-L-Ala-OMe (SEQ ID NO:5);
  (f) a tripeptide of formula H-D-Phe-L-Val-L-Ala-OH (SEQ ID NO:6);
  (g) a tripeptide of formula H-L-Phe-N-Methyl-L-Val-L-Ala-OH (SEQ ID NO:7); and
  (h) a tripeptide of formula H-L-Phe-L-Val-L-Ala-OH (SEQ ID NO:8); and (ii) an isolated synthetic tripeptide comprising a tripeptide according to (i), wherein the Phenylalanine at the N-terminus is N-acylated with a $C_1$ to $C_{30}$ acyl moiety, which is not a fatty acid moiety;

contacting sample with reagents for detecting an antigen-antibody complex with said antigen; and detecting an antigen-antibody complex with said antigen;

wherein the detection of the antigen-antibody complex with said antigen is indicative of humoral immune response directed against Map.

10. The method according to claim 9, wherein the subject is an animal more prone to Map S-type infection than Map C-type infection.

11. A method for evaluating in vitro cell immune response directed against Map in a subject, comprising:
A) contacting a biological sample obtained from said subject with an antigen, wherein said antigen is chosen from the group consisting of:
(i) an isolated synthetic tripeptide according to claim 1; and
(ii) an isolated synthetic tripeptide comprising a tripeptide according to (i), wherein the Phenylalanine at the N-terminus is N-acylated with a $C_1$ to $C_{30}$ acyl moiety, which is not a fatty acid moiety; and
B) detecting cytokine expression by the cells present in the biological sample or detecting lymphoproliferation, wherein the detection of cytokine expression or lymphoproliferation is indicative of a cell immune response directed against Map in the subject.

12. The method according to claim 11, wherein the cytokine is IFNγ or IL-10.

13. The method according to claim 11, wherein the sample is blood, PBMC isolated from blood, lymph nodes or gut biopsies.

14. A method for in vitro detecting humoral immune response directed against Map in a subject, comprising contacting a biological sample obtained from said subject with an antigen, wherein said antigen is chosen from the group consisting of:
(i) an isolated synthetic tripeptide selected from a tripeptide having the amino acid sequence of any of SEQ ID Nos 1-8;
(ii) a tripeptide which differs from the tripeptide according to (i) by substitution of the L-Val by D-Val and/or substitution of L-Ala by D-Ala, and/or N-alkylation of one or more of Phe, Val and Ala, and/or the retro-inverso sequence; and
(iii) an isolated synthetic tripeptide comprising a tripeptide according to (i) or (ii), wherein the Phenylalanine at the N-terminus is N-acylated with a C1 to C30 acyl moiety;
contacting sample with reagents for detecting an antigen-antibody complex with said antigen; and
detecting an antigen-antibody complex with said antigen;
wherein the detection of the antigen-antibody complex with said antigen is indicative of humoral immune response directed against Map.

15. The method according to claim 14, wherein the Phenylalanine at the N-terminus is N-acylated with a $C_1$ to $C_{30}$ acyl moiety, which is not a fatty acid moiety.

16. The method according to claim 14, wherein the Phenylalanine at the N-terminus is N-acylated with a $C_1$ to $C_{30}$ aliphatic acyl moiety.

17. The method according to claim 16, wherein the N-terminal Phenylalanine is N-acylated with an eicosanoic acid acyl chain.

18. The method according to claim 16, wherein the Phenylalanine at the N-terminus is N-acylated with a $C_{10}$ to $C_{28}$ fatty acid moiety.

19. The method according to claim 16, wherein the Phenylalanine at the N-terminus is N-acylated with a $C_{18}$-$C_{22}$ saturated or unsaturated fatty acid moiety.

20. The method according to claim 14, wherein the methyl ester present at the C-terminus of the Alanine is substituted by another alkyl ester, or wherein the C-terminal Alanine is amidated.

21. The method according to claim 20, wherein the C-terminal Alanine is amidated with a polyethylene glycol (PEG) moiety having the formula $(CH_2)_3-O(CH_2CH_2O)_2-(CH_2)_3NHCOCH_2OCH_2COOH$.

22. The method according to claim 20, wherein the C-terminal Alanine is amidated by a protein conjugation, or with a polyethylene glycol moiety.

* * * * *

```
SEQUENCE LISTING

<160> NUMBER OF SEQ ID NOS: 45

<210> SEQ ID NO 1
<211> LENGTH: 3
<212> TYPE: PRT
<213> ORGANISM: artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-phenylalanine
<220> FEATURE:
<221> NAME/KEY: MISC_FEATURE
<222> LOCATION: (2)..(2)
<223> OTHER INFORMATION: N-methylation
<220> FEATURE:
<221> NAME/KEY: MISC_FEATURE
<222> LOCATION: (3)..(3)
<223> OTHER INFORMATION: O-methylation

<400> SEQUENCE: 1

Phe Val Ala
1

<210> SEQ ID NO 2
<211> LENGTH: 3
<212> TYPE: PRT
<213> ORGANISM: artificial
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: N-methylation
<220> FEATURE:
<221> NAME/KEY: MISC_FEATURE
<222> LOCATION: (3)..(3)
<223> OTHER INFORMATION: O-methylation

<400> SEQUENCE: 2

Phe Val Ala
1

<210> SEQ ID NO 3
<211> LENGTH: 3
```

```
<212> TYPE: PRT
<213> ORGANISM: artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: D-phenylalanine
<220> FEATURE:
<221> NAME/KEY: MISC_FEATURE
<222> LOCATION: (3)..(3)
<223> OTHER INFORMATION: O-methylation

<400> SEQUENCE: 3

Phe Val Ala
1

<210> SEQ ID NO 4
<211> LENGTH: 3
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-phenylalanine
<220> FEATURE:
<221> NAME/KEY: MISC_FEATURE
<222> LOCATION: (2)..(2)
<223> OTHER INFORMATION: N-methylation

<400> SEQUENCE: 4

Phe Val Ala
1

<210> SEQ ID NO 5
<211> LENGTH: 3
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: O-methylation

<400> SEQUENCE: 5

Phe Val Ala
1

<210> SEQ ID NO 6
<211> LENGTH: 3
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-phenylalanine

<400> SEQUENCE: 6

Phe Val Ala
1

<210> SEQ ID NO 7
<211> LENGTH: 3
<212> TYPE: PRT
<213> ORGANISM: artificial
<220> FEATURE:
```

```
<223> OTHER INFORMATION: Synthetic peptide
<220> FEATURE:
<221> NAME/KEY: MISC_FEATURE
<222> LOCATION: (2)..(2)
<223> OTHER INFORMATION: N-methylation

<400> SEQUENCE: 7

Phe Val Ala
1

<210> SEQ ID NO 8
<211> LENGTH: 3
<212> TYPE: PRT
<213> ORGANISM: Artificial
<220> FEATURE:
<223> OTHER INFORMATION: Synthetic peptide

<400> SEQUENCE: 8

Phe Val Ala
1

<210> SEQ ID NO 9
<211> LENGTH: 3
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: D-phenylalanine
<220> FEATURE:
<221> NAME/KEY: MISC_FEATURE
<222> LOCATION: (2)..(2)
<223> OTHER INFORMATION: N-methylation
<220> FEATURE:
<221> NAME/KEY: MISC_FEATURE
<222> LOCATION: (3)..(3)
<223> OTHER INFORMATION: amidation of the C-terminus

<400> SEQUENCE: 9

Phe Val Ala
1

<210> SEQ ID NO 10
<211> LENGTH: 20
<212> TYPE: DNA
<213> ORGANISM: Artificial
<220> FEATURE:
<223> OTHER INFORMATION: Primer

<400> SEQUENCE: 10
gtgcagtacg ccgactacac                                              20

<210> SEQ ID NO 11
<211> LENGTH: 20
<212> TYPE: DNA
<213> ORGANISM: Artificial
<220> FEATURE:
<223> OTHER INFORMATION: primer

<400> SEQUENCE: 11
agaaaccgat cagctcgtcg                                              20

<210> SEQ ID NO 12
<211> LENGTH: 18
<212> TYPE: DNA
<213> ORGANISM: Artificial
<220> FEATURE:
```

-continued

<223> OTHER INFORMATION: primer

<400> SEQUENCE: 12
accgggaaaa cagcagtg                                                 18

<210> SEQ ID NO 13
<211> LENGTH: 5
<212> TYPE: PRT
<213> ORGANISM: Artificial
<220> FEATURE:
<223> OTHER INFORMATION: synthetic peptide

<400> SEQUENCE: 13

Phe Val Ile Phe Ala
1               5

<210> SEQ ID NO 14
<211> LENGTH: 5
<212> TYPE: PRT
<213> ORGANISM: artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: D-phenylalanine
<220> FEATURE:
<221> NAME/KEY: MISC_FEATURE
<222> LOCATION: (2)..(2)
<223> OTHER INFORMATION: N-methylation
<220> FEATURE:
<221> NAME/KEY: MISC_FEATURE
<222> LOCATION: (5)..(5)
<223> OTHER INFORMATION: O-methylation

<400> SEQUENCE: 14

Phe Val Ile Phe Ala
1               5

<210> SEQ ID NO 15
<211> LENGTH: 5
<212> TYPE: PRT
<213> ORGANISM: artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-phenylalanine
<220> FEATURE:
<221> NAME/KEY: MISC_FEATURE
<222> LOCATION: (2)..(2)
<223> OTHER INFORMATION: N-methylation
<220> FEATURE:
<221> NAME/KEY: MISC_FEATURE
<222> LOCATION: (5)..(5)
<223> OTHER INFORMATION: amidation of the C-terminus

<400> SEQUENCE: 15

Phe Val Ile Phe Ala
1               5

<210> SEQ ID NO 16
<211> LENGTH: 4274
<212> TYPE: PRT
<213> ORGANISM: Mycobacterium avium

<400> SEQUENCE: 16

Met Lys Arg Gly Asp Arg Ala Tyr Pro Val Thr Arg Gly Gln Leu Asp
1               5                   10                  15

-continued

```
Ile Trp Leu Ala Glu Gln Thr Gly His Leu Asp Val Ala Trp Gln Leu
         20                  25                  30

Gly Val Leu Val Arg Ile Asp Gly Ile Asp Pro Ala Leu Leu His
     35                  40                  45

Gln Thr Met Arg His Val Val Gly Glu Ala Glu Ser Leu Arg Ala Ser
 50                  55                  60

Phe Phe Glu Ala Asp Gly Gln Val Phe Gln Lys Ala Val Glu Tyr Ser
 65                  70                  75                  80

Asp Val Asp Leu Thr Phe Tyr Asp Leu Ser Gly Ser Ser Asp Pro Glu
                 85                  90                  95

Arg Glu Val Arg Glu Met Thr Ala Ser Ile Gln Arg Thr Pro Met Pro
            100                 105                 110

Leu Thr Gly Pro Met Ile Lys Phe Ala Leu Phe Arg Thr Gly Ser Ala
        115                 120                 125

Glu Tyr Tyr Trp Phe Thr Thr Cys His His Ile Ala Ile Asp Gly Met
130                 135                 140

Gly Ile Ala Leu Val Gly Arg Arg Ile Ala Ala Val Tyr Thr Ala Leu
145                 150                 155                 160

Ala Ser Gly Lys Pro Ile Pro Pro Ala Phe Phe Gly Ser Leu Gln Asp
                165                 170                 175

Leu Val Gly Gly Glu Leu Glu Tyr Glu Ala Ser Ala Lys Phe Leu Glu
            180                 185                 190

Asp Lys Asp Tyr Trp Leu Ala His Arg Pro Gly Asp Gly Thr Ala Gly
        195                 200                 205

His Pro Pro Arg Pro Ala Asp Asp Gly Arg Asp Pro Tyr Ser Pro Ser
210                 215                 220

Pro Pro Val Gln Leu Asp Glu Ser Val Ile Gly Ser Val Lys Glu Leu
225                 230                 235                 240

Ser Lys Ala Leu Gly Ile Arg Arg Ser Ser Val Leu Thr Ala Ala Cys
                245                 250                 255

Ala Leu Leu Val Arg Gly Trp Cys Ala Asp Gly Ser Asp Glu Val Val
            260                 265                 270

Leu Asp Phe Pro Val Ser Arg Arg Val Asp Pro Lys Ser Lys Thr His
        275                 280                 285

Pro Gly Met Leu Ala Gly Val Val Pro Leu Val Leu His Ala Pro Ala
290                 295                 300

Ala Ala Thr Phe Ala Asp Phe Cys Arg His Val Asp Gln Arg Ser Arg
305                 310                 315                 320

Glu Ala Leu Arg His Gln Gln Phe Pro Thr Arg Thr Leu Asp Gly Glu
                325                 330                 335

Gly Asp Phe Ser Gly Pro Arg Gln Ala Pro Asn Arg Val Val Val Asn
            340                 345                 350

Phe Val Pro Ala Arg Leu Thr Leu Ser Leu Ala Asp Val Pro Ala Thr
        355                 360                 365

Ala Thr Tyr Thr Ser Phe Gly Pro Val Gly His Phe Gly Leu Phe Phe
370                 375                 380

Leu Gly Phe Gly Asp Gln Gln Phe Leu Ser Thr Val Gly Thr Gly Gln
385                 390                 395                 400

Pro Leu Ala Asn Phe Asp Ala Thr Asp Leu Ala Glu Arg Leu Gln Arg
                405                 410                 415

Ile Leu Ala Ala Met Ala Ala Asp Pro Ala Arg Leu Leu Ser Ser Leu
            420                 425                 430
```

```
Asp Val Leu Arg Asp Pro Glu His Ala Gln Leu Glu Ala Leu Gly Asn
            435                 440                 445
Thr Ala Val Leu Thr Arg Thr Pro Gly Pro Ala Val Ser Val Pro Glu
    450                 455                 460
Leu Phe Ala Thr Gln Val Ala Arg Ala Pro Gln Asp Val Ala Leu Val
465                 470                 475                 480
Cys Glu Gly Arg Ser Leu Thr Tyr Arg Gln Leu Asp Glu Ala Ser Asn
                485                 490                 495
Arg Leu Ala His Leu Leu Ala Gly Leu Gly Ala Gly Pro Gly Gln Ser
            500                 505                 510
Val Ala Leu Leu Phe Ser Arg Ser Ala Glu Ala Val Ala Ser Ile Leu
    515                 520                 525
Ala Val Leu Lys Thr Gly Ala Ala Tyr Leu Pro Ile Asp Pro Ala Ala
530                 535                 540
Pro Glu Thr Arg Ile Gly Phe Met Leu Ala Asp Ala Lys Pro Val Ala
545                 550                 555                 560
Ala Leu Ser Thr Ala Glu Leu Ala Gly Arg Leu Glu Gly His Gly Met
                565                 570                 575
Thr Val Ile Asp Val Asn Asp Pro Arg Ile Gln Asp Arg Pro Ala Thr
            580                 585                 590
Ala Leu Pro Val Pro Ala Ala Asp Gly Val Ala Tyr Val Ile Tyr Thr
    595                 600                 605
Ser Gly Thr Thr Gly Val Pro Lys Gly Val Ala Val Thr His Arg Asn
610                 615                 620
Val Thr Gln Leu Leu Gly Ser Leu Asp Ala Gly Leu Pro Pro Ala Gly
625                 630                 635                 640
Val Trp Ser Gln Cys His Ser Tyr Ala Phe Asp Val Ser Val Trp Glu
                645                 650                 655
Ile Phe Gly Ala Leu Leu Arg Gly Gly Arg Leu Val Val Pro Glu
            660                 665                 670
Asp Val Thr Arg Ala Pro Glu Glu Leu His Asp Val Leu Val Asn Glu
    675                 680                 685
Gln Val Ser Val Leu Thr Gln Thr Pro Ser Ala Val Ala Met Leu Ser
690                 695                 700
Pro Gln Gly Leu Glu Ser Val Ser Leu Val Val Val Gly Glu Ala Cys
705                 710                 715                 720
Pro Ala Glu Val Val Asp Arg Trp Ser Pro Gly Arg Val Met Val Asn
                725                 730                 735
Ala Tyr Gly Pro Thr Glu Thr Thr Met Cys Val Ala Ile Ser Ala Pro
            740                 745                 750
Leu Ala Pro Gly Met Gly Ser Pro Ile Gly Val Pro Val Asp Gly
    755                 760                 765
Ala Gly Leu Phe Val Leu Asp Ala Trp Leu Arg Pro Val Pro Pro Gly
770                 775                 780
Val Val Gly Glu Leu Tyr Val Gly Gly Ala Gly Val Ala Cys Gly Tyr
785                 790                 795                 800
Trp Arg Arg Gly Gly Leu Thr Ala Ser Trp Phe Val Ala Cys Pro Phe
                805                 810                 815
Gly Ala Pro Gly Ala Arg Met Tyr Arg Thr Gly Asp Leu Val Cys Trp
            820                 825                 830
Arg Ser Asp Gly Gln Leu Asp Tyr Arg Gly Arg Ala Asp Glu Gln Val
    835                 840                 845
Lys Val Arg Gly Tyr Arg Ile Glu Leu Gly Glu Val Gln Ala Ala Leu
```

```
                850            855              860
Ala Ala Leu Asp Asp Val Asp Gln Ala Val Ile Ala Arg Glu Asp
865                 870              875                 880

Arg Pro Gly Gly Lys Arg Leu Val Gly Tyr Ile Thr Gly Thr Ala Asp
                885              890              895

Pro Ala Glu Val Arg Thr Ala Leu Ala Gln Arg Leu Pro Val Tyr Met
            900              905              910

Val Pro Ala Ala Val Ala Leu Asp Ala Ile Pro Leu Thr Pro Asn
        915              920              925

Gly Lys Leu Asp Thr Arg Ala Leu Pro Thr Pro Glu Tyr Thr Gly Ser
    930              935              940

Arg Tyr Arg Ala Pro Ser Asn Ala Val Glu Glu Thr Val Ala Gly Ile
945              950              955                 960

Tyr Ala His Val Leu Gly Val Glu Arg Val Gly Val Asp Asp Ser Phe
                965              970              975

Phe Asp Leu Gly Gly Asp Ser Ile Ser Ala Leu Gln Val Val Ala Arg
            980              985              990

Ala Arg Ala Ala Gly Leu Thr Cys Arg Pro Arg Asp Val Phe Val Glu
        995             1000             1005

Gln Thr Val Ala Arg Leu Ala Arg Val Val Gly Ser Gly Asp Arg
       1010             1015             1020

Ala Ala Glu Val Ala Asp Glu Gly Val Gly Pro Val Pro Pro Thr
       1025             1030             1035

Pro Ile Met Arg Trp Leu Gln Ala Ala Glu Arg Ala Gly Gly Ala
       1040             1045             1050

Thr Asp Gln Phe Asn Gln Thr Val Leu Val Gln Ala Pro Ala Gly
       1055             1060             1065

Val Thr Glu Thr Glu Val Ala Ile Val Leu Gln Ala Leu Val Asp
       1070             1075             1080

Arg His Ala Met Leu Arg Leu Arg Val Thr Asp Asp Gly Ala Asp
       1085             1090             1095

Gly Trp Ser Phe Glu Val Pro Glu Ala Gly Ser Val Gln Ala Arg
       1100             1105             1110

Asp Cys Leu Arg Ser Val Asp Ala Leu Ser Asp Glu Ala Leu Leu
       1115             1120             1125

Ala Ala Arg Ala Arg Leu Asn Pro Ala Ala Gly Thr Met Leu Ala
       1130             1135             1140

Ala Leu Trp Val Glu Ala Thr Gly Gln Leu Ala Val Ile Ile His
       1145             1150             1155

His Leu Ala Val Asp Ala Val Ser Trp Trp Ile Leu Leu Glu Asp
       1160             1165             1170

Leu Asn Ile Ala Trp Ala Leu His Arg Ala Gly Gln Pro Val Glu
       1175             1180             1185

Leu Ala Pro Ala Gly Thr Ser Phe Ala Arg Trp Ala Arg Leu Leu
       1190             1195             1200

Asp Glu His Ala Arg Asp Pro Glu Val Val Gly Gln Leu Asp Arg
       1205             1210             1215

Trp Lys Thr Val Thr Ser Thr Pro Ala Ala Leu Pro Ala Pro Arg
       1220             1225             1230

Pro Asp Val Asp Thr Tyr Ala Ser Ala Gly Arg Leu Ser Val Glu
       1235             1240             1245

Leu Asp Ala Glu Thr Thr Ala Met Leu Leu Gly Glu Val Pro Ala
       1250             1255             1260
```

-continued

Ala Phe His Ala Gly Ile His Asp Ile Leu Leu Ile Ala Phe Gly
1265                1270                1275

Leu Ala Trp Thr Glu Phe Leu Gly Glu Pro Gly Ala Pro Ile Gly
1280                1285                1290

Ile Asp Val Glu Gly His Gly Arg His Glu Glu Leu Gly Ala Asp
1295                1300                1305

Ile Asp Leu Ser Arg Thr Val Gly Trp Phe Thr Ala Lys Tyr Pro
1310                1315                1320

Val Ser Leu Asp Val Ala Gly Leu Arg Trp Pro Gln Val Ala Ala
1325                1330                1335

Gly Asp Pro Ala Leu Gly Pro Val Leu Lys Arg Ala Lys Glu Gln
1340                1345                1350

Leu Arg Thr Leu Pro Glu Pro Leu Thr Tyr Gly Leu Leu Arg Tyr
1355                1360                1365

Leu Asn Thr Asp Val Asp Leu Ala Gly Ala Asp Pro Pro Ile Ala
1370                1375                1380

Phe Asn Tyr Leu Gly Arg Gln Gly Ala Ala Ser Asp Ser Ala Ala
1385                1390                1395

Asp Gly Trp Arg Ile Ser Gln Asp Met Ser Leu Leu Gly Ala Ala
1400                1405                1410

Ala Ala Val Pro Met Pro Leu Met His Ala Val Glu Leu Asn Ala
1415                1420                1425

Gly Thr Ile Asp Thr Gly Ala Gly Pro His Leu His Ala Glu Trp
1430                1435                1440

Thr Trp Ala Pro Ser Val Leu Gly Ala Glu Gln Ile Thr Arg Val
1445                1450                1455

Ser Arg Leu Trp Phe Glu Ala Leu Ala Gly Val Cys Ala His Val
1460                1465                1470

Arg Ser Gly Gly Gly Gly Gly Leu Thr Pro Ser Asp Ile Ala Pro
1475                1480                1485

Ala Arg Leu Thr Gln Gln Gln Ile Asp Glu Leu Gln Ser Arg His
1490                1495                1500

Arg Ile Ala Asp Ile Leu Pro Leu Thr Pro Leu Gln Gln Gly Leu
1505                1510                1515

Leu Phe His Ser Ser Thr Ala Gln Gly Asn Asp Gly Met Asp Asp
1520                1525                1530

Met Tyr Ala Val Gln Leu Asp Phe Thr Leu Thr Gly Pro Leu Asp
1535                1540                1545

Ala Asp Arg Leu Arg Glu Ala Val Arg Thr Val Val His Arg His
1550                1555                1560

Pro His Leu Ala Ala Leu Phe Cys Asp Gln Tyr Asp Glu Pro Val
1565                1570                1575

Gln Ile Ile Pro Ala Asp Pro Ala Val Glu Trp Arg Tyr Val Glu
1580                1585                1590

Leu Asp Gly Thr Gly Ala Ala Asp Ala Asp Asp Leu Ile Glu Gln
1595                1600                1605

Leu Cys Ala Ala Glu Arg Ala Ala Val Ala Asp Leu Ala Gly Gln
1610                1615                1620

Pro Val Phe Arg Thr Ala Leu Val Arg Thr Gly Gly Asp Arg His
1625                1630                1635

Arg Phe Val Leu Thr Ser His His Ile Leu Leu Asp Gly Trp Ser
1640                1645                1650

```
Leu Pro Ile Leu Leu Arg Glu Ile Phe Ala Gly Tyr Tyr Gly Gln
1655                1660                1665

Arg Leu Pro Ala Ala Gly Ser Tyr Arg Ala Phe Leu Thr Trp Leu
1670                1675                1680

Ala Glu Arg Asp Leu Asp Ala Ala Arg Arg Ala Trp Gly Glu Val
1685                1690                1695

Leu Ser Gly Phe Asp Thr Pro Thr Leu Val Ala Pro Glu Gly Arg
1700                1705                1710

Leu Gly Gln Gly Arg Arg Gly Phe Glu Lys Ser Cys Val Pro Glu
1715                1720                1725

Gln Thr Thr Arg Ala Leu Gly Glu Leu Ala Arg Ser Cys His Thr
1730                1735                1740

Thr Leu Ser Thr Val Leu Gln Ala Ala Trp Ala Val Val Leu Thr
1745                1750                1755

Ser Leu Thr Gly Arg His Asp Val Val Phe Gly Thr Pro Arg Ser
1760                1765                1770

Arg Val Gly Gln Leu Glu Val Asp Asp Ala Glu Gln Met Val Gly
1775                1780                1785

Leu Leu Ile Asn Thr Val Pro Val Arg Ala Glu Ile Thr Ala Thr
1790                1795                1800

Thr Thr Thr Ala Gln Leu Leu Ala Gln Leu Gln Asn Ser His Asn
1805                1810                1815

Asp Thr Leu Glu His Gln His Leu Ala Leu Asn Glu Ile His Arg
1820                1825                1830

Val Thr Gly His Asp Gln Leu Phe Asp Thr Leu Phe Val Tyr Glu
1835                1840                1845

Asn Tyr Pro Ile Asp Ser Gly Met Thr Leu Gly Ala Asp Gly Leu
1850                1855                1860

Ala Ile Ala Glu Phe Thr Asn Arg Glu Tyr Asn His Tyr Pro Leu
1865                1870                1875

Thr Val Glu Ala Leu Pro Gly Pro Glu Leu Gly Leu His Ile Glu
1880                1885                1890

Phe Asp Thr Asp Val Phe Asp Thr Ala Ser Ile Glu Ser Leu Val
1895                1900                1905

Gln Arg Leu Gln Arg Val Leu Val Ala Met Ser Thr Asp Pro Asp
1910                1915                1920

Arg Arg Leu Ser Ser Leu Asp Leu Leu Asp Arg Gly Glu Arg Glu
1925                1930                1935

Leu Val Leu Ser Thr Met Ser Gly Ala Gly Val Ser Ala Pro Ile
1940                1945                1950

Gly Val Ala Pro Gln Leu Leu Ala Ala Ala Val Ala Ala Asp Pro
1955                1960                1965

Asp Ala Pro Ala Ile Val Asp Gly Ala Arg Glu Leu Ser Tyr Arg
1970                1975                1980

Glu Leu Asp Asp Trp Ser Thr Arg Leu Ala Arg Lys Leu Ile Gln
1985                1990                1995

His Gly Val Gly Pro Glu His Ala Ala Gly Val Ala Ile Glu Arg
2000                2005                2010

Cys Ala Glu Leu Val Val Ala Trp Trp Ala Val Thr Lys Val Gly
2015                2020                2025

Gly Val Tyr Ala Pro Val Asn Leu Asp His Pro Val Glu Arg Ile
2030                2035                2040

Ala Ser Val Leu Asp Thr Val Asn Ala Val Cys Val Leu Thr Cys
```

-continued

```
            2045                2050               2055
Gly Thr Asp Glu Val Ala Gly Ala Gly Pro Arg Pro Ile Leu Arg
        2060                2065               2070

Ile Asp Gly Leu Asp Leu Ser Gly His Ser Thr Glu Pro Ile Thr
    2075                2080               2085

Asp Ala Asp Arg Arg Ser Pro Leu Arg Ala Asp Asp Thr Ala Tyr
        2090                2095               2100

Leu Ile Phe Thr Ser Gly Ser Thr Gly Val Pro Lys Gly Val Ala
        2105                2110               2115

Val Ser His Thr Gly Leu Leu Gly Trp Ala Ala Ala Gln Arg Glu
        2120                2125               2130

Leu Phe Gly Leu Gly Ala Asp Ala Arg Val Leu Met Val Ala Ser
        2135                2140               2145

Pro Thr Phe Asp Ala Ser Val Gly Glu Leu Leu Leu Ala Ala Gly
        2150                2155               2160

Ser Gly Ala Ala Leu Ile Val Ala Pro Pro Gln Val Tyr Ala Gly
        2165                2170               2175

Glu Ala Leu Thr Ala Leu Leu His Asn Gln Arg Val Gly Thr Ala
        2180                2185               2190

Ile Leu Thr Pro Thr Val Ile Ser Thr Leu Asp Arg Gly Arg Leu
        2195                2200               2205

Asp Gly Leu His Thr Leu Val Ala Val Gly Glu Ala Cys Leu Pro
        2210                2215               2220

Glu Leu Val Asp Gly Trp Ala Pro Gly Arg Gln Met Phe Asn Gly
        2225                2230               2235

Tyr Gly Pro Ser Glu Thr Thr Ile Trp Val Thr Cys Ala Arg Leu
        2240                2245               2250

Thr Ala Gly His Pro Val Arg Ile Gly Ala Pro Ile Pro Gly Val
        2255                2260               2265

Cys Ala Arg Val Leu Asp Gly Trp Leu Lys Pro Val Pro Val Gly
        2270                2275               2280

Val Val Gly Glu Leu Tyr Leu Ser Gly Pro Ala Leu Gly His Gly
        2285                2290               2295

Tyr Leu Gly Arg Val Asp Leu Thr Ala Glu Arg Phe Val Ala Asn
        2300                2305               2310

Pro Phe Gly Gly Pro Gly Glu Arg Met Tyr Arg Thr Gly Asp Leu
        2315                2320               2325

Val Arg Trp Thr Pro Glu Gly Thr Leu Asp Tyr Leu Gly Arg Ala
        2330                2335               2340

Asp Asn Gln Ile Lys Leu Arg Gly Gln Arg Ile Glu Leu Gly Glu
        2345                2350               2355

Ile Glu Asn Thr Leu Leu Ala Cys Pro Gln Val Thr Gln Ala Ala
        2360                2365               2370

Val Thr Val Gln Asp Ser Ala Ala Gly Ser Gln Leu Val Ala Tyr
        2375                2380               2385

Val Thr Leu Asp His Gly Pro Ser Asp Ala Asp Val Arg His Asp
        2390                2395               2400

Thr Asp Asp Ala Asp Asp Val Ala Gln Trp Arg His Leu Tyr Asp
        2405                2410               2415

Asp Leu Tyr Gly Ala Asp Leu Ala Ala Thr Phe Gly Glu Asp Phe
        2420                2425               2430

Arg Gly Trp Asn Ser Ser Tyr Thr Gly Glu Pro Ile Pro Leu Gln
        2435                2440               2445
```

```
Glu Met Ala Glu Trp Arg Ser Ala Thr Val Asp Arg Ile Met Ser
2450                2455                2460

Leu Arg Pro Arg Val Leu Glu Ile Gly Ala Gly Ser Gly Leu
2465                2470                2475

Leu Leu Ser Gln Ile Ala Pro Arg Cys Asp Arg Tyr Val Ala Thr
2480                2485                2490

Asp Phe Ser Ala Val Ala Ile Asp Asn Leu Ala Arg Ser Met Glu
2495                2500                2505

Gln Leu Gln Leu Pro Trp Arg Asp Arg Val Glu Leu Leu Thr Gln
2510                2515                2520

Pro Ala His Val Thr Asp Gly Leu Pro Pro Gly His Phe Asp Thr
2525                2530                2535

Ile Val Ile Asn Ser Val Val Gln Tyr Phe Pro Asn Ala Gly Tyr
2540                2545                2550

Leu Ala Asp Val Ile Asp Asn Ala Leu Glu Leu Leu Ala Pro Gly
2555                2560                2565

Gly Ser Leu Phe Ile Gly Asp Val Arg Asn His Ala Leu Gln Gly
2570                2575                2580

Ala Phe Gln Thr Gly Ile Ala Leu Ala Arg Gly Gly Gly Ala Asp
2585                2590                2595

Ala Ala Glu Ile Arg Gln Arg Val Arg His Ala Met Leu Gly Glu
2600                2605                2610

Thr Glu Leu Leu Leu Ala Pro Glu Phe Phe Thr Asn Trp Ala Asp
2615                2620                2625

Ser Arg Pro Ala Ala Ala Gly Leu Asp Ile Gln Leu Lys Arg Gly
2630                2635                2640

Leu Ser Asp Asn Glu Leu Asn Arg Tyr Arg Tyr Asp Val Val Ile
2645                2650                2655

His Lys Ala Pro Ala Pro Val Arg Ser Val Ala Ala Ala Pro Thr
2660                2665                2670

Trp Ser Trp Thr Asp Cys Thr Asp Cys Ala Gly Leu Arg Asp Gln
2675                2680                2685

Leu Ala Ala Arg Arg Pro Ala Val Val Arg Val Thr Asp Ile Pro
2690                2695                2700

Gln Ala Gly Val Ile Asp Asp Val Arg Val Glu Ala Ala Leu Ala
2705                2710                2715

Ala Gly Leu Pro Val Ala Asp Ala Leu Ala Ala Ala Gly Ser Asp
2720                2725                2730

Thr Ala Ala Ala Val Ala Glu Glu Leu His Arg Val Gly Glu Ala
2735                2740                2745

Thr Gly Tyr Arg Val Ala Val Thr Trp Gly Ala Gln Pro Gly Thr
2750                2755                2760

Leu Ser Ala Val Phe Val Gln Asp Gly Asp Gln Ala Ala Glu Pro
2765                2770                2775

Leu Thr Asp Leu Tyr Leu Pro Pro Ala Gly Ala Arg Gln Arg Thr
2780                2785                2790

Arg His Ala Asn Asp Pro Arg Ala Asn Thr Lys Ile Ala Gln Val
2795                2800                2805

Arg Glu Arg Leu Asn Ala Trp Leu Pro Glu Tyr Met Val Pro Thr
2810                2815                2820

His Ile Val Ala Leu Asp Glu Phe Pro Met Thr Thr Ser Gly Lys
2825                2830                2835
```

-continued

Leu Asp Arg Lys Ala Leu Pro Ala Pro Asp Tyr Gln Asp Ala Asp
2840            2845            2850

Arg Tyr Arg Ala Pro Ser Thr Ala Val Glu Glu Ile Leu Val Gly
2855            2860            2865

Ile Tyr Gly Gln Val Leu Gly Leu Glu Arg Val Gly Val Asp Asp
2870            2875            2880

Ser Phe Phe Asp Leu Gly Gly Asp Ser Leu Ser Ala Met Arg Leu
2885            2890            2895

Ile Ala Ala Val Asn Ala Ser Leu Asn Thr Asp Leu Gly Val Arg
2900            2905            2910

Thr Val Phe Glu Ala Pro Thr Ala Ala Glu Leu Ala Leu Arg Val
2915            2920            2925

Gly Ser Glu Ala Asp Arg Pro Glu Pro Leu Val Ala Gly Glu Arg
2930            2935            2940

Pro Ala Val Ile Pro Leu Ser Phe Ala Gln Thr Arg Leu Trp Phe
2945            2950            2955

Ile Asp Gln Phe Gln Gly Pro Ser Pro Met Tyr Asn Ile Thr Val
2960            2965            2970

Ala Leu Arg Leu Ser Gly Arg Leu Asp Ala Asp Ala Leu Arg Ala
2975            2980            2985

Ala Leu Ala Asp Val Val Ala Arg His Glu Ser Leu Arg Thr Val
2990            2995            3000

Phe Ala Thr Ala Asp Gly Thr Pro Gln Gln Val Val Ile Pro Ala
3005            3010            3015

Asp Arg Ile Gly Phe Ala Cys Asp Val Val Asp Ala Arg Gly Trp
3020            3025            3030

Pro Glu Asp Arg Leu Arg Glu Ala Met Ser Ala Ala Ala Arg Tyr
3035            3040            3045

Thr Phe Asp Leu Ser Ala Glu Ser Pro Leu His Thr Glu Leu Phe
3050            3055            3060

Ala Arg Gly Asp Asp Glu His Val Leu Val Val Ala Val His His
3065            3070            3075

Ile Ala Ala Asp Gly Trp Ser Ile Thr Pro Phe Ala Arg Asp Leu
3080            3085            3090

Gly Val Ala Tyr Ala Ser Arg Cys Ala Gly Arg Asp Pro Asp Trp
3095            3100            3105

Ala Pro Leu Pro Val Gln Tyr Ala Asp Tyr Thr Leu Trp Gln Arg
3110            3115            3120

Ala His Leu Gly Asp Val Asp Pro Gly Ser Arg Ile Ala Ala
3125            3130            3135

Gln Leu Asp Phe Trp Thr Asp Ala Leu Ala Gly Leu Pro Glu Arg
3140            3145            3150

Leu Gln Leu Pro Thr Asp Arg Pro Tyr Pro Ala Val Ala Asp His
3155            3160            3165

Arg Gly Ala Arg Leu Ala Val Asp Trp Pro Ala Glu Leu Gln Gln
3170            3175            3180

Arg Ile Gly Asp Val Ala His Arg His Asn Ala Thr Ser Phe Met
3185            3190            3195

Val Ile Gln Thr Ala Leu Thr Val Leu Leu Ala Lys Leu Gly Ala
3200            3205            3210

Asn Pro Asp Val Ala Val Gly Phe Pro Ile Ala Gly Arg Arg Asp
3215            3220            3225

Pro Ala Leu Asp Asp Leu Val Gly Phe Phe Val Asn Thr Leu Val

```
                3230                3235                3240

Leu Arg Val Asp Ala Ala Gly Asp Pro Ser Phe Thr Glu Leu Leu
    3245                3250                3255

Ala Arg Val Arg Thr Arg Ser Leu Glu Ala Phe Glu His Gln Asp
    3260                3265                3270

Val Pro Phe Glu Val Leu Val Glu Arg Leu Asn Pro Thr Arg Ser
    3275                3280                3285

Leu Thr His His Pro Leu Val Gln Val Met Leu Ala Trp Gln Asn
    3290                3295                3300

Phe Ala Gly Gln Asp Thr Gly Pro Ala Ala Gly Leu Ser Leu Gly
    3305                3310                3315

Asp Val Glu Ile Thr Pro Ile Pro Val Asp Thr His Thr Ala Arg
    3320                3325                3330

Met Asp Leu Thr Phe Ser Val Gly Glu Arg Trp Cys Glu Ser Gly
    3335                3340                3345

Glu Pro Gly Gly Ile Gly Gly Thr Val Glu Phe Arg Thr Asp Val
    3350                3355                3360

Phe Asp Pro Asp Ser Ile Gln Thr Leu Ile Gly Arg Leu Arg Arg
    3365                3370                3375

Val Leu Glu Ala Met Thr Asp Asp Pro Thr Gln Ser Val Trp Ser
    3380                3385                3390

Val Asp Leu Leu Asp Ala Gly Glu His Ala Arg Leu Asp Thr Leu
    3395                3400                3405

Gly Asn Arg Ala Ala Leu Thr Gly Pro Pro Arg Phe Asp Ser
    3410                3415                3420

Leu Pro Thr Leu Phe Ala Glu Gln Ala Ala Arg Thr Pro Asp Ala
    3425                3430                3435

Val Ala Leu Val Cys Gly Gly Arg Arg Met Thr Tyr Arg Glu Leu
    3440                3445                3450

Asp Glu Ala Ala Asn Arg Val Ala His Leu Leu Arg Val Arg Gly
    3455                3460                3465

Ala Gly Pro Gly His Thr Val Ala Leu Leu Phe Ser Arg Ser Ala
    3470                3475                3480

Glu Ala Ile Val Ala Ile Leu Gly Val Leu Lys Ser Gly Ala Ala
    3485                3490                3495

Tyr Leu Pro Ile Asp Pro Ala Leu Pro Gly Glu Arg Ile Gly Phe
    3500                3505                3510

Met Leu Ala Asp Ala Ala Pro Met Val Ala Ile Ser Thr Ala Glu
    3515                3520                3525

Leu Ala Pro Arg Leu His Gly Gln His Asp Val Pro Val Ile Asp
    3530                3535                3540

Val His Asp Pro Ala Ile Glu Ala Ala Pro Ser Ser Ala Leu Pro
    3545                3550                3555

Pro Pro Gly Ala Asp Asp Ile Ala Tyr Leu Ile Tyr Thr Ser Gly
    3560                3565                3570

Thr Thr Gly Val Pro Lys Gly Val Ala Val Ser His Arg Asn Val
    3575                3580                3585

Thr Gln Leu Leu Thr Ala Asp Ser Gly Leu Pro Arg Glu Gly Val
    3590                3595                3600

Trp Ser Gln Trp His Ser Leu Ala Phe Asp Val Ser Val Trp Glu
    3605                3610                3615

Ile Phe Gly Ala Leu Leu His Gly Gly Arg Leu Val Val Ile Pro
    3620                3625                3630
```

-continued

```
Asp Ser Val Val Arg Ser Pro Asp Asp Phe His Ala Leu Leu Leu
3635                3640                3645

Asp Glu Gln Val Ser Val Leu Ser Gln Thr Pro Ser Ala Ala Gly
3650                3655                3660

Thr Leu Ser Pro Glu Gly Leu Glu Asp Leu Thr Leu Val Val Ala
3665                3670                3675

Gly Glu Ala Cys Pro Ala Glu Leu Val Asp Arg Trp Ala Pro Gly
3680                3685                3690

Arg Thr Met Ile Asn Ala Tyr Gly Pro Thr Glu Ala Thr Val Tyr
3695                3700                3705

Thr Ala Ile Ser Ala Pro Leu Gln Pro Gly Ser Pro Ala Gly Val
3710                3715                3720

Pro Ile Gly Phe Pro Val Pro Gly Ala Gly Leu Phe Val Leu Asp
3725                3730                3735

Glu Ser Leu Arg Pro Val Pro Pro Gly Val Val Gly Glu Leu Tyr
3740                3745                3750

Val Gly Gly Ala Gly Val Ala Cys Gly Tyr Trp Arg Arg Gly Gly
3755                3760                3765

Leu Thr Ala Ser Trp Phe Val Ala Cys Pro Phe Gly Ala Pro Gly
3770                3775                3780

Ala Arg Met Tyr Arg Thr Gly Asp Leu Val Cys Trp Arg Ser Asp
3785                3790                3795

Gly Gln Leu Asp Tyr Arg Gly Arg Ala Asp Glu Gln Val Lys Val
3800                3805                3810

Arg Gly Tyr Arg Ile Glu Leu Gly Glu Val Gln Ala Ala Leu Ala
3815                3820                3825

Gly Leu Asp Asp Val Glu Gln Ala Val Val Ile Ala Arg Glu Asp
3830                3835                3840

Arg Pro Gly Gly Lys Arg Leu Val Gly Tyr Ile Thr Gly Thr Ala
3845                3850                3855

Asp Pro Ala Glu Val Arg Thr Ala Leu Ala Gln Arg Leu Pro Val
3860                3865                3870

Tyr Met Val Pro Ala Ala Val Ala Leu Asp Ala Ile Pro Leu
3875                3880                3885

Thr Pro Asn Gly Lys Leu Asp Thr Arg Ala Leu Pro Thr Pro Glu
3890                3895                3900

Tyr Thr Gly Ser Arg Tyr Arg Ala Pro Ser Asn Ala Val Glu Glu
3905                3910                3915

Thr Val Ala Gly Ile Tyr Ala His Val Leu Gly Val Glu Arg Val
3920                3925                3930

Gly Val Asp Asp Ser Phe Phe Asp Leu Gly Gly Asp Ser Ile Ser
3935                3940                3945

Ala Met Arg Val Ile Thr Ala Ile Asn Ala Ser Leu Gly Val Glu
3950                3955                3960

Leu Ala Val Arg Thr Leu Phe Glu Ala Pro Thr Val Ala Ser Leu
3965                3970                3975

Ser Trp Arg Ala Gln Thr Asp Thr Ala Arg Gly Gln Ala Glu
3980                3985                3990

Glu Ile Val Pro Val Gln Thr Leu Lys Glu Gly Thr Gly Ala Pro
3995                4000                4005

Leu Phe Cys Ile His Ala Ala Gly Gly Leu Ser Trp Ser Tyr Gln
4010                4015                4020
```

-continued

Val Leu Gly Asn His Leu Asp Cys Pro Ile Ile Gly Ile Gln Gln
4025                4030                4035

Ala Glu Pro Gln His Ala Ala Pro Arg Ser Ile Arg Glu Met Ala
4040                4045                4050

Gln Ser Tyr Ala Asp Arg Ile Gln Glu Thr Tyr Pro Asp Gly Pro
4055                4060                4065

Tyr His Leu Val Gly Trp Ser Phe Gly Gly Val Val Ala His Glu
4070                4075                4080

Leu Ala Ile Glu Leu Gln Arg Arg Gly Cys Ala Ile Ala Arg Leu
4085                4090                4095

Val Leu Leu Asp Ala Gln Pro Gly Leu Asp Gly Ser Val Thr Ala
4100                4105                4110

Pro Asp Ala Ala Leu Ala Glu Gln His Met Met Glu Glu Ala Leu
4115                4120                4125

Arg Ser His Leu Ala Ala Ala Asp His Asp Gln Pro His Ala His
4130                4135                4140

Arg Gln Phe Asn Gln Leu Val Arg Glu Ala Gly Ala Glu Gly Met
4145                4150                4155

Ser Arg His Lys Arg Leu Phe Asp Val Leu Phe Gly Asn Ala Arg
4160                4165                4170

Asn Asn Ile Glu Arg Ser Lys Ile His Glu Pro Gly Val Phe Leu
4175                4180                4185

Gly Asp Val Thr Ile Phe Ser Ala Val Arg Asp His Glu Asp Arg
4190                4195                4200

Ser Ala Phe Leu Ala Glu Asn Trp Arg Pro Tyr Val Ala Gly Asp
4205                4210                4215

Ile Val Ile His Glu Ile Asp Cys Thr His Asp Glu Ile Leu Asn
4220                4225                4230

Ala Asp Val Val Asp Ser Tyr Gly Gln Arg Leu Gly Gln Leu Leu
4235                4240                4245

Gly Ala Gln Arg Arg Arg Glu Leu Thr Pro Pro Gln Arg Phe Gly
4250                4255                4260

Ala Asp Pro Gly Asp Glu Pro Pro Val Arg
4265                4270

<210> SEQ ID NO 17
<211> LENGTH: 4273
<212> TYPE: PRT
<213> ORGANISM: Mycobacterium avium

<400> SEQUENCE: 17

Val Lys Arg Gly Asp Arg Ala Tyr Pro Val Thr Arg Gly Gln Leu Asp
1               5                   10                  15

Ile Trp Leu Ala Glu Gln Thr Gly His Leu Asp Val Ala Trp Gln Leu
                20                  25                  30

Gly Val Leu Val Arg Ile Asp Gly Ala Ile Asp Pro Ala Leu Leu His
            35                  40                  45

Gln Thr Met Arg His Val Val Gly Glu Ala Glu Ser Leu Arg Ala Ser
        50                  55                  60

Phe Phe Glu Ala Asp Gly Gln Val Phe Gln Lys Ala Val Glu Tyr Ser
65                  70                  75                  80

Asp Val Asp Leu Thr Phe Tyr Asp Leu Ser Gly Ser Ser Asp Pro Glu
                85                  90                  95

Arg Glu Val Arg Glu Met Thr Ala Ser Ile Gln Arg Thr Pro Met Pro
                100                 105                 110

```
Leu Thr Gly Pro Met Thr Lys Phe Ala Leu Phe Arg Thr Gly Ser Ala
            115                 120                 125

Glu Tyr Tyr Trp Phe Thr Thr Cys His His Ile Ala Ile Asp Gly Met
        130                 135                 140

Gly Ile Ala Leu Val Gly Arg Ile Ala Ala Val Tyr Thr Ala Leu
145                 150                 155                 160

Ala Ser Gly Lys Pro Ile Pro Pro Ala Phe Phe Gly Ser Leu Gln Asp
                165                 170                 175

Leu Val Gly Gly Glu Leu Glu Tyr Glu Ala Ser Ala Lys Phe Leu Glu
            180                 185                 190

Asp Lys Asp Tyr Trp Leu Ala His Arg Pro Gly Asp Gly Thr Ala Gly
        195                 200                 205

His Pro Pro Arg Pro Ala Asp Asp Gly Arg Asp Pro Tyr Ser Pro Ser
    210                 215                 220

Pro Pro Val Gln Leu Asp Glu Ser Val Ile Gly Ser Val Lys Glu Leu
225                 230                 235                 240

Ser Lys Ala Leu Gly Ile Arg Arg Ser Ser Val Leu Thr Ala Ala Cys
                245                 250                 255

Ala Leu Leu Val Arg Gly Trp Cys Ala Asp Gly Ser Asp Glu Val Val
            260                 265                 270

Leu Asp Phe Pro Val Ser Arg Arg Val Asp Pro Lys Ser Lys Thr His
        275                 280                 285

Pro Gly Met Leu Ala Gly Val Val Pro Leu Val Leu His Ala Pro Ala
    290                 295                 300

Ala Ala Thr Phe Ala Asp Phe Cys Arg His Val Asp Gln Arg Ser Arg
305                 310                 315                 320

Glu Ala Leu Arg His Gln Gln Phe Pro Thr Arg Thr Leu Asp Gly Glu
                325                 330                 335

Gly Asp Phe Ser Gly Pro Arg Gln Ala Pro Asn Arg Val Val Val Asn
            340                 345                 350

Phe Val Pro Ala Arg Leu Thr Leu Ser Leu Ala Asp Val Pro Ala Thr
        355                 360                 365

Ala Thr Tyr Thr Ser Phe Gly Pro Val Gly His Phe Gly Leu Phe Phe
    370                 375                 380

Leu Gly Phe Gly Asp Gln Gln Phe Leu Ser Thr Val Gly Thr Gly Gln
385                 390                 395                 400

Pro Leu Ala Asn Phe Asp Ala Thr Asp Leu Ala Glu Arg Leu Gln Arg
                405                 410                 415

Ile Leu Ala Ala Met Ala Ala Asp Pro Ala Arg Leu Leu Ser Ser Leu
            420                 425                 430

Asp Val Leu Arg Asp Pro Glu His Ala Gln Leu Glu Ala Leu Gly Asn
        435                 440                 445

Thr Ala Val Leu Thr Arg Thr Pro Gly Pro Ala Val Ser Val Pro Glu
    450                 455                 460

Leu Phe Ala Thr Gln Val Ala Arg Ala Pro Gln Asp Val Ala Leu Val
465                 470                 475                 480

Cys Glu Gly Arg Ser Leu Thr Tyr Arg Gln Leu Asp Glu Ala Ser Asn
                485                 490                 495

Arg Leu Ala His Leu Leu Ala Gly Leu Gly Ala Gly Pro Gly Gln Ser
            500                 505                 510

Val Ala Leu Leu Phe Ser Arg Ser Ala Glu Ala Ile Val Ala Ile Leu
        515                 520                 525
```

-continued

Gly Val Leu Lys Ser Gly Ala Ala Tyr Leu Pro Ile Asp Pro Ala Leu
        530                 535                 540

Pro Gly Glu Arg Ile Gly Phe Met Leu Ala Asp Ala Ala Pro Met Val
545                 550                 555                 560

Ala Ile Ser Thr Ala Glu Leu Ala Pro Arg Leu His Gly Gln His Asp
                565                 570                 575

Val Pro Val Ile Asp Val His Asp Pro Ala Ile Glu Ala Ala Pro Ser
            580                 585                 590

Ser Ala Leu Pro Pro Gly Ala Asp Asp Ile Ala Tyr Leu Ile Tyr
        595                 600                 605

Thr Ser Gly Thr Thr Gly Val Pro Lys Gly Val Ala Val Ser His Arg
    610                 615                 620

Asn Val Thr Gln Leu Leu Thr Ala Asp Ser Gly Leu Pro Arg Glu Gly
625                 630                 635                 640

Val Trp Ser Gln Trp His Ser Leu Ala Phe Asp Val Ser Val Trp Glu
                645                 650                 655

Ile Phe Gly Ala Leu Leu His Gly Gly Arg Leu Val Val Ile Pro Asp
            660                 665                 670

Ser Val Val Arg Ser Pro Asp Asp Phe His Ala Leu Leu Asp Glu
        675                 680                 685

Gln Val Ser Val Leu Ser Gln Thr Pro Ser Ala Ala Gly Thr Leu Ser
    690                 695                 700

Pro Glu Gly Leu Glu Asp Leu Thr Leu Val Val Ala Gly Glu Ala Cys
705                 710                 715                 720

Pro Ala Glu Leu Val Asp Arg Trp Ala Pro Gly Arg Thr Met Ile Asn
                725                 730                 735

Ala Tyr Gly Pro Thr Glu Thr Thr Met Cys Val Ala Ile Ser Ala Pro
            740                 745                 750

Leu Ala Pro Gly Met Gly Ser Pro Ile Gly Val Pro Val Asp Gly
        755                 760                 765

Ala Gly Leu Phe Val Leu Asp Ala Trp Leu Arg Pro Val Pro Pro Gly
    770                 775                 780

Val Val Gly Glu Leu Tyr Val Ala Gly Ala Gly Val Ala Cys Gly Tyr
785                 790                 795                 800

Trp Arg Arg Gly Gly Leu Thr Ala Ser Arg Phe Val Ala Cys Pro Phe
                805                 810                 815

Gly Ala Pro Gly Ala Arg Met Tyr Arg Thr Gly Asp Leu Val Cys Trp
            820                 825                 830

Arg Ser Asp Gly Gln Leu Asp Tyr Arg Gly Arg Ala Asp Glu Gln Val
        835                 840                 845

Lys Val Arg Gly Tyr Arg Ile Glu Leu Gly Glu Val Gln Ala Ala Leu
    850                 855                 860

Ala Ala Leu Asp Asp Val Asp Gln Ala Val Val Ile Ala Arg Glu Asp
865                 870                 875                 880

Arg Pro Gly Gly Lys Arg Leu Val Gly Tyr Ile Thr Gly Thr Ala Asp
                885                 890                 895

Pro Ala Glu Val Arg Thr Ala Leu Ala Gln Arg Leu Pro Val Tyr Met
            900                 905                 910

Val Pro Ala Ala Val Val Ala Leu Asp Ala Ile Pro Leu Thr Pro Asn
        915                 920                 925

Gly Lys Leu Asp Thr Arg Ala Leu Pro Thr Pro Glu Tyr Ser Thr Gly
    930                 935                 940

Glu Tyr Arg Ala Pro Glu Ser Pro Thr Glu Glu Ile Leu Ala Gly Ile

```
              945                 950                 955                 960

Tyr Ala Glu Val Leu Gly Val Glu Arg Val Gly Val Asp Glu Ser Phe
                         965                 970                 975

Phe Asp Leu Gly Gly Asp Ser Ile Ser Ala Met Arg Val Val Ala Arg
                         980                 985                 990

Ala Arg Ala Ala Gly Leu Thr Cys Arg Pro Arg Asp Val Phe Val Glu
                         995                 1000                1005

Gln Thr Val Ala Arg Leu Ala Arg Val Val Gly Ser Gly Asp Arg
                 1010                1015                1020

Ala Ala Glu Val Ala Asp Glu Gly Val Gly Pro Val Pro Pro Thr
                 1025                1030                1035

Pro Ile Met Arg Trp Leu Gln Ala Ala Glu Arg Ala Gly Gly Ala
                 1040                1045                1050

Thr Asp Gln Phe Asn Gln Thr Val Leu Val Gln Ala Pro Ala Gly
                 1055                1060                1065

Val Thr Glu Thr Glu Val Ala Ile Val Leu Gln Ala Leu Val Asp
                 1070                1075                1080

Arg His Ala Met Leu Arg Leu Arg Val Thr Asp Asp Gly Ala Asp
                 1085                1090                1095

Gly Trp Ser Phe Glu Val Pro Glu Ala Gly Ser Val Gln Ala Arg
                 1100                1105                1110

Asp Cys Leu Arg Ser Val Asp Ala Leu Ser Asp Glu Ala Leu Leu
                 1115                1120                1125

Ala Ala Arg Ala Arg Leu Asn Pro Ala Ala Gly Thr Met Leu Ala
                 1130                1135                1140

Ala Leu Trp Val Glu Ala Thr Gly Gln Leu Ala Val Ile Ile His
                 1145                1150                1155

His Leu Ala Val Asp Ala Val Ser Trp Trp Ile Leu Leu Glu Asp
                 1160                1165                1170

Leu Asn Ile Ala Trp Ala Leu His Arg Ala Gly Gln Pro Val Glu
                 1175                1180                1185

Leu Ala Pro Ala Gly Thr Ser Phe Ala Arg Trp Ala Arg Leu Leu
                 1190                1195                1200

Asp Glu His Ala Arg Asp Pro Glu Val Val Gly Gln Leu Asp Arg
                 1205                1210                1215

Trp Lys Thr Val Thr Ser Thr Pro Ala Ala Leu Pro Ala Pro Arg
                 1220                1225                1230

Pro Asp Val Asp Thr Tyr Ala Ser Ala Gly Arg Leu Ser Val Glu
                 1235                1240                1245

Leu Asp Ala Glu Thr Thr Ala Met Leu Leu Gly Glu Val Pro Ala
                 1250                1255                1260

Ala Phe His Ala Gly Ile His Asp Ile Leu Leu Ile Ala Phe Gly
                 1265                1270                1275

Leu Ala Trp Thr Glu Phe Leu Gly Glu Pro Gly Ala Pro Ile Gly
                 1280                1285                1290

Ile Asp Val Glu Gly His Gly Arg His Glu Glu Leu Gly Ala Asp
                 1295                1300                1305

Ile Asp Leu Ser Arg Thr Val Gly Trp Phe Thr Ala Lys Tyr Pro
                 1310                1315                1320

Val Ser Leu Asp Val Ala Gly Leu Arg Trp Pro Gln Val Ala Ala
                 1325                1330                1335

Gly Asp Pro Ala Leu Gly Pro Val Leu Lys Arg Ala Lys Glu Gln
                 1340                1345                1350
```

```
Leu Arg Thr Leu Pro Glu Pro Leu Thr Tyr Gly Leu Leu Arg Tyr
1355             1360                 1365

Leu Asn Thr Asp Val Asp Leu Ala Gly Ala Asp Pro Ile Ala
1370             1375                 1380

Phe Asn Tyr Leu Gly Arg Gln Gly Ala Ala Ser Asp Ser Ala Ala
1385             1390                 1395

Asp Gly Trp Arg Ile Ser Gln Asp Met Ser Leu Leu Gly Ala Ala
1400             1405                 1410

Ala Ala Val Pro Met Pro Leu Met His Ala Val Glu Leu Asn Ala
1415             1420                 1425

Gly Thr Ile Asp Thr Gly Ala Gly Pro His Leu His Ala Glu Trp
1430             1435                 1440

Thr Trp Ala Pro Ser Val Leu Gly Ala Glu Gln Ile Thr Arg Val
1445             1450                 1455

Ser Arg Leu Trp Phe Glu Ala Leu Ala Gly Val Cys Ala His Val
1460             1465                 1470

Arg Ser Gly Gly Gly Gly Leu Thr Pro Ser Asp Ile Ala Pro Ala
1475             1480                 1485

Arg Leu Thr Gln Gln Gln Ile Asp Glu Leu Gln Ser Arg His Arg
1490             1495                 1500

Ile Ala Asp Ile Leu Pro Leu Thr Pro Leu Gln Gln Gly Leu Leu
1505             1510                 1515

Phe His Ser Ser Thr Ala Gln Gly Asn Asp Gly Met Asp Asp Met
1520             1525                 1530

Tyr Ala Val Gln Leu Asp Phe Thr Leu Thr Gly Pro Leu Asp Ala
1535             1540                 1545

Asp Arg Leu Arg Glu Ala Val Arg Thr Val Val His Arg His Pro
1550             1555                 1560

His Leu Ala Ala Leu Phe Cys Asp Gln Tyr Asp Glu Pro Val Gln
1565             1570                 1575

Ile Ile Pro Ala Asp Pro Ala Val Glu Trp Arg Tyr Val Glu Leu
1580             1585                 1590

Asp Gly Thr Gly Ala Ala Asp Ala Asp Asp Leu Ile Glu Gln Leu
1595             1600                 1605

Cys Ala Ala Glu Arg Ala Ala Val Ala Asp Leu Ala Gly Gln Pro
1610             1615                 1620

Val Phe Arg Thr Ala Leu Val Arg Thr Gly Gly Asp Arg His Arg
1625             1630                 1635

Phe Val Leu Thr Ser His His Ile Leu Leu Asp Gly Trp Ser Leu
1640             1645                 1650

Pro Ile Leu Leu Arg Glu Ile Phe Ala Gly Tyr Tyr Gly Gln Arg
1655             1660                 1665

Leu Pro Ala Ala Gly Ser Tyr Arg Ala Phe Leu Thr Trp Leu Ala
1670             1675                 1680

Glu Arg Asp Leu Asp Ala Ala Arg Arg Ala Trp Gly Glu Val Leu
1685             1690                 1695

Ser Gly Phe Asp Thr Pro Thr Leu Val Ala Pro Glu Gly Arg Leu
1700             1705                 1710

Gly Gln Gly Arg Arg Gly Phe Glu Lys Ser Cys Val Pro Glu Gln
1715             1720                 1725

Thr Thr Arg Ala Leu Gly Glu Leu Ala Arg Ser Cys His Thr Thr
1730             1735                 1740
```

```
Leu Ser Thr Val Leu Gln Ala Ala Trp Ala Val Val Leu Thr Ser
    1745                1750                1755

Leu Thr Gly Arg His Asp Val Val Phe Gly Thr Pro Arg Ser Arg
    1760                1765                1770

Val Gly Gln Leu Glu Val Asp Asp Ala Glu Gln Met Val Gly Leu
    1775                1780                1785

Leu Ile Asn Ala Val Pro Val Arg Ala Glu Ile Thr Ala Thr Thr
    1790                1795                1800

Thr Thr Ala Gln Leu Leu Ala Gln Leu Gln Asn Ser His Asn Asp
    1805                1810                1815

Thr Leu Glu His Gln His Leu Ala Leu Asn Glu Ile His Arg Val
    1820                1825                1830

Thr Gly His Asp Gln Leu Phe Asp Thr Leu Phe Val Tyr Glu Asn
    1835                1840                1845

Tyr Pro Ile Asp Ser Gly Met Thr Leu Gly Ala Asp Gly Leu Ala
    1850                1855                1860

Ile Ala Glu Phe Thr Asn Arg Glu Tyr Asn His Tyr Pro Leu Thr
    1865                1870                1875

Val Glu Ala Leu Pro Gly Pro Glu Leu Gly Leu His Ile Glu Phe
    1880                1885                1890

Asp Thr Asp Val Phe Asp Thr Ala Ser Ile Glu Ser Leu Val Gln
    1895                1900                1905

Arg Leu Gln Arg Val Leu Val Ala Met Ser Thr Asp Pro Asp Arg
    1910                1915                1920

Arg Leu Ser Ser Leu Asp Leu Leu Asp Arg Gly Glu Arg Glu Leu
    1925                1930                1935

Val Leu Ser Thr Met Ser Gly Ala Gly Val Ser Ala Pro Ile Gly
    1940                1945                1950

Val Ala Pro Gln Leu Leu Ala Ala Val Ala Ala Asp Pro Asp
    1955                1960                1965

Ala Pro Ala Ile Val Asp Gly Ala Arg Glu Leu Ser Tyr Arg Glu
    1970                1975                1980

Leu Asp Asp Trp Ser Thr Arg Leu Ala Arg Lys Leu Ile Gln His
    1985                1990                1995

Gly Val Gly Pro Glu His Ala Ala Gly Val Ala Ile Glu Arg Cys
    2000                2005                2010

Ala Glu Leu Val Val Ala Trp Ala Val Thr Lys Ala Gly Gly
    2015                2020                2025

Val Tyr Ala Pro Val Asn Leu Asp Tyr Pro Val Glu Arg Ile Ala
    2030                2035                2040

Ser Val Leu Asp Thr Val Asn Ala Val Cys Val Leu Thr Cys Gly
    2045                2050                2055

Thr Asp Glu Val Ala Gly Ala Gly Pro Arg Pro Ile Leu Arg Ile
    2060                2065                2070

Asp Gly Leu Asp Leu Ser Gly His Ser Thr Glu Pro Ile Thr Asp
    2075                2080                2085

Ala Asp Arg Arg Ser Pro Leu Arg Ala Asp Asp Thr Ala Tyr Leu
    2090                2095                2100

Ile Phe Thr Ser Gly Ser Thr Gly Val Pro Lys Gly Val Ala Val
    2105                2110                2115

Ser His Thr Gly Leu Leu Gly Trp Ala Ala Ala Gln Arg Glu Leu
    2120                2125                2130

Phe Gly Leu Gly Ala Asp Ala Arg Val Leu Met Val Ala Ser Pro
```

```
                2135                2140                2145
Thr Phe Asp Ala Ser Val Gly Glu Leu Leu Ala Ala Gly Ser
        2150                2155                2160
Gly Ala Ala Leu Ile Val Ala Pro Pro Gln Val Tyr Ala Gly Glu
    2165                2170                2175
Ala Leu Thr Ala Leu Leu His Asn Gln Arg Val Gly Thr Ala Ile
    2180                2185                2190
Leu Thr Pro Thr Val Ile Ser Thr Leu Asp Arg Gly Arg Leu Asp
    2195                2200                2205
Gly Leu His Thr Leu Val Ala Val Gly Glu Ala Cys Leu Pro Glu
    2210                2215                2220
Leu Val Asp Gly Trp Ala Pro Gly Arg Gln Met Phe Asn Gly Tyr
    2225                2230                2235
Gly Pro Ser Glu Thr Thr Ile Trp Val Thr Cys Ala Arg Leu Thr
    2240                2245                2250
Ala Gly His Pro Val Arg Ile Gly Ala Pro Ile Pro Gly Val Cys
    2255                2260                2265
Ala Arg Val Leu Asp Gly Trp Leu Lys Pro Val Pro Val Gly Val
    2270                2275                2280
Val Gly Glu Leu Tyr Leu Ser Gly Pro Ala Leu Gly His Gly Tyr
    2285                2290                2295
Leu Gly Arg Val Asp Leu Thr Ala Glu Arg Phe Val Ala Asn Pro
    2300                2305                2310
Phe Gly Gly Pro Gly Glu Arg Met Tyr Arg Thr Gly Asp Leu Val
    2315                2320                2325
Arg Trp Thr Pro Glu Gly Thr Leu Asp Tyr Leu Gly Arg Ala Asp
    2330                2335                2340
Asn Gln Ile Lys Leu Arg Gly Gln Arg Ile Glu Leu Gly Glu Ile
    2345                2350                2355
Glu Asn Thr Leu Leu Ala Cys Pro Gln Val Thr Gln Ala Ala Val
    2360                2365                2370
Thr Val Gln Asp Ser Ala Ala Gly Ser Gln Leu Val Ala Tyr Val
    2375                2380                2385
Thr Leu Asp His Gly Pro Ser Asp Ala Asp Val Arg His Asp Thr
    2390                2395                2400
Asp Asp Ala Asp Asp Val Ala Gln Trp Arg His Leu Tyr Asp Asp
    2405                2410                2415
Leu Tyr Gly Ala Asp Leu Ala Ala Thr Phe Gly Glu Asp Phe Arg
    2420                2425                2430
Gly Trp Asn Ser Ser Tyr Thr Gly Glu Pro Ile Pro Leu Gln Glu
    2435                2440                2445
Met Ala Glu Trp Arg Ser Ala Thr Val Asp Arg Ile Met Ser Leu
    2450                2455                2460
Arg Pro Arg Arg Val Leu Glu Ile Gly Ala Gly Ser Gly Leu Leu
    2465                2470                2475
Leu Ser Gln Ile Ala Pro Arg Cys Asp Arg Tyr Val Ala Thr Asp
    2480                2485                2490
Phe Ser Ala Val Ala Ile Asp Asn Leu Ala Arg Ser Met Glu Gln
    2495                2500                2505
Leu Gln Leu Pro Trp Arg Asp Arg Val Glu Leu Leu Thr Gln Pro
    2510                2515                2520
Ala His Val Thr Asp Gly Leu Pro Pro Gly His Phe Asp Thr Ile
    2525                2530                2535
```

```
Val Ile Asn Ser Val Val Gln  Tyr Phe Pro Asn Ala  Gly Tyr Leu
    2540            2545                 2550

Ala Asp Val Ile Asp Asn Ala  Leu Glu Leu Leu Ala  Pro Gly Gly
    2555            2560                 2565

Ser Leu Phe Ile Gly Asp Val  Arg Asn His Ala Leu  Gln Gly Ala
    2570            2575                 2580

Phe Gln Thr Gly Ile Ala Leu  Ala Arg Gly Gly Gly  Ala Asp Ala
    2585            2590                 2595

Ala Glu Ile Arg Gln Arg Val  Arg His Ala Met Leu  Gly Glu Thr
    2600            2605                 2610

Glu Leu Leu Leu Ala Pro Glu  Phe Phe Thr Asn Trp  Ala Asp Ser
    2615            2620                 2625

Arg Pro Ala Ala Ala Gly Leu  Asp Ile Gln Leu Lys  Arg Gly Leu
    2630            2635                 2640

Ser Asp Asn Glu Leu Asn Arg  Tyr Arg Tyr Asp Val  Val Ile His
    2645            2650                 2655

Lys Ala Pro Ala Pro Val Arg  Ser Val Ala Ala Ala  Pro Thr Trp
    2660            2665                 2670

Ser Trp Thr Asp Cys Thr Asp  Cys Ala Gly Leu Arg  Asp Gln Leu
    2675            2680                 2685

Ala Ala Arg Arg Pro Ala Val  Val Arg Val Thr Asp  Ile Pro Gln
    2690            2695                 2700

Ala Gly Val Ile Asp Asp Val  Arg Val Glu Ala Ala  Leu Ala Ala
    2705            2710                 2715

Gly Leu Pro Val Ala Asp Ala  Leu Ala Ala Ala Gly  Ser Asp Thr
    2720            2725                 2730

Ala Ala Ala Val Ala Glu Glu  Leu His Arg Val Gly  Glu Ala Thr
    2735            2740                 2745

Gly Tyr Arg Val Ala Val Thr  Trp Gly Ala Gln Pro  Gly Thr Leu
    2750            2755                 2760

Ser Ala Val Phe Val Gln Asp  Gly Asp Gln Ala Ala  Glu Pro Leu
    2765            2770                 2775

Thr Asp Leu Tyr Leu Pro Pro  Ala Gly Ala Arg Gln  Arg Thr Arg
    2780            2785                 2790

His Ala Asn Asp Pro Arg Ala  Asn Thr Lys Ile Ala  Gln Val Arg
    2795            2800                 2805

Glu Arg Leu Asn Ala Trp Leu  Pro Glu Tyr Met Val  Pro Thr His
    2810            2815                 2820

Ile Val Ala Leu Asp Glu Phe  Pro Met Thr Thr Ser  Gly Lys Leu
    2825            2830                 2835

Asp Arg Lys Ala Leu Pro Ala  Pro Asp Tyr Gln Asp  Ala Asp Arg
    2840            2845                 2850

Tyr Arg Ala Pro Ser Thr Ala  Val Glu Glu Ile Leu  Val Gly Ile
    2855            2860                 2865

Tyr Gly Gln Val Leu Gly Leu  Glu Arg Val Gly Val  Asp Asp Ser
    2870            2875                 2880

Phe Phe Asp Leu Gly Gly Asp  Ser Leu Ser Ala Met  Arg Leu Ile
    2885            2890                 2895

Ala Ala Val Asn Ala Ser Leu  Asn Thr Asp Leu Gly  Val Arg Thr
    2900            2905                 2910

Val Phe Glu Ala Pro Thr Ala  Ala Glu Leu Ala Leu  Arg Val Gly
    2915            2920                 2925
```

-continued

| | | | | | | | | | | | |
|---|---|---|---|---|---|---|---|---|---|---|---|
|Ser|Glu|Ala|Asp|Arg|Pro|Glu|Pro|Leu|Val|Ala|Gly|Glu|Arg|Pro|
| |2930| | | |2935| | | |2940| | | | | |

Ser Glu Ala Asp Arg Pro Glu Pro Leu Val Ala Gly Glu Arg Pro
    2930            2935            2940

Ala Val Ile Pro Leu Ser Phe Ala Gln Thr Arg Leu Trp Phe Ile
    2945            2950            2955

Asp Gln Phe Gln Gly Pro Ser Pro Met Tyr Asn Ile Thr Val Ala
    2960            2965            2970

Leu Arg Leu Ser Gly Arg Leu Asp Ala Asp Ala Leu Arg Ala Ala
    2975            2980            2985

Leu Ala Asp Val Val Ala Arg His Glu Ser Leu Arg Thr Val Phe
    2990            2995            3000

Ala Thr Ala Asp Ala Thr Pro Gln Gln Val Val Ile Pro Ala Asp
    3005            3010            3015

Arg Ile Gly Phe Ala Cys Asp Val Val Asp Ala Arg Gly Trp Pro
    3020            3025            3030

Glu Asp Arg Leu Arg Glu Ala Met Ser Ala Ala Ala Arg Tyr Thr
    3035            3040            3045

Phe Asp Leu Ser Ala Glu Ser Pro Leu His Thr Glu Leu Phe Ala
    3050            3055            3060

Arg Gly Asp Asp Glu His Val Leu Val Val Ala Val His His Ile
    3065            3070            3075

Ala Ala Asp Gly Trp Ser Ile Thr Pro Phe Ala Arg Asp Leu Gly
    3080            3085            3090

Val Ala Tyr Ala Ser Arg Cys Ala Gly Arg Asp Pro Asp Trp Ala
    3095            3100            3105

Pro Leu Pro Val Gln Tyr Ala Asp Tyr Thr Leu Trp Gln Arg Ala
    3110            3115            3120

His Leu Gly Asp Val Asp Pro Gly Ser Arg Ile Ala Ala Gln
    3125            3130            3135

Leu Asp Phe Trp Thr Asp Ala Leu Ala Gly Leu Pro Glu Arg Leu
    3140            3145            3150

Gln Leu Pro Thr Asp Arg Pro Tyr Pro Ala Val Ala Asp His Arg
    3155            3160            3165

Gly Ala Arg Leu Ala Val Asp Trp Pro Ala Glu Leu Gln Gln Arg
    3170            3175            3180

Ile Gly Asp Val Ala His Arg His Asp Ala Thr Ser Phe Met Val
    3185            3190            3195

Ile Gln Thr Ala Leu Thr Val Leu Leu Ala Lys Leu Gly Ala Asn
    3200            3205            3210

Pro Asp Val Ala Val Gly Phe Pro Ile Ala Gly Arg Arg Asp Pro
    3215            3220            3225

Ala Leu Asp Asp Leu Val Gly Phe Phe Val Asn Thr Leu Val Leu
    3230            3235            3240

Arg Val Asp Ala Ala Gly Asp Pro Ser Phe Thr Glu Leu Leu Ala
    3245            3250            3255

Arg Val Arg Thr Arg Ser Leu Glu Ala Phe Glu His Gln Asp Val
    3260            3265            3270

Pro Phe Glu Val Leu Val Glu Arg Leu Asn Pro Thr Arg Ser Leu
    3275            3280            3285

Thr His His Pro Leu Val Gln Val Met Leu Ala Trp Gln Asn Phe
    3290            3295            3300

Ala Gly Gln Asp Thr Gly Pro Ala Ala Gly Leu Ser Leu Gly Asp
    3305            3310            3315

Val Glu Ile Thr Pro Ile Pro Val Asp Thr His Thr Ala Arg Met

```
            3320                3325                3330

Asp Leu Thr Phe Ser Val Gly Glu Arg Trp Cys Glu Ser Gly Glu
    3335                3340                3345

Pro Gly Gly Ile Gly Gly Thr Val Glu Phe Arg Thr Asp Val Phe
    3350                3355                3360

Asp Pro Asp Ser Ile Gln Thr Leu Ile Gly Arg Leu Arg Arg Val
    3365                3370                3375

Leu Glu Ala Met Thr Asp Asp Pro Thr Gln Ser Val Trp Ser Val
    3380                3385                3390

Asp Leu Leu Asp Ala Gly Glu His Ala Arg Leu Asp Thr Leu Gly
    3395                3400                3405

Asn Arg Ala Ala Leu Thr Gly Pro Pro Arg Phe Asp Ser Leu
    3410                3415                3420

Pro Thr Leu Phe Ala Glu Gln Ala Ala Arg Thr Pro Asp Ala Val
    3425                3430                3435

Ala Leu Val Cys Gly Gly Arg Arg Met Thr Tyr Arg Glu Leu Asp
    3440                3445                3450

Glu Ala Ser Asn Arg Leu Ala His Leu Leu Ala Gly Leu Gly Ala
    3455                3460                3465

Gly Pro Gly Gln Ser Val Ala Leu Leu Phe Ser Arg Ser Ala Glu
    3470                3475                3480

Ala Ile Val Ala Ile Leu Gly Val Leu Lys Ser Gly Ala Ala Tyr
    3485                3490                3495

Leu Pro Ile Asp Pro Ala Leu Pro Gly Glu Arg Ile Gly Phe Met
    3500                3505                3510

Leu Ala Asp Ala Ala Pro Met Val Ala Ile Ser Thr Ala Glu Leu
    3515                3520                3525

Ala Pro Arg Leu His Gly Gln His Asp Val Pro Val Ile Asp Val
    3530                3535                3540

His Asp Pro Ala Ile Glu Ala Ala Pro Ser Ser Ala Leu Pro Pro
    3545                3550                3555

Pro Gly Ala Asp Asp Ile Ala Tyr Leu Ile Tyr Thr Ser Gly Thr
    3560                3565                3570

Thr Gly Val Pro Lys Gly Val Ala Val Ser His Arg Asn Val Thr
    3575                3580                3585

Gln Leu Leu Thr Ala Asp Ser Gly Leu Pro Arg Glu Gly Val Trp
    3590                3595                3600

Ser Gln Trp His Ser Leu Ala Phe Asp Val Ser Val Trp Glu Ile
    3605                3610                3615

Phe Gly Ala Leu Leu His Gly Gly Arg Leu Val Val Ile Pro Asp
    3620                3625                3630

Ser Val Val Arg Ser Pro Asp Asp Phe His Ala Leu Leu Leu Asp
    3635                3640                3645

Glu Gln Val Ser Val Leu Ser Gln Thr Pro Ser Ala Ala Gly Thr
    3650                3655                3660

Leu Ser Pro Glu Gly Leu Glu Asp Leu Thr Leu Val Val Ala Gly
    3665                3670                3675

Glu Ala Cys Pro Ala Glu Leu Val Asp Arg Trp Ala Pro Gly Arg
    3680                3685                3690

Thr Met Ile Asn Ala Tyr Gly Pro Thr Glu Ala Thr Val Tyr Thr
    3695                3700                3705

Ala Ile Ser Ala Pro Leu Gln Pro Gly Ser Pro Ala Gly Val Pro
    3710                3715                3720
```

```
Ile Gly Phe Pro Val Pro Gly Ala Gly Leu Phe Val Leu Asp Glu
3725                3730                3735

Ser Leu Arg Pro Val Pro Pro Gly Val Val Gly Glu Leu Tyr Val
3740                3745                3750

Ala Gly Ala Gly Val Ala Cys Gly Tyr Trp Arg Arg Gly Gly Leu
3755                3760                3765

Thr Ala Ser Arg Phe Val Ala Cys Pro Phe Gly Ala Pro Gly Ala
3770                3775                3780

Arg Met Tyr Arg Thr Gly Asp Leu Val Cys Trp Arg Ser Asp Gly
3785                3790                3795

Gln Leu Asp Tyr Arg Gly Arg Ala Asp Glu Gln Val Lys Val Arg
3800                3805                3810

Gly Tyr Arg Ile Glu Leu Gly Glu Val Gln Ala Ala Leu Ala Ala
3815                3820                3825

Leu Asp Asp Val Asp Gln Ala Val Val Ile Ala Arg Glu Asp Arg
3830                3835                3840

Pro Gly Gly Lys Arg Leu Val Gly Tyr Ile Thr Gly Thr Ala Asp
3845                3850                3855

Pro Ala Glu Val Arg Thr Ala Leu Ala Gln Arg Leu Pro Val Tyr
3860                3865                3870

Met Val Pro Ala Ala Val Val Ala Leu Asp Ala Ile Pro Leu Thr
3875                3880                3885

Pro Asn Gly Lys Leu Asp Thr Arg Ala Leu Pro Thr Pro Glu Tyr
3890                3895                3900

Thr Gly Ser Arg Tyr Arg Ala Pro Ser Asn Ala Val Glu Glu Thr
3905                3910                3915

Val Ala Gly Ile Tyr Ala His Val Leu Gly Val Glu Arg Val Gly
3920                3925                3930

Val Asp Asp Ser Phe Phe Asp Leu Gly Gly Asp Ser Ile Ser Ala
3935                3940                3945

Met Arg Val Ile Thr Ala Ile Asn Ala Ser Leu Gly Val Glu Leu
3950                3955                3960

Ala Val Arg Thr Leu Phe Glu Ala Pro Thr Val Ala Ser Leu Ser
3965                3970                3975

Trp Arg Ala Gln Thr Asp Thr Ala Arg Gly Gly Gln Ala Glu Glu
3980                3985                3990

Ile Val Pro Val Gln Thr Leu Lys Glu Gly Thr Gly Ala Pro Leu
3995                4000                4005

Phe Cys Ile His Ala Ala Gly Gly Leu Ser Trp Ser Tyr Gln Val
4010                4015                4020

Leu Gly Asn His Leu Asp Cys Pro Ile Ile Gly Ile Gln Gln Ala
4025                4030                4035

Glu Pro Gln His Ala Ala Pro Arg Ser Ile Arg Glu Met Ala Gln
4040                4045                4050

Ser Tyr Ala Asp Arg Ile Gln Glu Thr Tyr Pro Asp Gly Pro Tyr
4055                4060                4065

His Leu Val Gly Trp Ser Phe Gly Gly Val Val Ala His Glu Leu
4070                4075                4080

Ala Ile Glu Leu Gln Arg Arg Gly Cys Ala Ile Ala Arg Leu Val
4085                4090                4095

Leu Leu Asp Ala Gln Pro Gly Leu Asp Gly Ser Val Thr Ala Pro
4100                4105                4110
```

-continued

Asp Ala Leu Ala Glu Gln His Met Met Glu Glu Ala Leu Arg
 4115             4120              4125

Ser His Leu Ala Ala Asp His Asp Gln Pro His Ala His Arg
 4130             4135              4140

Gln Phe Asn Gln Leu Val Arg Glu Ala Gly Ala Glu Gly Met Ser
 4145             4150              4155

Arg His Lys Arg Leu Phe Asp Val Leu Phe Gly Asn Ala Arg Asn
 4160             4165              4170

Asn Ile Glu Arg Ser Lys Ile His Glu Pro Gly Val Phe Leu Gly
 4175             4180              4185

Asp Val Thr Ile Phe Ser Ala Val Arg Asp His Glu Asp Arg Ser
 4190             4195              4200

Ala Phe Leu Ala Glu Asn Trp Arg Pro Tyr Val Ala Gly Asp Ile
 4205             4210              4215

Val Ile His Glu Ile Asp Cys Thr His Asp Glu Ile Leu Asn Ala
 4220             4225              4230

Asp Val Val Asp Ser Tyr Gly Gln Arg Leu Gly Gln Leu Leu Gly
 4235             4240              4245

Ala Gln Arg Arg Arg Glu Leu Thr Pro Pro Gln Arg Phe Gly Ala
 4250             4255              4260

Asp Pro Gly Asp Asp Glu Pro Pro Val Arg
 4265             4270

<210> SEQ ID NO 18
<211> LENGTH: 21
<212> TYPE: DNA
<213> ORGANISM: Artificial
<220> FEATURE:
<223> OTHER INFORMATION: primer

<400> SEQUENCE: 18
cttgagcagc tcgtaaagcg t                                          21

<210> SEQ ID NO 19
<211> LENGTH: 25
<212> TYPE: DNA
<213> ORGANISM: Artificial
<220> FEATURE:
<223> OTHER INFORMATION: primer

<400> SEQUENCE: 19
gctgtatgag gaagtctatt catgg                                      25

<210> SEQ ID NO 20
<211> LENGTH: 22
<212> TYPE: DNA
<213> ORGANISM: artificial
<220> FEATURE:
<223> OTHER INFORMATION: primer

<400> SEQUENCE: 20
aacgagagga agaactaagc cg                                         22

<210> SEQ ID NO 21
<211> LENGTH: 24
<212> TYPE: DNA
<213> ORGANISM: artificial
<220> FEATURE:
<223> OTHER INFORMATION: primer

<400> SEQUENCE: 21

-continued ttacggagca ggaaggccag cggg                        24

<210> SEQ ID NO 22
<211> LENGTH: 18
<212> TYPE: DNA
<213> ORGANISM: artificial
<220> FEATURE:
<223> OTHER INFORMATION: primer

<400> SEQUENCE: 22
gtcaagggat cggcgagg                               18

<210> SEQ ID NO 23
<211> LENGTH: 19
<212> TYPE: DNA
<213> ORGANISM: artificial
<220> FEATURE:
<223> OTHER INFORMATION: primer

<400> SEQUENCE: 23
tggacttgag cacggtcat                              19

<210> SEQ ID NO 24
<211> LENGTH: 20
<212> TYPE: DNA
<213> ORGANISM: artificial
<220> FEATURE:
<223> OTHER INFORMATION: primer

<400> SEQUENCE: 24
cgttgcgatt tctgcgtagc                             20

<210> SEQ ID NO 25
<211> LENGTH: 20
<212> TYPE: DNA
<213> ORGANISM: artificial
<220> FEATURE:
<223> OTHER INFORMATION: primer

<400> SEQUENCE: 25
ggtgatggtc gtggtcatcc                             20

<210> SEQ ID NO 26
<211> LENGTH: 20
<212> TYPE: DNA
<213> ORGANISM: artificial
<220> FEATURE:
<223> OTHER INFORMATION: primer

<400> SEQUENCE: 26
catatctggc atggctccag                             20

<210> SEQ ID NO 27
<211> LENGTH: 22
<212> TYPE: DNA
<213> ORGANISM: artificial
<220> FEATURE:
<223> OTHER INFORMATION: primer

<400> SEQUENCE: 27
atcgtgttga ccccaaagaa at                          22

<210> SEQ ID NO 28
<211> LENGTH: 20
<212> TYPE: DNA
<213> ORGANISM: artificial

```
<220> FEATURE:
<223> OTHER INFORMATION: primer

<400> SEQUENCE: 28
acaacgaaac ctacctcgtc                                               20

<210> SEQ ID NO 29
<211> LENGTH: 18
<212> TYPE: DNA
<213> ORGANISM: artificial
<220> FEATURE:
<223> OTHER INFORMATION: primer

<400> SEQUENCE: 29
gtgagctggc ggcctaac                                                 18

<210> SEQ ID NO 30
<211> LENGTH: 18
<212> TYPE: DNA
<213> ORGANISM: Artificial
<220> FEATURE:
<223> OTHER INFORMATION: primer

<400> SEQUENCE: 30
gacgagcagc tgtccgag                                                 18

<210> SEQ ID NO 31
<211> LENGTH: 18
<212> TYPE: DNA
<213> ORGANISM: artificial
<220> FEATURE:
<223> OTHER INFORMATION: primer

<400> SEQUENCE: 31
gagagcgtgg ccatcgag                                                 18

<210> SEQ ID NO 32
<211> LENGTH: 20
<212> TYPE: DNA
<213> ORGANISM: artificial
<220> FEATURE:
<223> OTHER INFORMATION: primer

<400> SEQUENCE: 32
ccacagggtt tttggtgaag                                               20

<210> SEQ ID NO 33
<211> LENGTH: 20
<212> TYPE: DNA
<213> ORGANISM: artificial
<220> FEATURE:
<223> OTHER INFORMATION: primer

<400> SEQUENCE: 33
ggaaatccaa cagcaaggac                                               20

<210> SEQ ID NO 34
<211> LENGTH: 22
<212> TYPE: DNA
<213> ORGANISM: artificial
<220> FEATURE:
<223> OTHER INFORMATION: primer

<400> SEQUENCE: 34
cgcggcgagc gggagctggt gc                                            22
```

<210> SEQ ID NO 35
<211> LENGTH: 22
<212> TYPE: DNA
<213> ORGANISM: artificial
<220> FEATURE:
<223> OTHER INFORMATION: primer

<400> SEQUENCE: 35
cgcagcgggg agcgccggtc gg                                            22

<210> SEQ ID NO 36
<211> LENGTH: 20
<212> TYPE: DNA
<213> ORGANISM: artificial
<220> FEATURE:
<223> OTHER INFORMATION: rpimer

<400> SEQUENCE: 36
ggcgttacag aattgccttg                                               20

<210> SEQ ID NO 37
<211> LENGTH: 20
<212> TYPE: DNA
<213> ORGANISM: artificial
<220> FEATURE:
<223> OTHER INFORMATION: primer

<400> SEQUENCE: 37
gctcgaagtt ggagatcagg                                               20

<210> SEQ ID NO 38
<211> LENGTH: 20
<212> TYPE: DNA
<213> ORGANISM: artificial
<220> FEATURE:
<223> OTHER INFORMATION: primer

<400> SEQUENCE: 38
gtacgtggtg accaatgtcg                                               20

<210> SEQ ID NO 39
<211> LENGTH: 20
<212> TYPE: DNA
<213> ORGANISM: artificial
<220> FEATURE:
<223> OTHER INFORMATION: primer

<400> SEQUENCE: 39
tagaaggtgc gggaaagttg                                               20

<210> SEQ ID NO 40
<211> LENGTH: 20
<212> TYPE: DNA
<213> ORGANISM: artificial
<220> FEATURE:
<223> OTHER INFORMATION: primer

<400> SEQUENCE: 40
gtctatctgg cggtgctctc                                               20

<210> SEQ ID NO 41
<211> LENGTH: 20
<212> TYPE: DNA
<213> ORGANISM: artificial
<220> FEATURE:
<223> OTHER INFORMATION: primer

```
<400> SEQUENCE: 41
gtcgaagcag cgttgattgt                                              20

<210> SEQ ID NO 42
<211> LENGTH: 24
<212> TYPE: DNA
<213> ORGANISM: artificial
<220> FEATURE:
<223> OTHER INFORMATION: primer

<400> SEQUENCE: 42
tgttcttcac cacccagggc cggg                                         24

<210> SEQ ID NO 43
<211> LENGTH: 27
<212> TYPE: DNA
<213> ORGANISM: artificial
<220> FEATURE:
<223> OTHER INFORMATION: primer

<400> SEQUENCE: 43
ttgagcgaca gcaggtagtc gtcggcg                                      27

<210> SEQ ID NO 44
<211> LENGTH: 25
<212> TYPE: DNA
<213> ORGANISM: artificial
<220> FEATURE:
<223> OTHER INFORMATION: primer

<400> SEQUENCE: 44
ttggtgcgcc gcaagagcgc aaccg                                        25

<210> SEQ ID NO 45
<211> LENGTH: 23
<212> TYPE: DNA
<213> ORGANISM: artificial
<220> FEATURE:
<223> OTHER INFORMATION: primer

<400> SEQUENCE: 45
atttcagctt gtacagcggt ggc                                          23
```